US012064797B2

(12) United States Patent
VanDerWoude et al.

(10) Patent No.: US 12,064,797 B2
(45) Date of Patent: *Aug. 20, 2024

(54) METHOD OF DISPOSING OF WASTE RECEIVER, WASTE RECEIVER FOR PHARMACEUTICAL WASTE AND METHOD OF ASSEMBLING THE WASTE RECEIVER

(71) Applicant: Stryker Corporation, Kalamazoo, MI (US)

(72) Inventors: Brian James VanDerWoude, Portage, MI (US); David A. Maness, Mt. Pleasant, SC (US); Bryan Matthew Ulmer, Grand Rapids, MI (US); Dennis Meyer, Augusta, MI (US); Lucas Wade, Austin, TX (US); Stephen Myers, Austin, TX (US); Logan Castillo, Georgetown, TX (US); Heather Benoit, Austin, TX (US)

(73) Assignee: Stryker Corporation, Kalamazoo, MI (US)

( * ) Notice: Subject to any disclaimer, the term of this patent is extended or adjusted under 35 U.S.C. 154(b) by 469 days.

This patent is subject to a terminal disclaimer.

(21) Appl. No.: 17/416,635
(22) PCT Filed: Dec. 26, 2019
(86) PCT No.: PCT/US2019/068578
§ 371 (c)(1),
(2) Date: Jun. 21, 2021
(87) PCT Pub. No.: WO2020/139946
PCT Pub. Date: Jul. 2, 2020

(65) Prior Publication Data
US 2022/0062964 A1 Mar. 3, 2022

Related U.S. Application Data

(63) Continuation of application No. 16/233,824, filed on Dec. 27, 2018, now Pat. No. 10,940,513.
(Continued)

(51) Int. Cl.
*A61B 50/36* (2016.01)
*A61B 50/37* (2016.01)
(Continued)

(52) U.S. Cl.
CPC ............ *B09B 3/0075* (2013.01); *A61B 50/36* (2016.02); *A61B 50/362* (2016.02); *A61B 50/37* (2016.02);
(Continued)

(58) Field of Classification Search
CPC .. A61M 5/3205; A61M 5/002; A61M 5/3278; A61B 50/36; A61B 50/362;
(Continued)

(56) References Cited

U.S. PATENT DOCUMENTS

| 4,520,926 A | 6/1985 | Nelson |
| 4,903,832 A | 2/1990 | Stewart |

(Continued)

FOREIGN PATENT DOCUMENTS

| CA | 2164727 A1 | 12/1994 |
| CN | 1071104 A | 4/1993 |

(Continued)

OTHER PUBLICATIONS

English language abstract and machine-assisted English translation for JPH 02-129301 U extracted from Japanese Patent Office database on May 16, 2022, 6 pages.

(Continued)

*Primary Examiner* — King M Chu
(74) *Attorney, Agent, or Firm* — Howard & Howard Attorneys PLLC

(57) ABSTRACT

A waste disposal system (30) with a waste receiver (32) for receiving pharmaceutical waste material. A locking assembly (34) is secured to a fixed surface and actuated from a locked configuration to an unlocked configuration. A lock cylinder of the locking assembly may extend forward of a front wall (44) of a receiver body (36) of the waste receiver to engage a locking feature of a cover (82) in the locked configuration. A cover retention feature (124) may prevent (Continued)

axial decoupling of the cover from the receiver body. The receiver body may be formed from two shells (62,64). A reaction agent (150) is positioned within the container volume and spaced apart from a bottom wall of the receiver body. The reaction agent may be positioned within the container volume between the lock passageway (94) and/or a solid receiver volume, and opposing sidewalls of the receiver body. A support may maintain the position of the reaction agent within the container volume.

20 Claims, 26 Drawing Sheets

Related U.S. Application Data

(60) Provisional application No. 62/935,898, filed on Nov. 15, 2019.

(51) Int. Cl.
| | |
|---|---|
| *A61B 50/39* | (2016.01) |
| *A61M 5/32* | (2006.01) |
| *A62D 3/30* | (2007.01) |
| *B09B 1/00* | (2006.01) |
| *B09B 3/00* | (2022.01) |
| *B09B 3/10* | (2022.01) |
| *B65F 1/16* | (2006.01) |
| *A61B 50/00* | (2016.01) |
| *A61B 50/30* | (2016.01) |
| *A61B 90/00* | (2016.01) |

(52) U.S. Cl.
CPC .......... *A61B 50/39* (2016.02); *A61M 5/3205* (2013.01); *A62D 3/30* (2013.01); *B09B 1/00* (2013.01); *B09B 3/10* (2022.01); *B65F 1/1615* (2013.01); *A61B 2050/005* (2016.02); *A61B 2050/0054* (2016.02); *A61B 2050/3008* (2016.02); *A61B 2090/0807* (2016.02); *B65F 2210/148* (2013.01); *B65F 2240/145* (2013.01)

(58) Field of Classification Search
CPC ............... A61B 50/39; A61B 50/3001; A61B 2050/105; B65F 1/141
USPC .................. 206/366, 370, 364; 220/908, 481
See application file for complete search history.

(56) References Cited

U.S. PATENT DOCUMENTS

| | | | |
|---|---|---|---|
| 5,035,367 | A | 7/1991 | Nojima |
| 5,165,563 | A | 11/1992 | McKendry |
| 5,351,381 | A | 10/1994 | Case |
| 5,385,105 | A | 1/1995 | Withers, Jr. et al. |
| 5,413,243 | A | 5/1995 | Bemis et al. |
| 5,417,659 | A | 5/1995 | Gaba |
| 5,419,435 | A | 5/1995 | Perzan et al. |
| 5,429,315 | A | 7/1995 | Wollert et al. |
| 5,516,052 | A | 5/1996 | Adams et al. |
| 5,590,840 | A | 1/1997 | Adams et al. |
| 6,588,436 | B2 | 7/2003 | Dunn et al. |
| 6,652,495 | B1 | 11/2003 | Walker |
| 7,798,358 | B2 | 9/2010 | Butler et al. |
| 7,918,776 | B2 | 4/2011 | Day |
| 7,918,777 | B2 | 4/2011 | Parrott |
| 8,038,025 | B2 | 10/2011 | Stark et al. |
| 8,348,056 | B2 | 1/2013 | Maness |
| 8,490,795 | B2 | 7/2013 | Ziemba |
| 8,534,459 | B2 | 9/2013 | Maness |
| 8,535,711 | B2 | 9/2013 | Anderson et al. |
| 8,573,426 | B2 * | 11/2013 | Maness ................. B09B 3/0075 206/370 |
| 8,616,397 | B2 | 12/2013 | Maness |
| 8,875,881 | B2 | 11/2014 | Smudde et al. |
| 8,979,724 | B2 | 3/2015 | Fowler et al. |
| 9,044,377 | B2 | 6/2015 | Maness |
| 9,161,874 | B2 | 10/2015 | Pennings et al. |
| 9,302,134 | B1 | 4/2016 | Nelson et al. |
| 9,456,954 | B2 | 10/2016 | Maness |
| 9,707,324 | B2 | 7/2017 | Morgan et al. |
| 9,775,683 | B2 | 10/2017 | Stark |
| 9,839,479 | B2 | 12/2017 | Sichau et al. |
| 9,962,227 | B2 | 5/2018 | Slaateng |
| 10,492,971 | B2 | 12/2019 | Pennings et al. |
| 10,524,873 | B2 | 1/2020 | Sall et al. |
| 10,940,513 | B2 | 3/2021 | VanderWoude et al. |
| 11,185,639 | B2 | 11/2021 | Renstad et al. |
| 2007/0032764 | A1 | 2/2007 | Lampropoulos |
| 2009/0120820 | A1 * | 5/2009 | Iske ..................... A61M 5/3205 414/808 |
| 2012/0024724 | A1 | 2/2012 | Beardsall et al. |
| 2012/0305132 | A1 | 12/2012 | Maness |
| 2014/0183070 | A1 | 7/2014 | Holaday et al. |
| 2016/0325322 | A1 | 11/2016 | Maness |
| 2016/0361456 | A1 | 12/2016 | Admani |
| 2019/0126331 | A1 | 5/2019 | VanderWoude et al. |
| 2021/0154711 | A1 | 5/2021 | VanDerWoude et al. |
| 2022/0062964 | A1 | 3/2022 | VanDerWoude et al. |

FOREIGN PATENT DOCUMENTS

| | | |
|---|---|---|
| CN | 1906100 A | 1/2007 |
| CN | 101643138 A | 2/2010 |
| CN | 103945787 A | 7/2014 |
| CN | 204751174 U | 11/2015 |
| EP | 1380316 B1 | 10/2007 |
| FR | 2760647 A1 | 9/1998 |
| JP | H02129301 U | 10/1990 |
| WO | 8404068 A1 | 10/1984 |
| WO | 2010138767 A2 | 12/2010 |
| WO | 2010138767 A3 | 3/2011 |
| WO | 2014133398 A1 | 9/2014 |

OTHER PUBLICATIONS

English language abstract and machine-assisted English translation for CN 204751174 extracted from espacenet.com database on Feb. 27, 2019, 7 pages.
English language abstract and machine-assisted English translation for EP 1 380 316 extracted from espacenet.com database on Feb. 27, 2019, 28 pages.
English language abstract and machine-assisted English translation for FR 2 760 647 extracted from espacenet.com database on Feb. 27, 2019, 14 pages.
International Search Report for Application No. PCT/US2018/040359 dated Nov. 13, 2018, 5 pages.
International Search Report for Application No. PCT/US2019/068578 dated Apr. 7, 2020, 5 pages.
Machine-assisted English translation for CN 1071104 extracted from espacenet.com database on Feb. 27, 2019, 22 pages.
Morris, Ph.D., Russell et al., "Performance Evaluation: RAPIX Filtration System for the Denaturing and Disposal of Unwanted Liquid Medications", Feb. 9, 2017, 4 pages.
Partial International Search Report for Application No. PCT/US2018/040359 dated Sep. 18, 2018, 4 pages.
Stericycle Inc., "Stericycle CSRX System Brochure", 2016, 2 pages.
Stryker, "Cactus Smart Sink Brochure—Frequently Asked Questions", 2017, 5 pages.
Stryker, "Controlled Substance Waste Management Systems Brochure", 2017, 6 pages.
Stryker, "Pharma Lock OR Controlled Substance Waste Management System, REF 0085-002-001 Instructions for Use", Apr. 2017, 13 pages.
Stryker, "Smart Sink Controlled Substance Waste Management System Instructions for Use, REF 0085-000-000", Apr. 2017, 29 pages.

(56) References Cited

OTHER PUBLICATIONS

Vail Scientific L.L.C., "Rapix Frequently Asked Questions", Oct. 21, 2016, 3 pages.
English language abstract for CN 1906100 A extracted from espacenet.com database on Nov. 28, 2022, 2 pages.
English language abstract for CN 101643138 A extracted from espacenet.com database on Nov. 28, 2022, 1 page.
English language abstract for CN 103945787 A extracted from espacenet.com database on Nov. 28, 2022, 2 pages.

\* cited by examiner

METHOD OF DISPOSING OF WASTE RECEIVER, WASTE RECEIVER FOR PHARMACEUTICAL WASTE AND METHOD OF ASSEMBLING THE WASTE RECEIVER

PRIORITY CLAIM

This application is the National Stage of International Application No. PCT/US2019/068578 filed on Dec. 26, 2019, which claims priority to and all the benefits of U.S. patent application Ser. No. 16/233,824, filed on Dec. 27, 2018, now U.S. Pat. No. 10,940,513, issued on Mar. 9, 2021, and U.S. Provisional Patent Application No. 62/935,898, filed on Nov. 15, 2019. Each of the above applications is hereby incorporated by reference in its entirety.

BACKGROUND

The disposal of pharmaceutical waste material has long been a concern of those in the medical care industry. Pharmaceutical waste material may include, for example, expired or discontinued medicine, unused products such as partially or completely filled vials or IV bags, defective medicinal applicators, and other potentially dangerous or hazardous waste materials. The pharmaceutical waste material may be liquid phase pharmaceutical waste material contained within a syringe, bag, or bottle, or solid phase pharmaceutical waste material such as pills, capsules, powders, patches, etc. Ensuring that the pharmaceutical waste material is not improperly diverted or discarded is of utmost importance. Conventional methods such as incineration are labor and capital-intensive, and often require shipment of the pharmaceutical waste material outside the medical facility and are associated with regulatory and practical challenges. Further, minimizing environmental impact is also desired over other conventional methods such as "sewering," in which the pharmaceutical waste material is simply discarded down a drain.

Under conventional disposal methods, the means by which pharmaceutical waste material may be disposed is often inconveniently dependent upon the specific type of waste. Methods such as incineration are becoming much less preferred, and often require shipment of the pharmaceutical waste material outside the medical facility. The shipment of the pharmaceutical waste material is associated with risk of diversion during transport, and transport of liquid phase pharmaceutical waste material, which may include hazardous waste, is associated with regulatory and practical challenges.

Conventional waste disposal systems may include a receiver or container, and it is known to include a reaction agent within the container volume to render the liquid phase pharmaceutical waste material irrecoverable or irretrievable. For example, commonly-owned U.S. Pat. No. 9,044,377, issued Jun. 2, 2015, and hereby incorporated by reference in its entirety, discloses a reaction agent positioned either on a bottom of the container or arranged in layers (with a fluid absorber) from the bottom of the container. Limiting the reaction agent to the bottom of the container may be insufficient once the liquid level of the liquid phase pharmaceutical waste material rises.

Further, attempts to use waste disposal systems have not been altogether satisfactory. Conventional waste disposal systems occupy a substantial amount of valuable floor space in a hospital, for example, and may make providing such systems several points of use around the hospital unfeasible. Further, the conventional waste disposal systems may not provide adequate safeguards to foreclose the opportunity to retrieve and recover the waste material, a particularly pronounced problem with narcotic pain medications contained in pill and patch forms.

Therefore, a need exists in the art for a waste receiver and a waste disposal system that overcomes one or more of the aforementioned disadvantages.

SUMMARY

A method of disposing of a waste receiver including a cover coupled to a cover retention feature of a receiver body with the receiver body defining an opening for receiving pharmaceutical waste material and further defining a lock passageway separate from the opening, wherein the waste receiver is coupled to a locking assembly secured to a fixed surface in a locked configuration in which a lock housing of the locking assembly is positioned at least partially within the lock passageway and an engagement feature of the locking assembly engages the receiver body to prevent removal of the waste receiver from the locking assembly, said method comprising the steps of: actuating the locking assembly from the locked configuration to an unlocked configuration in which the engagement feature is moved to disengage from the receiver body and the receiver body is moved away from the fixed surface to disengage the locking assembly from the cover, wherein the cover retention feature maintains coupling between the cover and the receiver body; providing an input to the cover to decouple the cover from the cover retention feature of the receiver body; coupling the cover with the receiver body over the opening to seal the pharmaceutical waste material within the receiver body; removing the waste receiver from the locking assembly; and disposing of the waste receiver.

A waste receiver for receiving pharmaceutical waste material and adapted to be releasably coupled to a locking assembly secured to a fixed surface, said waste receiver comprising: a receiver body defining an opening for receiving the pharmaceutical waste material and comprising an inner surface defining a container volume in fluid communication with said opening, and an outer surface opposite said inner surface, wherein said inner and outer surfaces form at a front wall, a rear wall opposite said front wall, and opposing sidewalls extending between said front and rear walls with apertures within said front and rear walls defining a portion of said lock passageway adapted to receive the locking assembly; a fluid absorber disposed within said receiver body; a chemical composition disposed within said receiver body; a first cover retention feature coupled to said front wall of said receiver body; a second cover retention feature on said receiver body near said opening; a cover coupled to said first cover retention feature, wherein said cover is configured to be decoupled from said first cover retention feature and coupled with said second cover retention feature to be positioned over said opening and seal the pharmaceutical waste material within said container volume for disposal of said waste receiver.

A waste receiver for receiving pharmaceutical waste material. A receiver body defines a container volume and an opening in fluid communication with the container volume. The opening is for receiving the pharmaceutical waste material. The receiver body includes a front wall, a rear wall opposite the front wall, and opposing sidewalls extending between the front and rear walls. The receiver body defines a lock passageway adapted to receive a locking assembly, the lock passageway being separate from the opening and extending through the receiver body between the front and rear walls. A reaction agent is positioned within a region of the container volume defined between the lock passageway and one of the opposing sidewalls of the receiver body.

A waste receiver for receiving pharmaceutical waste material. The waste receiver includes a receiver body defining a container volume and an opening in fluid communication with the container volume. The opening is for receiving the pharmaceutical waste material. The receiver body includes a front wall, a rear wall opposite the front wall, opposing sidewalls extending between the front and rear walls, and a bottom wall extending between the opposing sidewalls. The receiver body defines a lock passageway adapted to receive the locking assembly. The lock passageway is separate from the opening and extending through the receiver body between the front and rear walls. A support is coupled to the receiver body within the container volume. A reaction agent disposed within the container volume and supported by the support so as to be spaced apart from the bottom wall of the receiver body.

A waste receiver for receiving liquid and solid phase pharmaceutical waste material. The waste receiver includes two shells joined to one another to form a receiver body defining an opening for receiving the liquid and solid phase pharmaceutical waste material. The two shells cooperate to define a liquid waste receiver volume in fluid communication with the opening. A reaction agent is positioned within the liquid waste receiver volume. The two shells cooperate to define a lock passageway separate from the opening and extending through the receiver body. A singular one of the two shells defines a solid waste receiver volume substantially separate from the liquid waste receiver volume and in fluid communication with the opening.

A waste receiver for receiving pharmaceutical waste material. The waste receiver includes a receiver body defining a container volume and an opening in fluid communication with the container volume. The opening is for receiving the pharmaceutical waste material. The receiver body includes a front wall, a rear wall opposite the front wall, opposing sidewalls extending between the front and rear walls, and a bottom wall extending between the opposing sidewalls. The receiver body defines a lock passageway adapted to receive a locking assembly. The lock passageway is separate from the opening and extending through the receiver body between the front and rear walls. A reaction agent is disposed within the container volume. The reaction agent is positioned to be spaced apart from the bottom wall.

A waste receiver for receiving pharmaceutical waste material. The waste receiver includes a receiver body defining a container volume and an opening in fluid communication with the container volume. The opening is for receiving the pharmaceutical waste material. The receiver body including a front wall, a rear wall opposite the front wall, opposing sidewalls extending between the front and rear walls, top wall extending between the opposing sidewalls with the opening extending through the top wall, and a bottom wall opposite the top wall. The receiver body defines a lock passageway extending through the receiver body between the front and rear walls. A plane bifurcating the opening and the lock passageway divides the container volume into at least two regions. A reaction agent is positioned within one of the at least two regions of the container volume and further positioned to be spaced apart from the bottom wall of the receiver body.

A method of assembling a waste receiver for receiving liquid and solid phase pharmaceutical waste material. The reaction agent is positioned to be supported with the support. Thereafter, the two shells are joined to form a receiver body defining an opening for receiving the liquid and solid phase pharmaceutical waste material. The two shells cooperate to define a lock passageway separate from the opening and extending through and between front and rear walls of the receiver body. The two shells further cooperate to define a liquid waste receiver volume in fluid communication with the opening. A reaction agent is disposed in the liquid waste receiver volume and spaced apart from a bottom wall of the receiver body.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
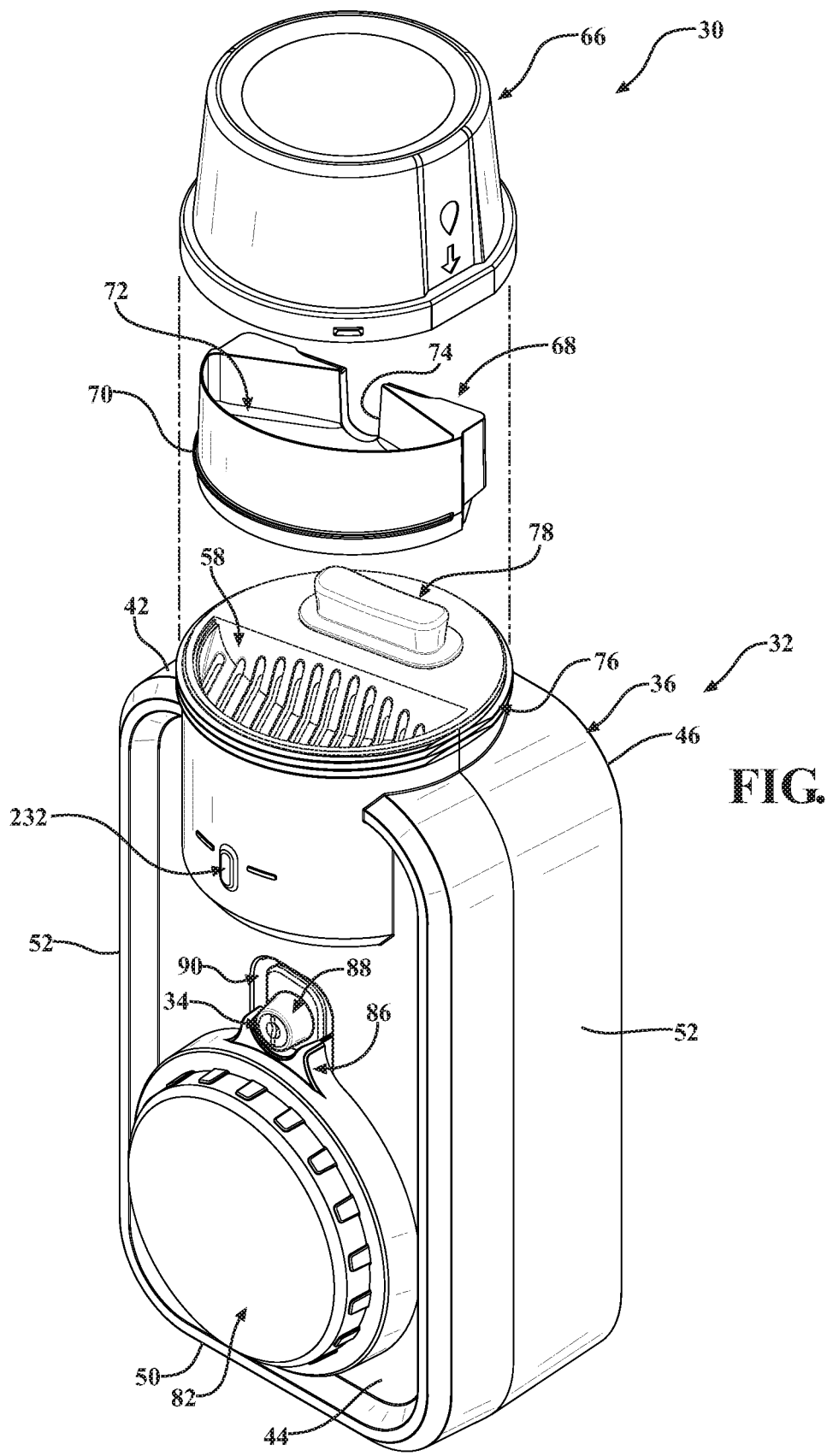
FIG. 1 is a perspective view of a waste disposal system including a waste receiver, a locking assembly, a cap, and a priming aide.
Figure 2:
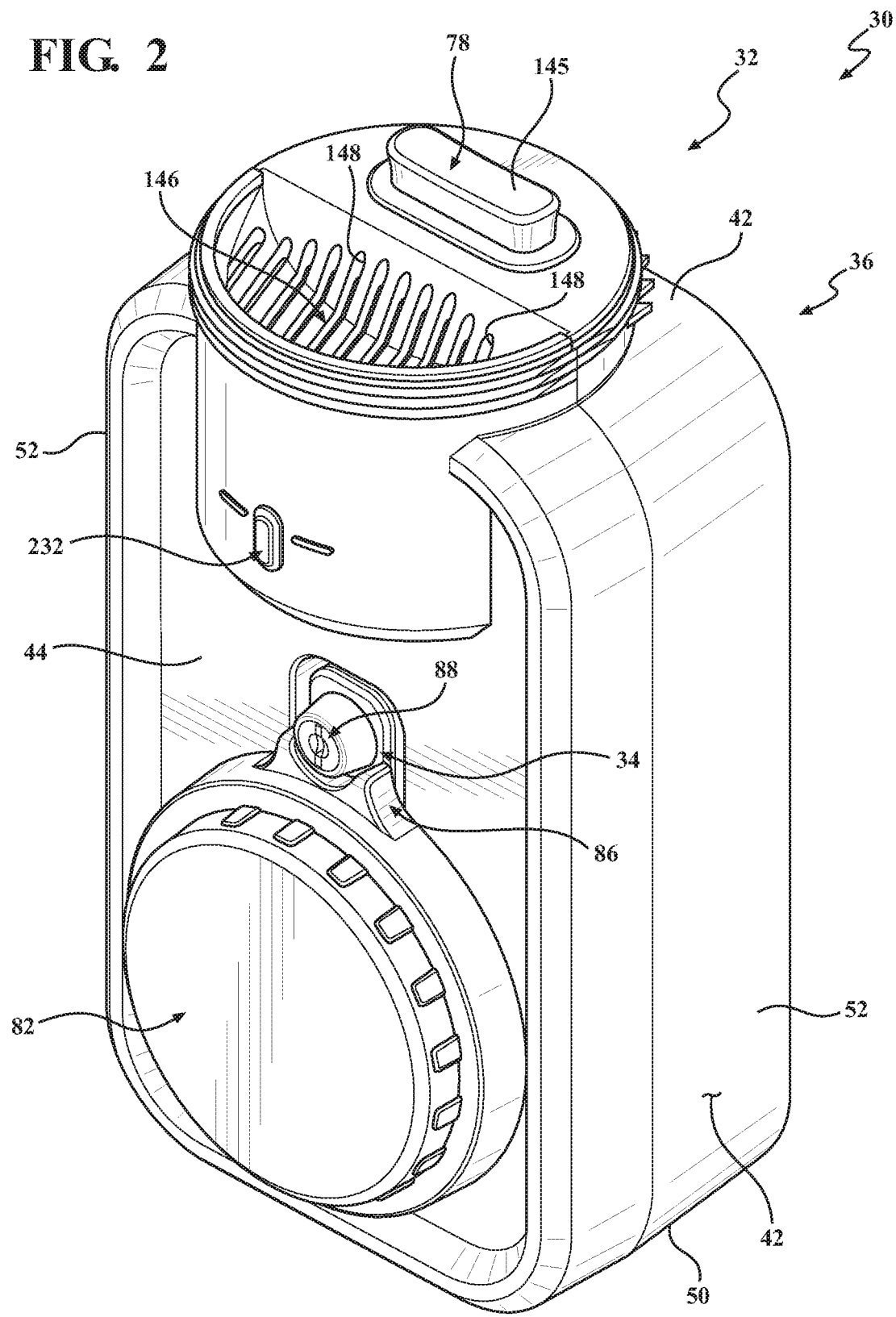
FIG. 2 is a perspective view of the waste disposal system.
Figure 3:
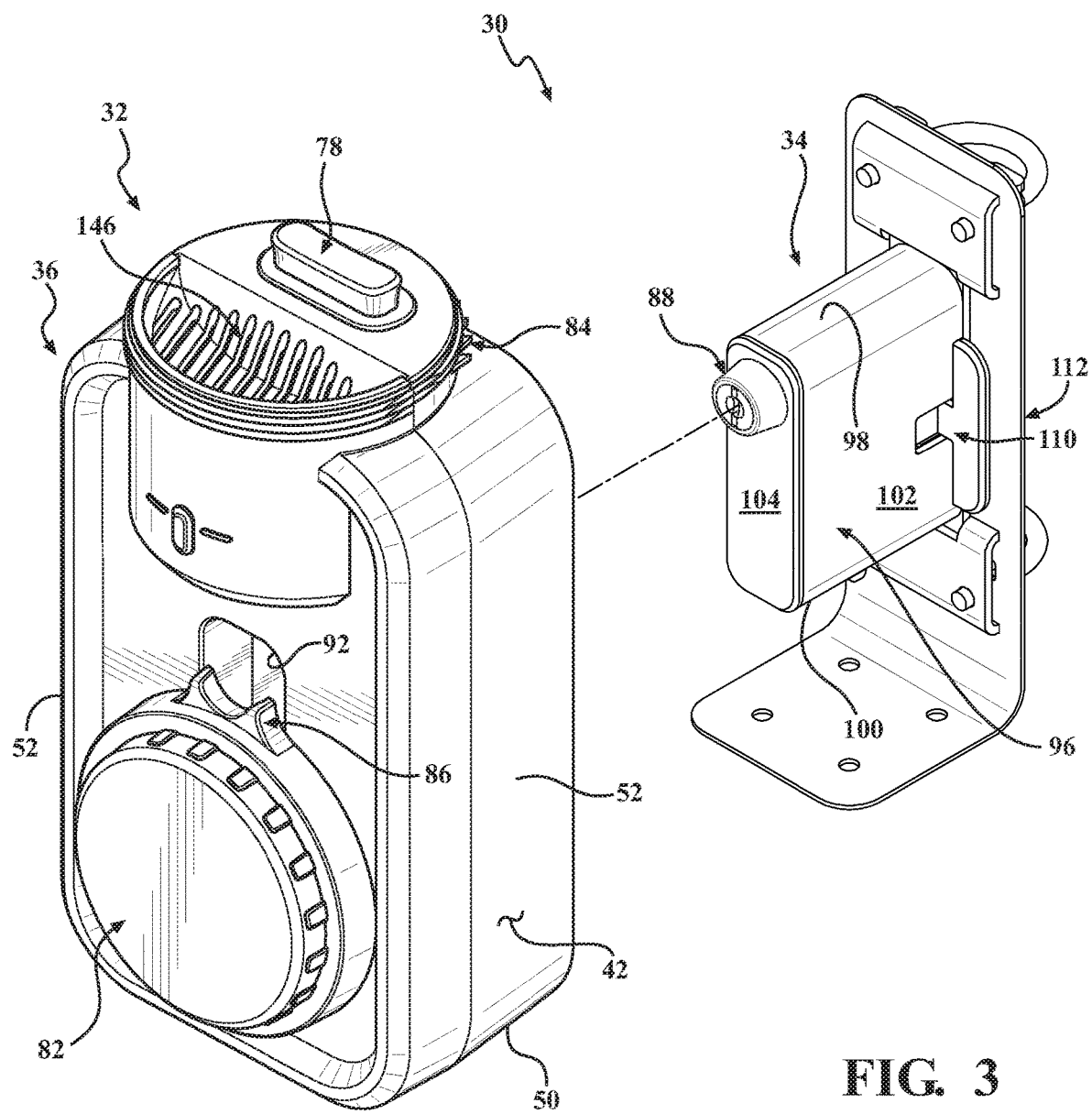
FIG. 3 is a partially exploded front perspective view of the waste disposal system.
Figure 4:
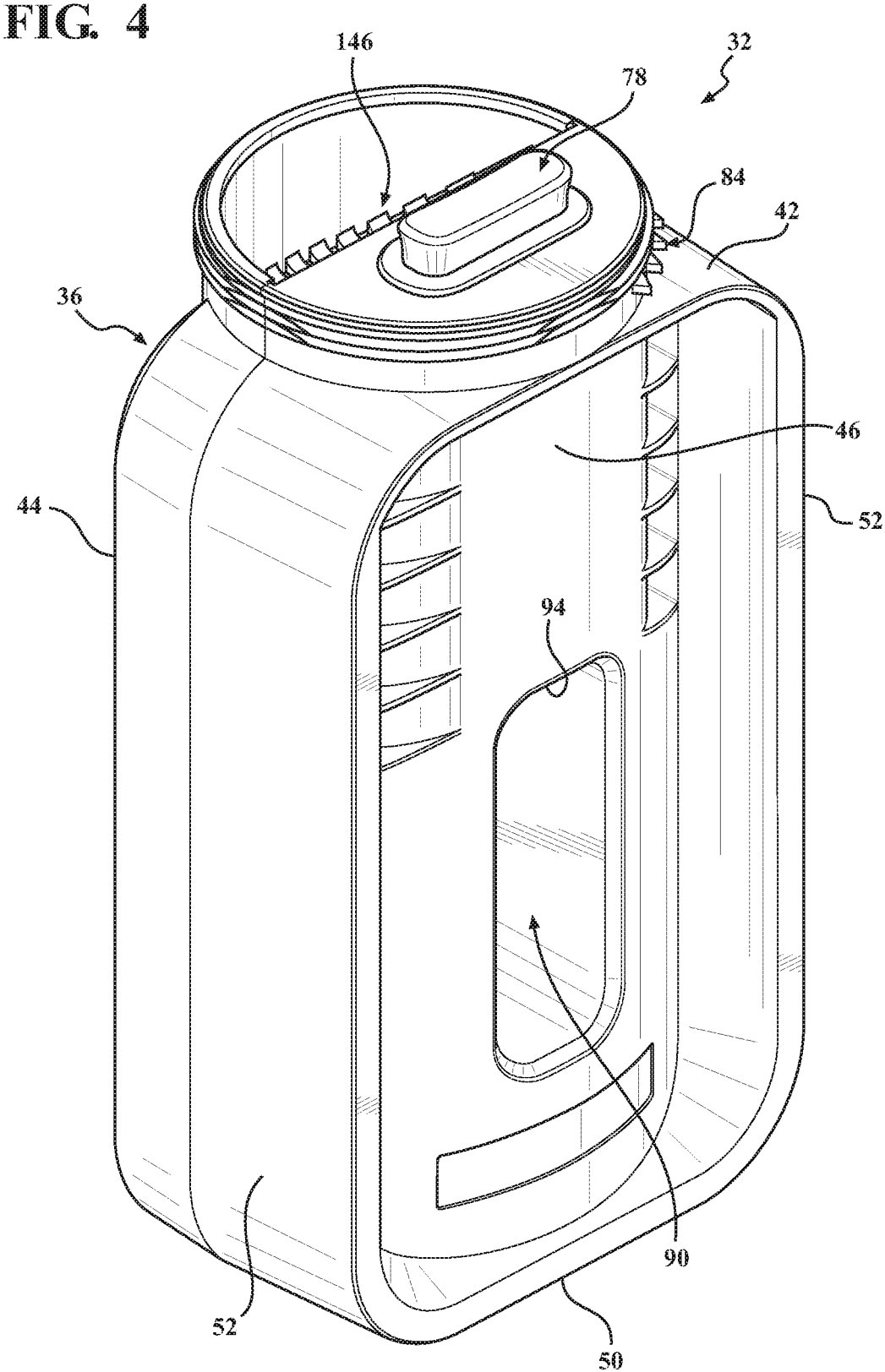
FIG. 4 is a rear perspective view of the waste receiver.

FIGS. 1-3 show a waste disposal system 30 including a waste receiver 32 and a locking assembly 34. The waste receiver 32, in a most general sense, is a vessel or container providing for receipt and/or disposal of pharmaceutical waste material, preferably in a space-efficient manner that renders the waste material irretrievable and/or unrecoverable. As mentioned, the pharmaceutical waste material may include solid phase pharmaceutical waste material and/or liquid phase pharmaceutical waste material. Examples of solid phase pharmaceutical waste material of particular interest are patches and pills, and an example of liquid phase pharmaceutical waste material are fluid-based medications. As to be described in detail, the waste receiver 32 may be adapted to be releasably secured to a fixed surface with the locking assembly 34, for example, a wall, a door, a tabletop, a cart, an upstanding post, and the like. The locking assembly 34 includes a bracket adapted to be secured to the fixed surface, for example, with fasteners (e.g., screws, bolts, rivets, etc.). The locking assembly 34 prevents unauthorized personnel from removing the waste receiver 32 from its service location and lessens the likelihood that pharmaceutical waste material received within the waste receiver 32 may be improperly retrieved, recovered, and/or diverted.

The locking assembly 34 previously mentioned releasably secures the waste receiver 32 to a fixed surface (not shown), for example, a wall, a door, a tabletop, a cart, a upstanding post, and the like. The waste disposal system 30 includes a bracket 112 adapted to be secured to the fixed surface. The bracket 112 includes a vertical mount and/or a horizontal mount, for example, formed as an L-shaped member as shown. The bracket 112 may further include one or more anchors and one or more anchor plates to be secured to the anchors. The anchors may include U-shaped rings configured to surround a fixed structure of the fixed surface such that, subsequent to securing the anchor plates to the anchors opposite the vertical mount, the bracket 112 may not be decoupled from the fixed surface without extraordinary difficulty. The horizontal mount may include holes configured to receive fasteners (e.g., screws, bolts, rivets, etc.) to secure the bracket 112 to a horizontal fixed surface. Further details regarding the construction of the locking assembly are disclosed in commonly-owned International Publication No. WO2019/006346, published Jan. 3, 2019, the entire contents of which ere hereby incorporated by reference.

Figure 9:
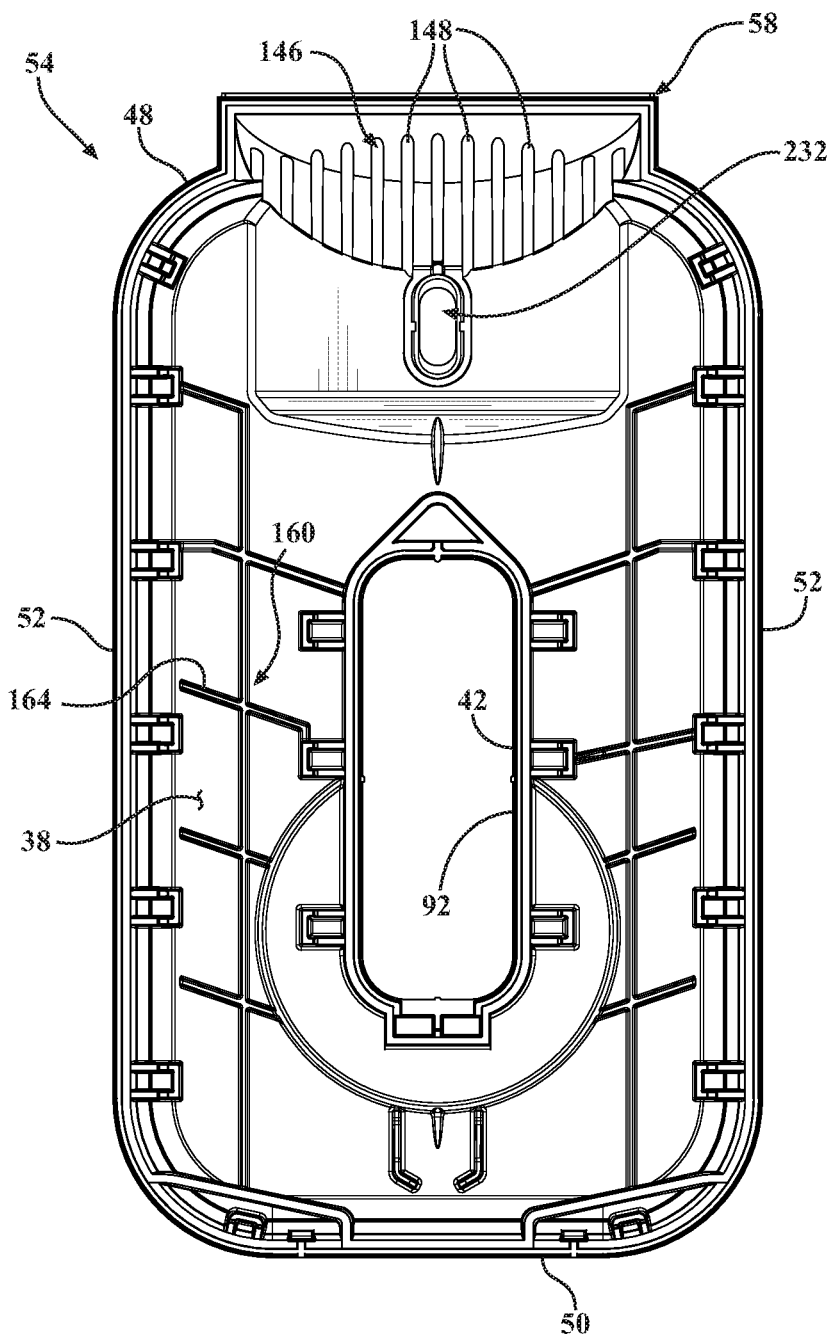
FIG. 9 is a rear elevation view of a front shell of the waste receiver.
Figure 10:
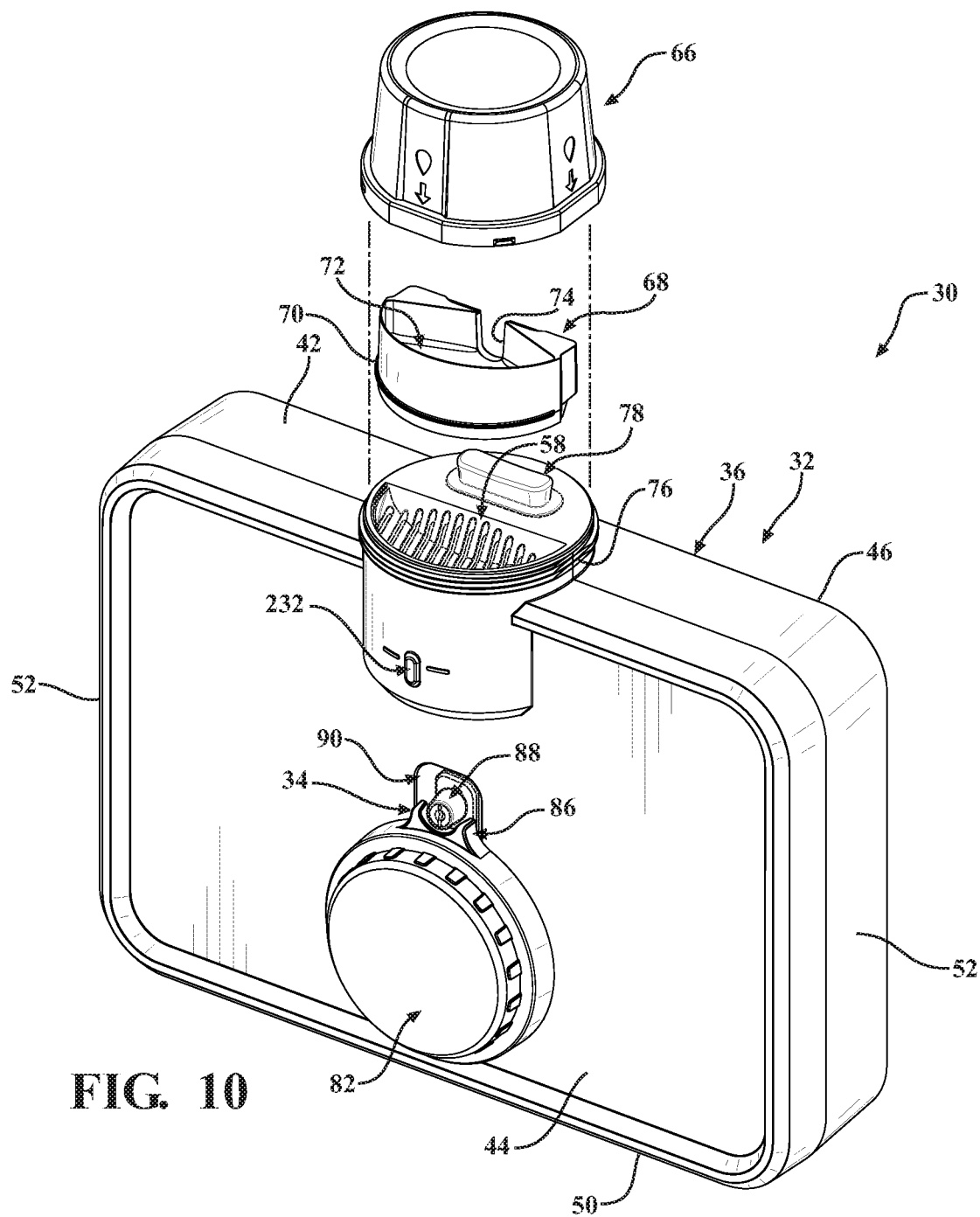
FIG. 10 is a perspective view of the waste disposal system including another waste receiver and the locking assembly.
Figure 11:
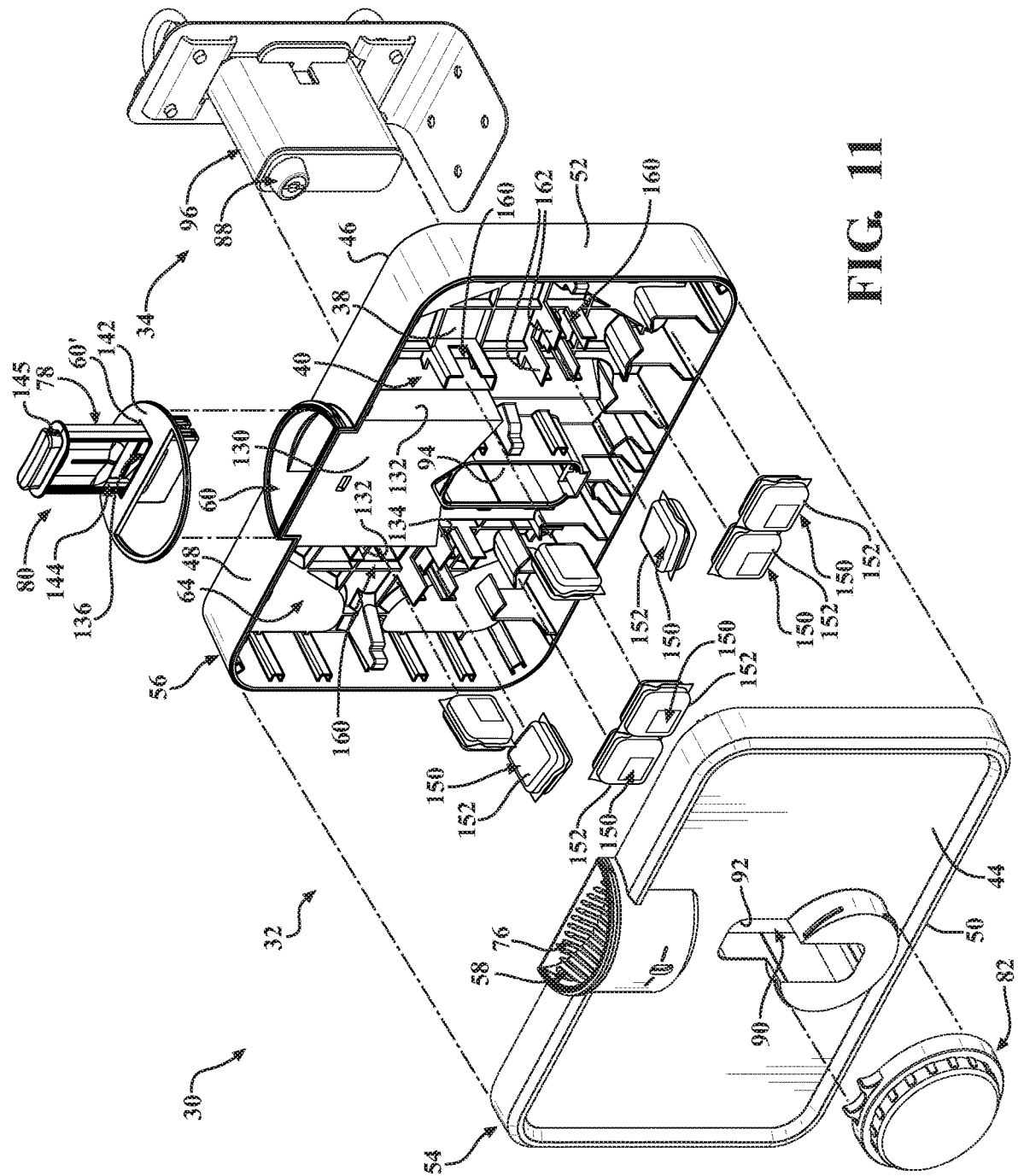
FIG. 11 is an exploded front perspective view of the waste disposal system of FIG. 10.

The waste receiver 32 includes a receiver body 36 with at least an inner surface 38 defining a container volume 40, and an outer surface 42 opposite the inner surface 38. The inner surface 38 and the outer surface 42 cooperate to define at least one wall forming the receiver body 36. The wall(s) may include a front wall 44 opposite a rear wall 46, a top wall 48 opposite a bottom wall 50, and one or more sidewalls 52 extending between the top and bottom walls 50, 94. The receiver body 36 may be monolithic in construction such that the walls 44-52 are integrally formed. Alternatively, as to be described in detail, the receiver body 36 may be formed from shells 62, 64, including a front shell 54 and a rear shell 56. The figures show fillets extending between several adjacent, integrally-formed walls such that a discrete boundary between the adjacent walls is not clearly delineated, but it is understood that the front wall 44 is associated with a front of the receiver body 36, the rear wall 46 is associated with a rear of the receiver body 36, the top wall 42 is associated with a top of the receiver body 36, the bottom wall 50 is associated with a bottom of the receiver body 36, and the sidewalls 52 are associated with sides of the receiver body 36. The walls 44-52 may form the receiver body 36 that is generally shaped as a rectangular prism. FIGS. 10 and 11 show the receiver body 36 being wider and defining a larger container volume 40 relative to the receiver body 36 of FIGS. 1-4 and 7-9. It is contemplated that the receiver body 36 may assume any suitable three-dimensional shape, for example, a cylinder, a cube, a sphere, a cone (including its frustum), a pyramid, and/or higher-order polygons. The rectangular prism may be particularly advantageous to maximize the container volume 40 with a lower profile when secured to the fixed surface in a manner to be described. The proportions of the walls 44-52 forming the receiver body 36 are merely exemplary and may be designed in accordance with the space constraints of its service location and/or other needs of the particular application.

The receiver body 36 may define a first opening 58 and/or a second opening 60 (see FIGS. 7 and 11) in fluid communication with the container volume 40. The container volume 40 may include a solid waste receiver volume 62 and a liquid waste receiver volume 64. The first opening 58 in fluid communication with the liquid waste receiver volume 64, and the second opening 60 in fluid communication with the solid waste receiver volume 62. The first opening 58 is configured to receive the liquid phase pharmaceutical waste material to be disposed within the liquid waste receiver volume 64, and the second opening 60 is configured to receive the solid phase pharmaceutical waste material to be disposed within the solid waste receiver volume 62, for example, under the influence of gravity.

The waste receiver 32 may include a cap 66 coupled to a neck 76. The cap 66 may be coupled with the receiver body 36 at the time of assembly of the waste receiver 32. As will be described in detail, the waste receiver 32 may include a chemical composition (e.g., a fluid absorber and/or a reaction agent) within the container volume 40 upon assembly and prior to shipment and installation of the waste receiver 32 at its service location. The cap 66 prevents inadvertent egress of those contents from the container volume 40 during shipment and handling of the waste receiver 32 prior to installation. Moreover, once the waste receiver 32 is installed at its service location, the cap 66 is decoupled from the receiver body 36. The cap 66 may be used to direct a liquid through the first opening 58 to prime the solid waste receiver volume 62 by activating chemical composition and/or remain within the solid waste receiver volume 62 for dissolving the solid phase pharmaceutical waste material. A priming aide 68 may be provided to facilitate the priming of the solid waste receiver volume 62. With continued reference to FIGS. 1 and 10, the priming aide 68 may be a funnel-type device that includes a body portion 70 defining a recess 72. The body portion 70 is sized to be removably situated within the first opening 58. A neck 76 of the receiver body 36 may be engaged by a lip disposed on the body portion 70 so as to support the priming aide 68. The priming aide 68 may be further shaped to be disposed within the cap 66 during assembly and shipping. The body portion 70 further defines an aperture 74, for example, a slot. The aperture 74 is in communication with the recess 72, and further configured to be arranged in fluid communication with the second opening 60.

After the cap 66 is decoupled from the receiver body 36, the priming aide 68 is exposed. The cap 66 is filled with a liquid, and the liquid is poured into the recess 72 of the priming aide 68 situated atop the receiver body 36. Owing to the funnel-type nature of the recess 72, the liquid is diverted towards and through the aperture 74, and into the second opening 60. It may be necessary for the user to move a pushing member 78 to be described to expose an inlet 60' of a solid receiver guide 80 in communication with the second opening 60 (see FIGS. 7 and 11). Since the recess 72 is relatively larger than the inlet 60', the priming aide 68 makes providing liquid to the solid waste receiver volume 64 easier with less likelihood of spilling. The cap 66 and the priming aide 68 may be discarded, and the waste receiver 32 is ready for use once deployed at its service location.

Figure 5:
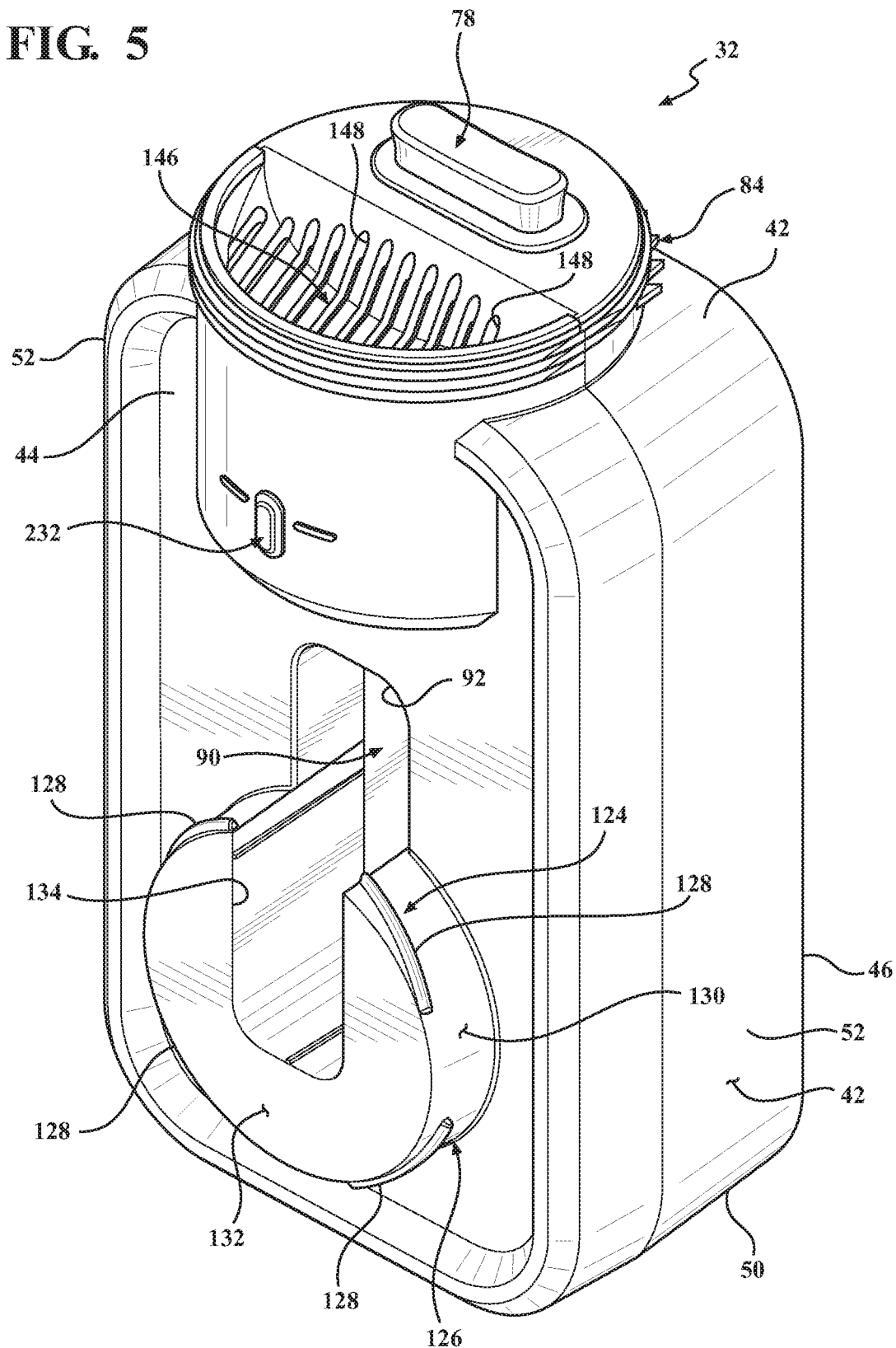
FIG. 5 is a front perspective view of the waster receiver.
Figure 6:
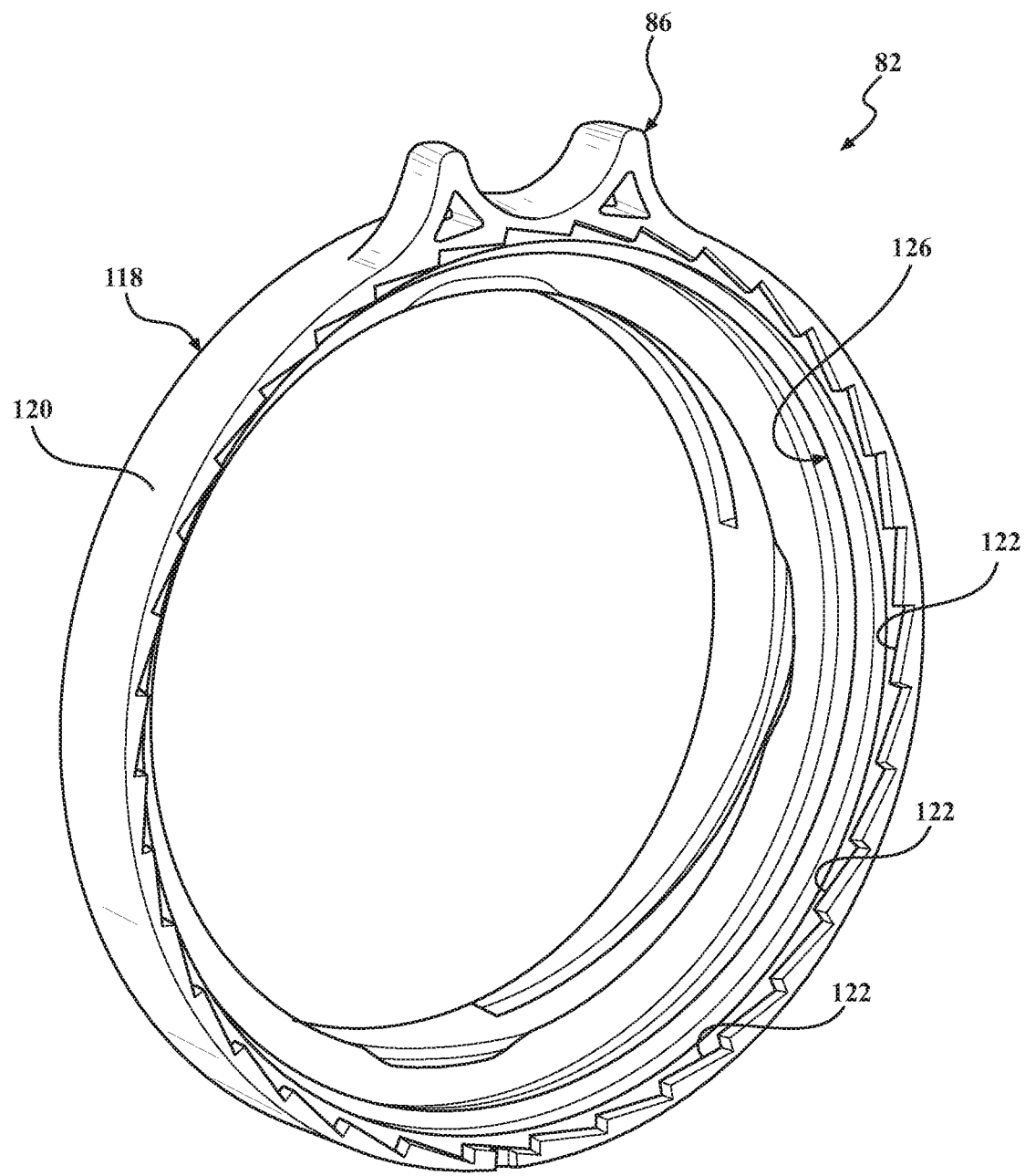
FIG. 6 is a rear perspective view of a cover.

The first and second openings 58, 60 may remain in communication with the ambient atmosphere for receiving the pharmaceutical waste material during the operational lifecycle of the waste receiver 32. Once the waste receiver 32 is ready to be disposed, a cover 82 may be used to seal the pharmaceutical waste material within the container volume 40 of the receiver body 36, in particular prior to disposal of the waste receiver 32. The cover 82 is configured to be coupled with the receiver body 36 over the first and second openings 58, 60 to seal the pharmaceutical waste material within the container volume 40, and in particular prior to disposal of the waste receiver 32. The receiver body 36 may include one or more coupling features for engaging complementary coupling features of the cover 82 in a manner that renders the waste material irretrievable. For example, the coupling features may include teeth suitably positioned engage complementary teeth and permit rotation of the cover 82 relative to the receiver body 36 in a single direction. For example, the waste receiver 32 may include one or more coupling features 84 (see FIGS. 3-5) for receiving complementary coupling features (not shown) of the cover 82 in a manner that renders the waste material irretrievable. The coupling features 84 may include teeth suitably positioned on or near the neck 76 and arranged to engage complementary teeth (not shown) disposed on an underside of the cover 82. The coupling features 84 may further include threads configured to receive complementary threads (not shown) disposed on the underside of the cover 82. As best shown in FIG. 6, the teeth are shaped to permit rotation of the cover 82 relative to the receiver body 36 in a single direction. More particularly, the complementary teeth and the complementary threads of each of the cover 82 and the receiver body 36 cooperate to permit the cover 82 to rotate relative to the receiver body 36 in a first direction (R1) and prevent the cover 82 from rotating relative to the receiver body 36 in a section direction (R2) opposite the first direction. As a result, once it is desired to seal the pharmaceutical waste material within the container volume 40 prior to disposal, the cover 82 is irreversibly coupled with the receiver body 36 with the coupling features 84. After the sealing of the waste receiver 32 by a user with authorization to do so, the pharmaceutical waste material is irretrievable to those within the subsequent chain of custody of the waste receiver 32.

The cover 82 may include a locking feature 86, for example, a U-shaped flange configured to receive a lock cylinder 88 of the locking assembly 34 between upstanding ends of the U-shaped flange, as shown in FIGS. 1, 2 and 10. The engagement between the locking feature 86 and the lock cylinder 88 prevents rotational decoupling of the cover 82 from the locking assembly 34 when the waste receiver 32 is releasably secured to the locking assembly 34. The arrangement permits the cover 82 to be nested in abutment with the front wall 44 of the receiver body 36 such that the locking feature 86 is positioned adjacent a lock passageway 90 when the cover 82 is coupled to the receiver body 36 (and thus permitting engagement of the lock cylinder 88). In a manner to be further described, once it is desired to seal the pharmaceutical waste material within the container volume 40 prior to disposal, the locking assembly 34 is unlocked which permits disengagement of the lock cylinder 88 from the locking feature 86. The cover 82 may be removed and irreversibly coupled with the receiver body 36. After the sealing of the waste receiver 32 by a user with authorization to do so, the pharmaceutical waste material is irretrievable to those within the subsequent chain of custody of the waste receiver 32.

The receiver body 36 may define the lock passageway 90. The lock passageway 90 may be considered separate from the first and second openings 58, 60 of the receiver body 36. In other words, whereas the first and second openings 58, 60 are in communication with a respective one of the liquid and solid waste receiver volumes 62, 64, the lock passageway 90 may not be in communication with the container volume 40. Rather, it is the outer surface 42 that defines the lock passageway 90. The front wall 44 of the receiver body 36 may define an aperture 92, and the rear wall 46 of the receiver body 36 may define another aperture 94 with apertures 92, 94 opening into or at least define a portion of the lock passageway 90 such that the receiver body 36 may surround the lock passageway 90. The lock passageway 90 may be generally centered through the receiver body 36 in a front-to-back direction; however, it is contemplated that the lock passageway 90 may be provided in any suitable pose (i.e., position and orientation). The apertures 92, 94 may be oblong, and the complementary oblong shapes of a lock housing 96 of the locking assembly 34 and the lock passageway 90 facilitate orienting and securing the waste receiver 32 to the locking assembly 34, and thus to the fixed surface, in a single orientation. The lock passageway may extend entirely through the receiver body 36.

Figure 16:
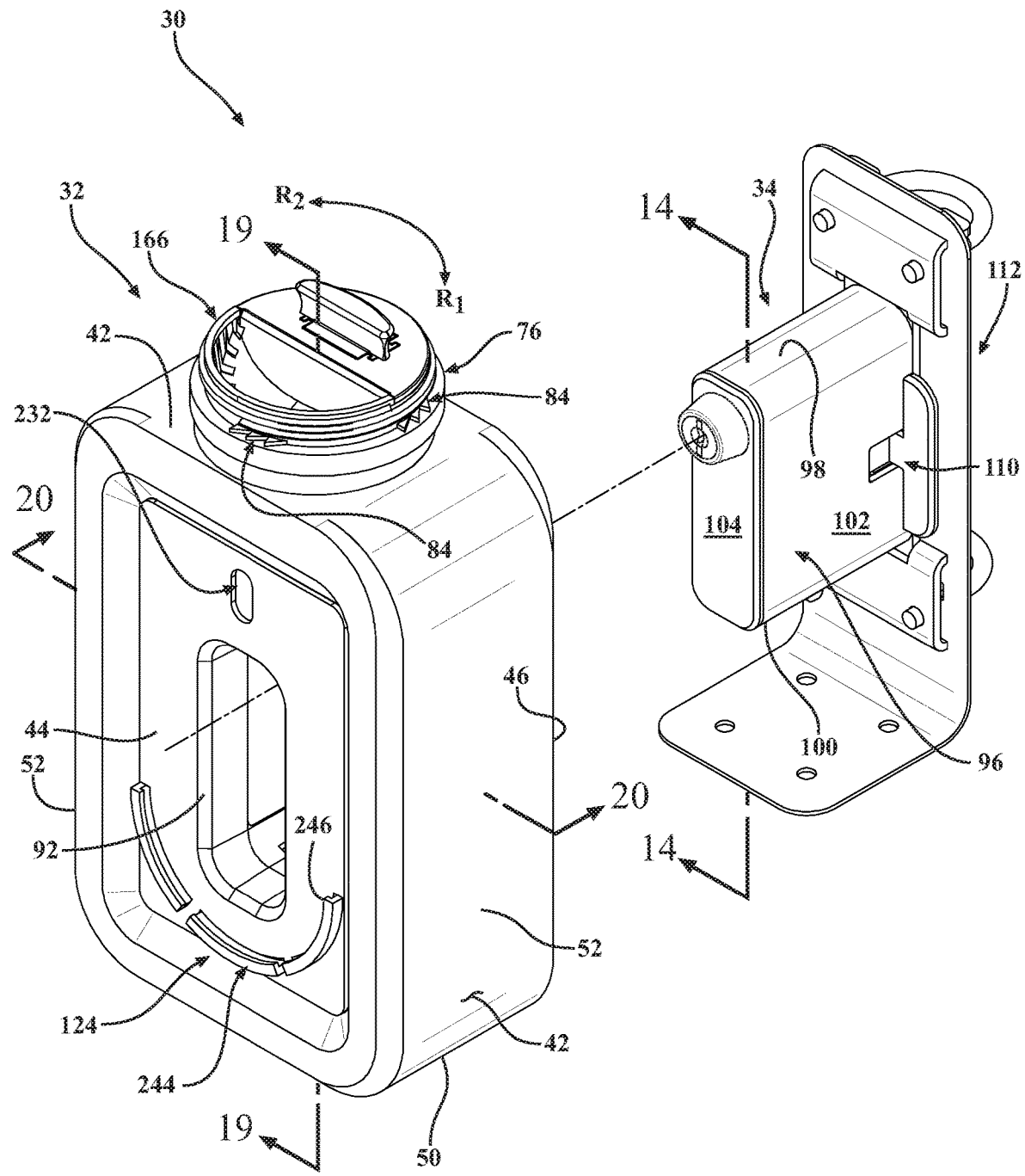
FIG. 16 is a partially exploded front perspective view of the waste disposal system of FIG. 15.
Figure 17:
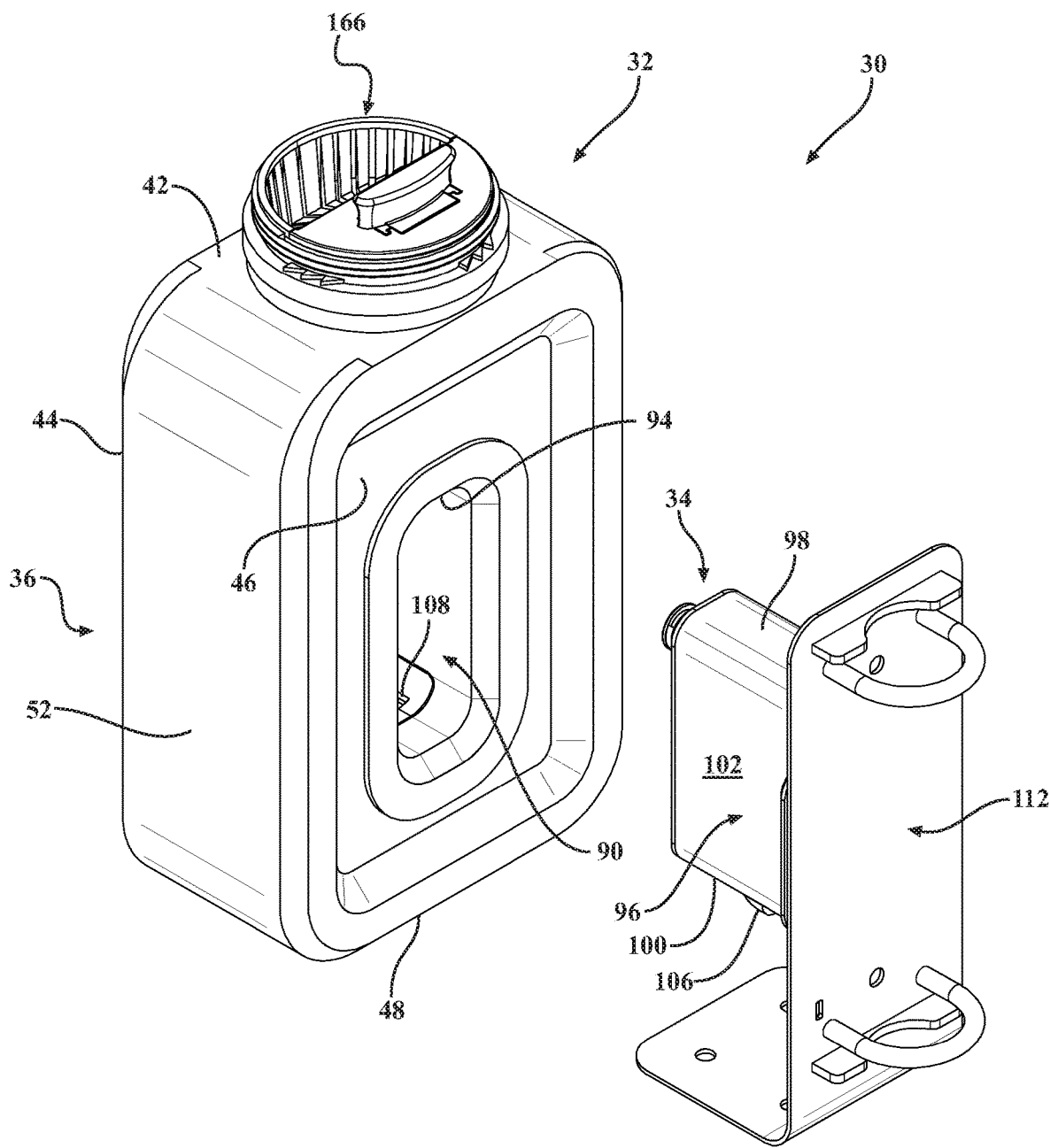
FIG. 17 is a partially exploded rear perspective view of the waste disposal system of FIG. 15.

The locking assembly 34 includes the lock housing 96 sized to be removably positioned at least partially within the lock passageway 90. With reference to FIGS. 3, 16 and 17, the lock housing 96 includes a top wall 98 opposing a bottom wall 100, opposing sidewalls 102 extending between the top and bottom walls 98, 100. A front wall 104 extends between the top, bottom, and opposing sidewalls 98, 80, 102, and the front wall 104 may be oblong corresponding to the apertures 92, 94 that are oblong. The complementary oblong shapes of the lock housing 96 and the lock passageway 90 facilitate orienting and securing the waste receiver 32 to the locking assembly 34, and thus to the fixed surface, in a single orientation. Further, with the waste receiver 32 coupled to the locking assembly 34, the top, bottom, and opposing sidewalls 98, 80, 102 of the lock housing 96 is surrounded in the lock passageway 90 with the front wall 104 positioned near the aperture 92 and accessible to the user for actuating the locking assembly 34 in a manner to be described.

The locking assembly 34 may include an engagement feature 106 movably coupled to the lock housing 96 (see FIG. 17). The receiver body 36 is positioned such that the lock passageway 90 and the lock housing 96 are in alignment, and the engagement feature 106 is at least partially extending through a keyway 108 (see FIGS. 16 and 17) of the receiver body 36 to be described. The waste disposal system 30 may be considered in a locked configuration in which the engagement feature 106 is moved to prevent the waste receiver 32 from being decoupled from the locking assembly 34.

The locking assembly 34 includes the lock cylinder 88. An input to the lock cylinder 88 may actuate the locking assembly 34 between the locked configuration and an unlocked configuration to be described. To facilitate efficient decoupling of the waste receiver 32 from the locking assembly 34, the locking assembly 34 may include a decoupling member 110 coupled to and movable relative to the lock housing 96. The decoupling member 110 is configured to move the waste receiver 32 away from the fixed surface upon the locking assembly 34 entering the unlocked configuration. More particularly, the decoupling member 110 is biased away from a bracket 112 secured to the fixed surface with the decoupling member 110 automatically moving the waste receiver 32 from a first distance from the bracket 112 to a second distance from the bracket 112 greater than the first distance. In the locked configuration, biasing members 114 are resiliently deformed and are prevented from resiliently returning based on the engagement of the engagement feature 106 with the receiver body 36. As the locking assembly 34 is moved from the locked configuration to the unlocked configuration, the disengagement of the protrusion 116 and the keyway 108 no longer prevent the biasing members 114 from moving the decoupling member 110. The biasing members 114 resiliently move the decoupling member 110 and thus the waste receiver 32 to the second distance greater than the first distance.

The cover 82 couples with the receiver body 36 over the opening(s) 34, 35 to seal the pharmaceutical waste material within the container volume 40, and in particular prior to disposal of the waste receiver 32.

With reference to FIG. 6, the cover 80 may include a cover body 118, and a rim 120 defining an outer surface or periphery of the cover body 118. Complementary coupling features 122, for example, teeth 122 disposed on an underside of the cover 82. The teeth 84, 122 are shaped to permit rotation of the cover 82 relative to the receiver body 36 in a single direction. As a result, once it is desired to seal the pharmaceutical waste material within the container volume 40 prior to disposal, the cover 82 is irreversibly coupled with the receiver body 36 with the coupling features 84, 122. After the sealing of the waste receiver 32 by a user with authorization to do so, the pharmaceutical waste material is irretrievable to those within the subsequent chain of custody of the waste receiver 32. As mentioned, the locking feature 86 may be coupled to the rim 120 such that the locking feature 86 extends radially outwardly from the rim 120. The locking feature 86 may be a U-shaped flange configured to receive the lock cylinder 88 of the locking assembly 34 between upstanding ends of the U-shaped flange. The engagement between the locking feature 86 and the lock cylinder 88 prevents rotational decoupling of the cover 82 from the locking assembly 34 when the waste receiver 32 is releasably secured to the locking assembly 34 in the locked configuration to be described.

The waste receiver 32 may include threads near the opening(s) 34, 35 that are configured to receive complementary threads 126 disposed on the underside of the cover 82. The threads may cooperate with complementary coupling features 126 to seal the pharmaceutical waste material within the container volume 40. The waste receiver 32 may include a cover retention feature 124. With particular reference to FIG. 5, the cover retention feature 124 may be coupled to the front wall 44 of the receiver body 36. The cover retention feature 124 may include a boss 126 extending forward from the front wall 44, and threads 128 disposed on an outer surface 130 of the boss 126. FIG. 5 shows a plurality of threads 128 circumferentially spaced about the outer surface 130 of the boss 126. As a result, when the cover 82 threadably coupled to the first cover retention feature 124 prevents axial decoupling of the cover 82 from the receiver body 36. The boss 126 of FIG. 5 may be considered a generally U-shaped protrusion defined between the outer surface 130 and a front surface 132 of the boss 126. A slot 134 defined between opposing sides of the generally U-shaped protrusion is in communication with the lock passageway 90, or stated differently, the lock passageway 90 extends through and is at least partially defined by the boss 126. The cover body 118 may define a concave cavity with a depth at least equal to a length or thickness of a boss 126 extending from the front wall 44 of the receiver body 36. The arrangement permits the cover 82 to be nested in abutment with the front wall 44 of the receiver body 36 such that the locking feature 86 is positioned adjacent the lock passageway 90 when the cover 82 is coupled to the receiver body 36 (and thus permitting engagement of the lock cylinder 88).

Exemplary methods of disposing of the waste receiver 32 may include the waste system 30 initially in the locked configuration, as shown in FIG. 2, with the locking assembly 34 positioned at least partially within the lock passageway 90 of the waste receiver 32. In the locked configuration, the engagement feature 110 of the locking assembly 34 engages the keyway 108 to prevent the waste receiver 32 from being decoupled from the locking assembly 34. The biasing members 114 are in a stored energy state in the locked configuration. Furthermore, the lock cylinder 88 extends forward of the front (e.g., the front wall 44) of the receiver body 36 by a first distance in the locked configuration such that the lock cylinder 88 engages the locking feature 86 of the cover 82. As a result, the cover 82 may not be decoupled from the receiver body 36 in the locked configuration, as rotational decoupling is prevented by the engagement of the lock cylinder 88 and the locking feature 86, and axial decoupling is prevented by the engagement of the cover retention feature 124 (e.g., the threads 128 on the outer surface 130 of the boss 126 and the complementary threads 126 of the cover 82).

The actuating of the locking assembly 34 may include the lock cylinder 88 receives the input from the user, for example, insertion and turning of a key. The engagement feature 106 is moved to disengage from the receiver body 36, more particularly moving out of engagement with the keyway 108. The locking assembly 34 may be considered to be in the unlocked configuration in which the engagement feature 106 has been moved to permit the waste receiver 32 to be decoupled from the locking assembly 34. Moreover, the receiver body 36 is moved away from the fixed surface to disengage the locking assembly 34 from the cover 82. In particular, the decoupling member 110 moves the waste receiver 32 away from the fixed surface once the locking assembly 34 is moved to the unlocked configuration. The magnitude of the movement may be at least greater than an amount that the lock cylinder 88 extends from the front wall 104 of the lock housing 96. The cover retention feature 124 may maintain the coupling between the cover 82 and the receiver body 36 subsequent to the receiver body 36 being moved away from the fixed surface.

Once moving the locking assembly 34 from the locked configuration to the unlocked configuration, the cover 82 may now be considered removably coupled with the cover retention feature 124. Owing to the receiver body 36 being moved away from the fixed surface by a distance greater than the lock cylinder 88, the locking feature 86 of the cover 82 is likewise moved forward of the lock cylinder 88. An input may be provided to the cover 82 to decouple the cover 82 the cover retention feature 124. In one example, the cover 82 is rotated relative to the receiver body 36 in which the threads 126 of the cover 82 are disengaged from the threads 128 of the cover retention feature 124. The step of decoupling the cover 82 from the cover retention feature 124 may be performed while the receiver body 36 is supported on the locking assembly 34 (i.e., the lock housing 96 remains at least partially positioned within the lock passageway 90).

The cover 82 may be coupled with the receiver body 36 over the opening(s) 34, 35 to seal the pharmaceutical waste material within the receiver body 36, and more particularly within the container volume 40. The cover 82 may be coupled to the threads positioned near the opening(s) 34, 35 (also referred to as a second coupling feature). For example, the threads near the opening(s) 34, 35 are threadably engaged with complementary threads 126 of the cover 82. Further, the coupling features 122 of the cover 82 engage the coupling features 84 to irreversibly couple the cover 82 with the receiver body 36. The step of coupling the cover 82 from the second cover retention feature 124 may be performed while the receiver body 36 is supported on the locking assembly 34 (i.e., the lock housing 96 remains at least partially positioned within the lock passageway 90). The waste receiver 32 may be removed from the locking assembly 34, and the waste receiver 32 may be disposed of in a suitable manner.

Exemplary methods may further include providing a second waste receiver, which may be the same or similar to the waste receiver 32 previously removed. As such, the second waste receiver includes a second cover and a second receiver body defining a second lock passageway. The lock housing 96 may be positioned within the second lock passageway to couple the second receiver body and the locking assembly 34 such that the engagement feature 106 engages the second receiver body. The second cover may be coupled to the second receiver body prior to and during the step of positioning the lock housing 96 within the second lock passageway. The locking assembly 34 may be actuated from the unlocked configuration to the locked configuration in manners previously described, which concurrently secures the second cover to the second receiver body. The second waste receiver is readied for operational duty.

As mentioned, the waste receiver 32 may advantageously accommodate disposal of both the solid phase pharmaceutical waste material in the solid waste receiver volume 62 and the liquid phase pharmaceutical waste material in a liquid waste receiver volume 64. The solid and liquid waste receiver volumes 62, 64 may be disposed in the single receiver body 36. The first and second openings 58, 60 may be defined by the singular, circular neck 76, and be in communication with a respective one of the liquid and solid waste receiver volumes 62, 64. Owing to the appearance of the funnel-type device, it is readily apparent to the user to dispose of the liquid phase pharmaceutical waste material through the first opening 58 and into the liquid waste volume 64 for suitable treatment. Likewise, the shape of the second opening 60 and the pushing member 78 disposed therein makes it readily apparent the user to dispose of the solid phase pharmaceutical waste material through the second opening 60 and into the solid waste receiver volume 62 for suitable treatment. While two openings 58, 60 are shown, it is contemplated that a single opening may be provided, or more than two opening may be provided. For example, the neck 76 of the receiver body 36 may define a single opening with barriers or other structures configured to divert each phase of the pharmaceutical waste material to its respective waste volume 62, 64 for suitable treatment. In order to properly render the pharmaceutical waste material irretrievable and/or unrecoverable, each of the solid phase pharmaceutical waste material and the liquid phase pharmaceutical waste material should undergo treatment specific to its phase. Less sophisticated systems with a single vessel simply commingle the liquid and solid phase pharmaceutical waste material with each being treated sub-optimally, thereby increasing the likelihood of retrieval, recovery, and diversion.

Figure 7:
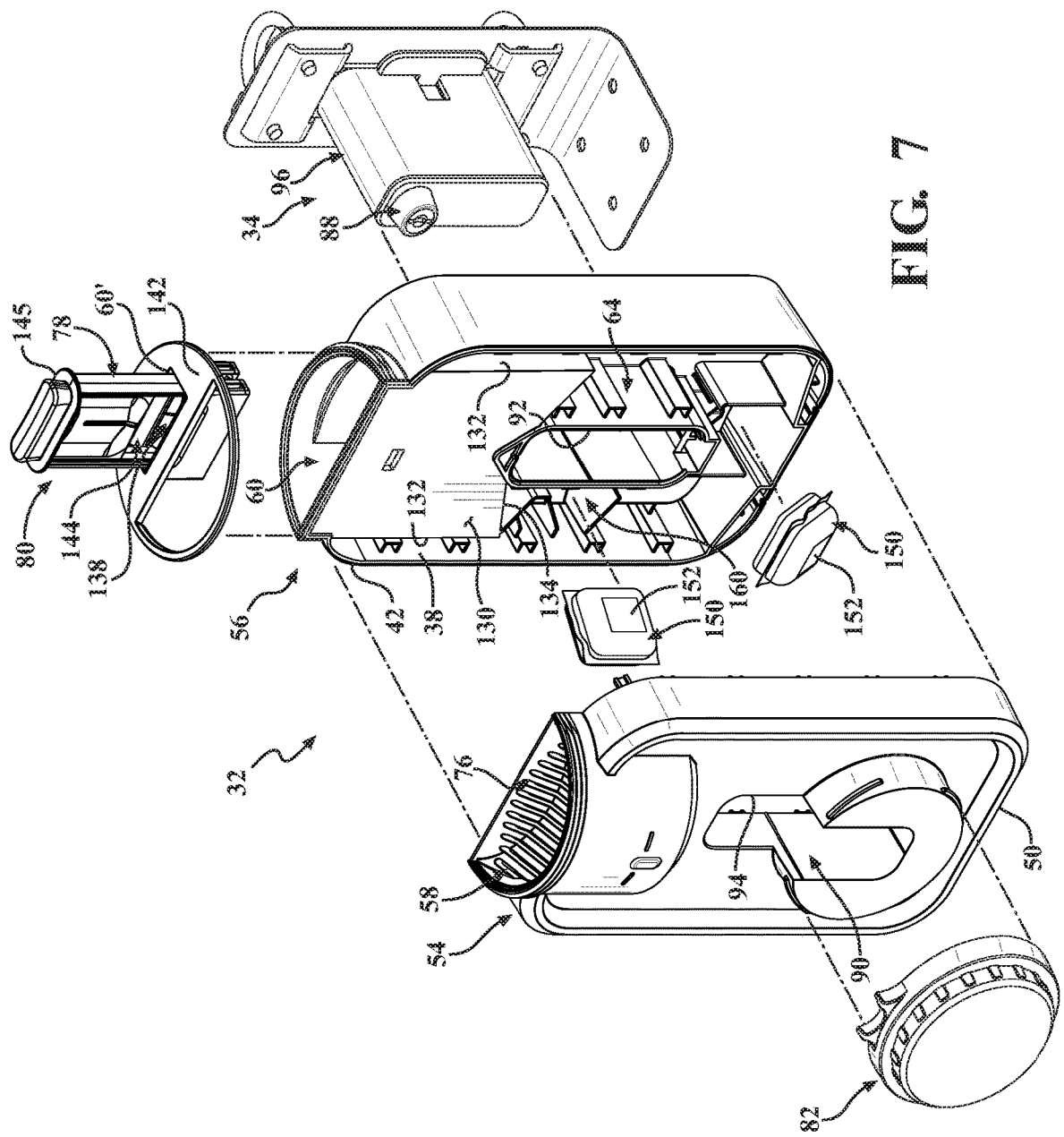
FIG. 7 is a partially exploded view of the waste disposal system.

The liquid waste receiver volume 64 may be collectively defined by two shells 54, 56 joined together to form the receiver body 36, as best shown in FIGS. 7 and 11. In other words, each of the shells 54, 56 may include a cavity defining a portion of the liquid waste receiver volume 62 of the container volume 40. Each of the shells 54, 56 may also cooperate to define the lock passageway 90 and the neck 76.

Figure 8:
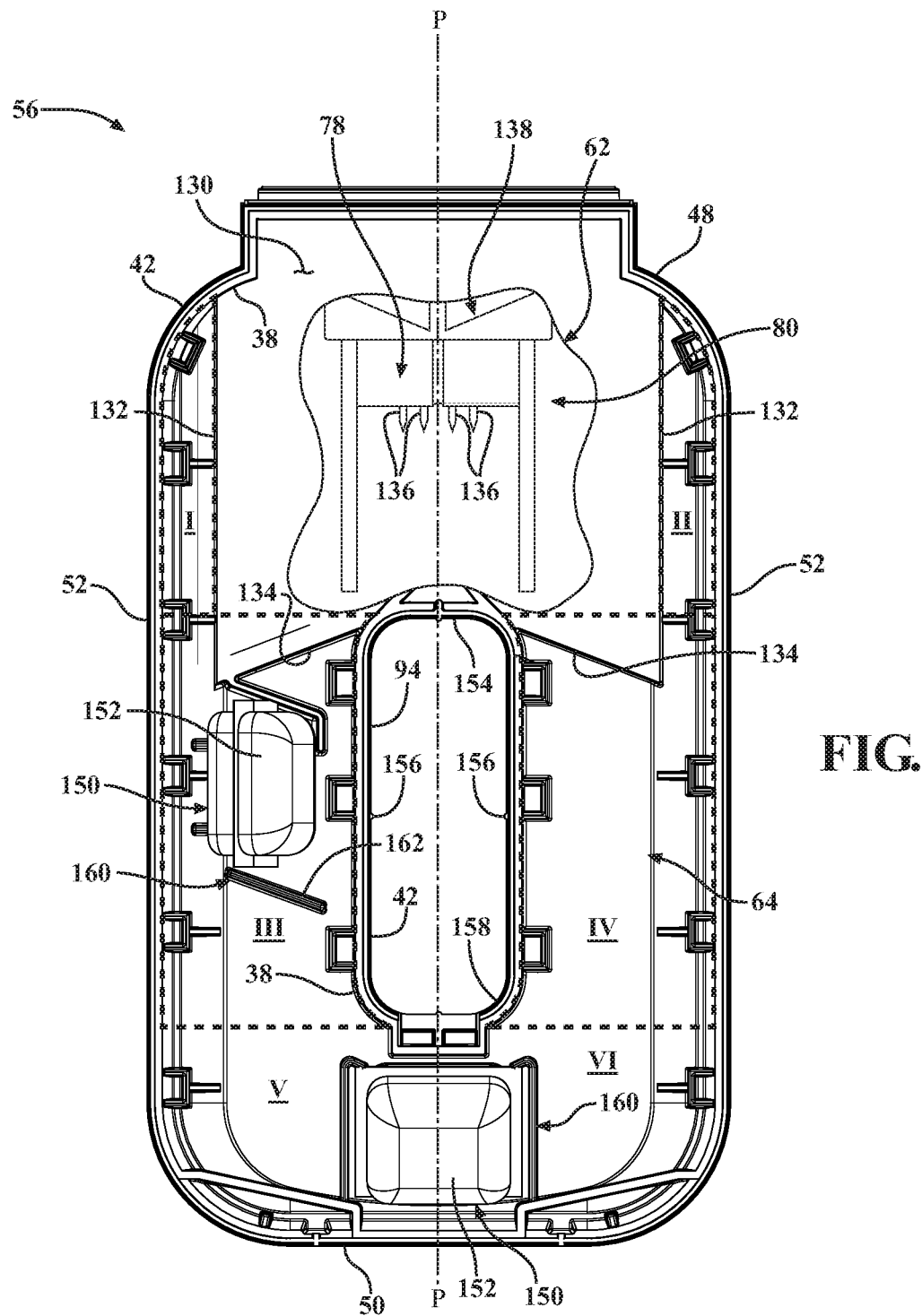
FIG. 8 is a front elevation view of a rear shell of the waste receiver with a cutaway showing a portion of the solid waste receiver volume and certain components disposed therein.
Figure 12:
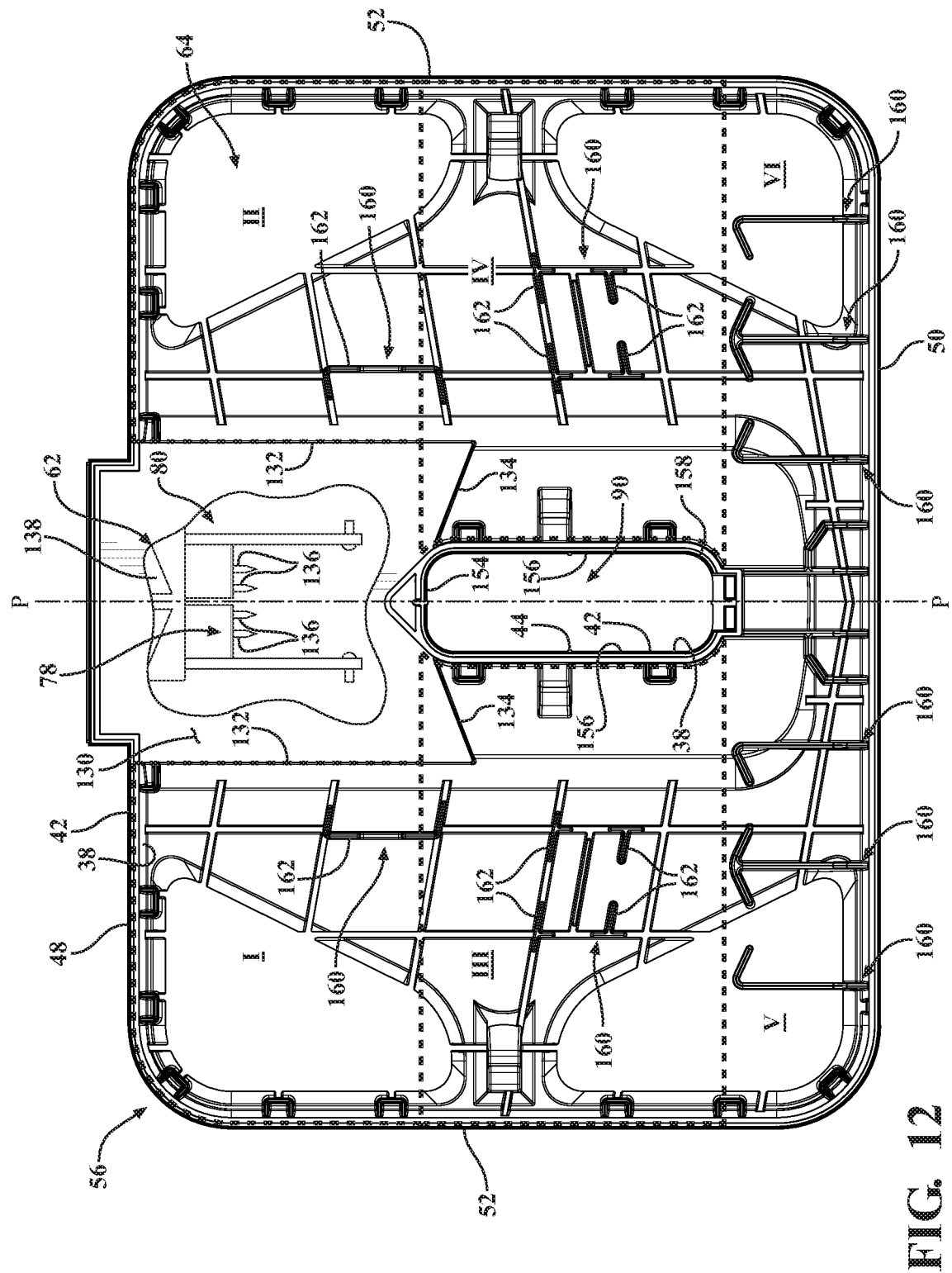
FIG. 12 is a front elevation view of a rear shell of the waste receiver of FIG. 10 with a cutaway showing a portion of the solid waste receiver volume and certain components disposed therein.

The solid waste receiver volume 62 may be defined by a singular shell 56 of the two shells 54, 56. FIGS. 8 and 12 show partitions 130, 132, 134 collectively defining the solid waste receiver volume 62 with the rear wall 44 of the receiver body 36. In particular, the partitions 130, 132, 134 may be arranged to effectively define the solid waste receiver volume 62 that is substantially fluidly separate from the liquid waste receiver volume 64. Because the solid waste receiver volume 62 is effectively fully contained within only the singular shell 56, the receiver body 36 may be more easily fabricated as the separate shells 54, 56 with manufacturing techniques such as injection molding or the like. However, it is contemplated that the shells 54, 56 may collectively define the solid waste receiver volume 62 when joined together. In such an arrangement, a fluid-tight seal may be indicated and, as mentioned, a liquid may be added to the solid waste receiver volume 62 with the priming aide 68 to prime the solid waste receiver volume 62 prior to use.

The solid waste receiver volume 62 may be relatively smaller than the liquid waste receiver volume 64. It is appreciated that in certain service locations, upwards of 90% of the pharmaceutical waste material is liquid in phase. For this reason, the liquid waste receiver volume 64 may comprise 60%, 70%, 80% or 90% or greater of the container volume 40 of the receiver body 36. For example, the liquid waste receiver volume 64 may have a capacity of approximately 0.5, 1.0, or 1.5 or greater liters (L), and the solid waste receiver volume 62 may have a capacity of approximately 0.2, 0.4, 0.6 or greater liters. It is understood that the relative portions between the solid and liquid waste receiver volumes 62, 64 are merely exemplary, and the relative volume of the solid and liquid waste receiver volumes 62, 64 may vary based on the application. Furthermore, it is recognized that the size and/or capacity of the waste receiver 32 may be commensurate with the purpose and/or service location of the waste disposal system 30.

With reference to FIGS. 7, 8, 11 and 12, a solid receiver guide 80 directs the solid phase pharmaceutical waste material to the solid waste receiver volume 62, as mentioned, and more particularly in a manner that facilitates the solid phase pharmaceutical waste material being irretrievable and/or unrecoverable. The solid receiver guide 80 may include the inlet 60', a pushing member 78, a gripping member 136, a funnel member 138, and a cutting element 140 (see FIGS. 7, 11, 19 and 21-23). The solid receiver guide 80 may include a cover 142 sized to be disposed within the second opening 60. The cover 142 may include a D-ring such that the cover 142 has a generally circular periphery shaped to the neck 76 of the receiver body 36. The D-ring may be disposed about the first opening 58, as generally appreciated from FIGS. 7 and 11. The cover 142 defines the inlet 60'.

The solid receiver guide 80 is be described in greater detail in relation to the embodiment of FIGS. 16-21 including the diverter 166, but the function of the pushing member 78, the gripping member 136, the funnel member 138 will be briefly introduced here. The pushing member 78 is movably disposed within the inlet 60', and within the solid waste receiver volume 62. The pushing member 78 is adapted to receive an input from a user to move the solid phase pharmaceutical waste material through the solid receiver guide 80. The pushing member 78 is movable between a first position in which a main body of the pushing member 78 is spaced above the inlet 60' to provide a window 144 for receiving the solid phase pharmaceutical waste material (see FIGS. 7 and 11), and a second position in which the window 144 is not present and a handle 145 may be flush with the cover 142 (see FIG. 2). For example, moving the pushing member 78 from the second position to the first position may include moving the handle 145 away from the cover 142 to provide the window 144, and moving the pushing member 78 from the first position to the second position may include moving the handle 145 towards from the cover 142.

As previously mentioned, solid phase pharmaceutical waste material of particular interest are patches and pills, and the waste receiver 32 may include the cutting element disposed within the solid waste receiver volume 62 and positioned to cut the solid phase pharmaceutical waste material. In particular, the cutting element is adapted to at least score a patch or a pill upon insertion of the patch or the pill through the solid receiver guide 80. With the pushing member 78 in the second position, the patch may be positioned within the window 144. The pushing member 78 is moved from the second position to the first position, and the cutting element at least scores the solid phase pharmaceutical waste material. The gripping member 136 may be coupled to the pushing member 78 and adapted to engage and avoid inadvertent ejection of the patch. For example, the gripping member 136 may be four spikes tapering to a point configured to penetratingly engage the patch typically comprised of a woven fabric or permeable layer.

Figure 25:
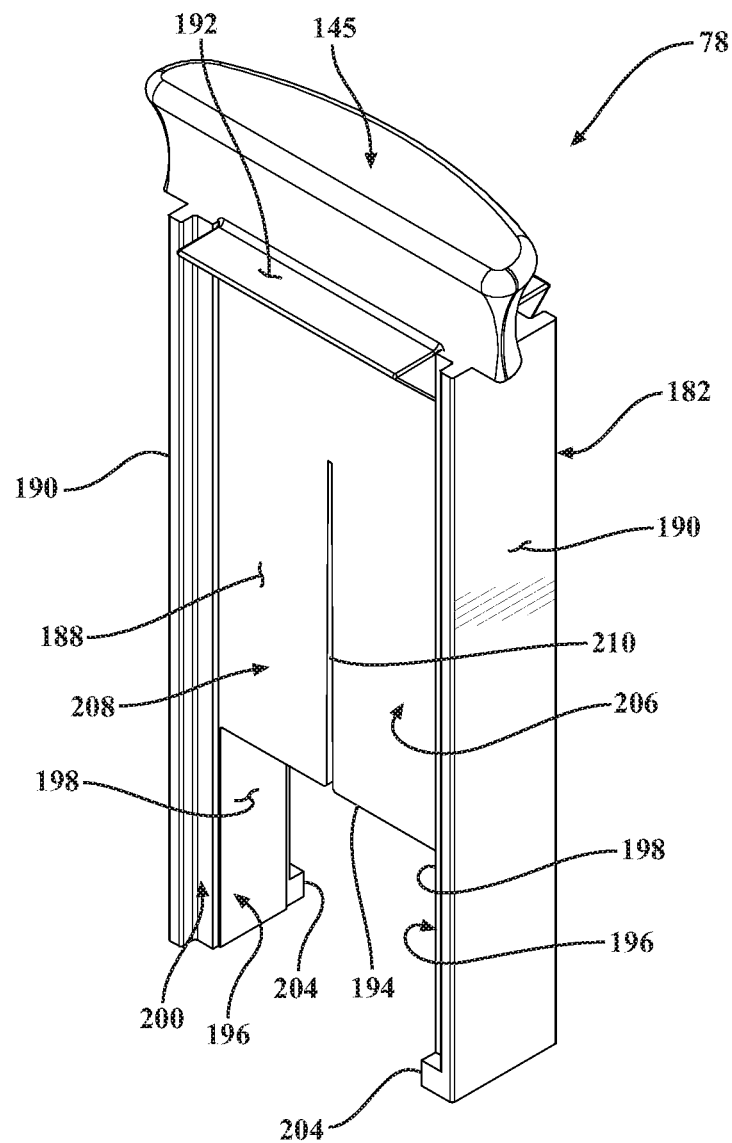
FIG. 25 is a perspective view of a pushing member.
Figure 26:
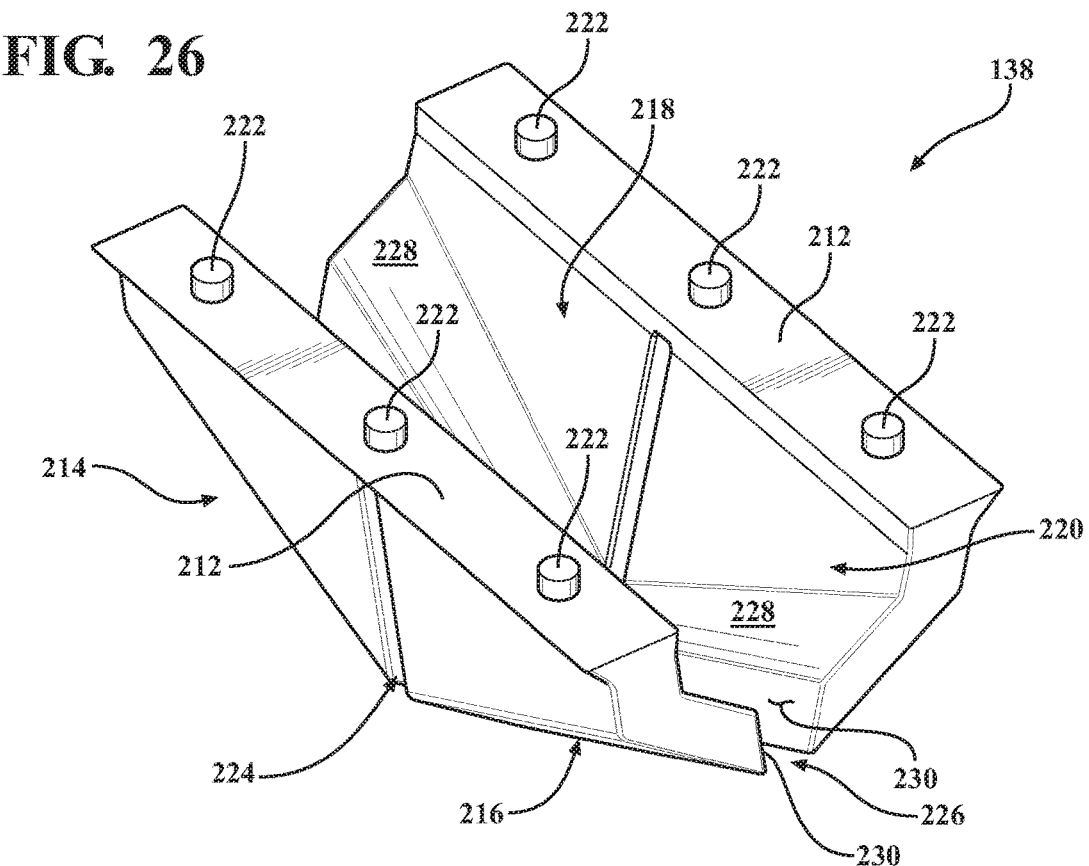
FIG. 26 is a perspective view of a funnel member.

The scoring of pills is associated with additional challenges based on their size and shape, and the funnel member 138, best shown and described in relation to FIGS. 25 and 26, may be disposed in the solid waste receiver volume 62 between the inlet and the cutting element to increase the likelihood that the solid phase pharmaceutical waste material being moved through the solid receiver guide 80 properly encounters the edge of the cutting element. The funnel member 138 includes at least one gap that may be sized at least slightly smaller than at least some pills such that the pill(s) deposited through the inlet 60' are supported until urged through the gap with the pushing member 78. At least one of the gaps may be positioned above the cutting element such that the cutting element at least partially scores the pill, which then further descends within the solid waste volume 62 under the influence of gravity. With the pill suitably scored and perhaps sliced, the fluid within the solid waste volume 62 more likely comes into contact with the active medicine of the pill (i.e., beneath the coating, within the capsule, etc.).

Figure 13:
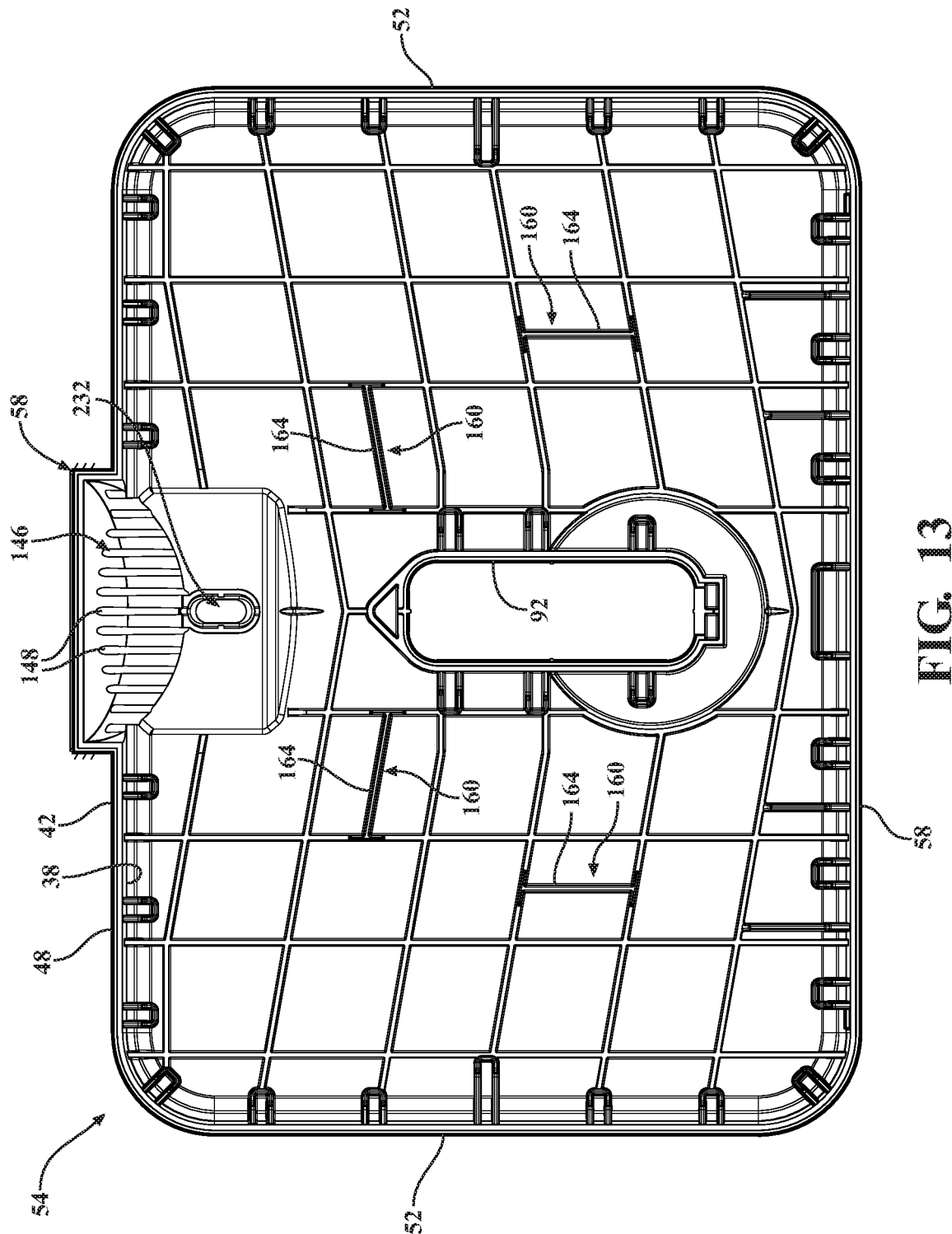
FIG. 13 is a rear elevation view of a front shell of the waste receiver of FIG. 10.
Figure 14:
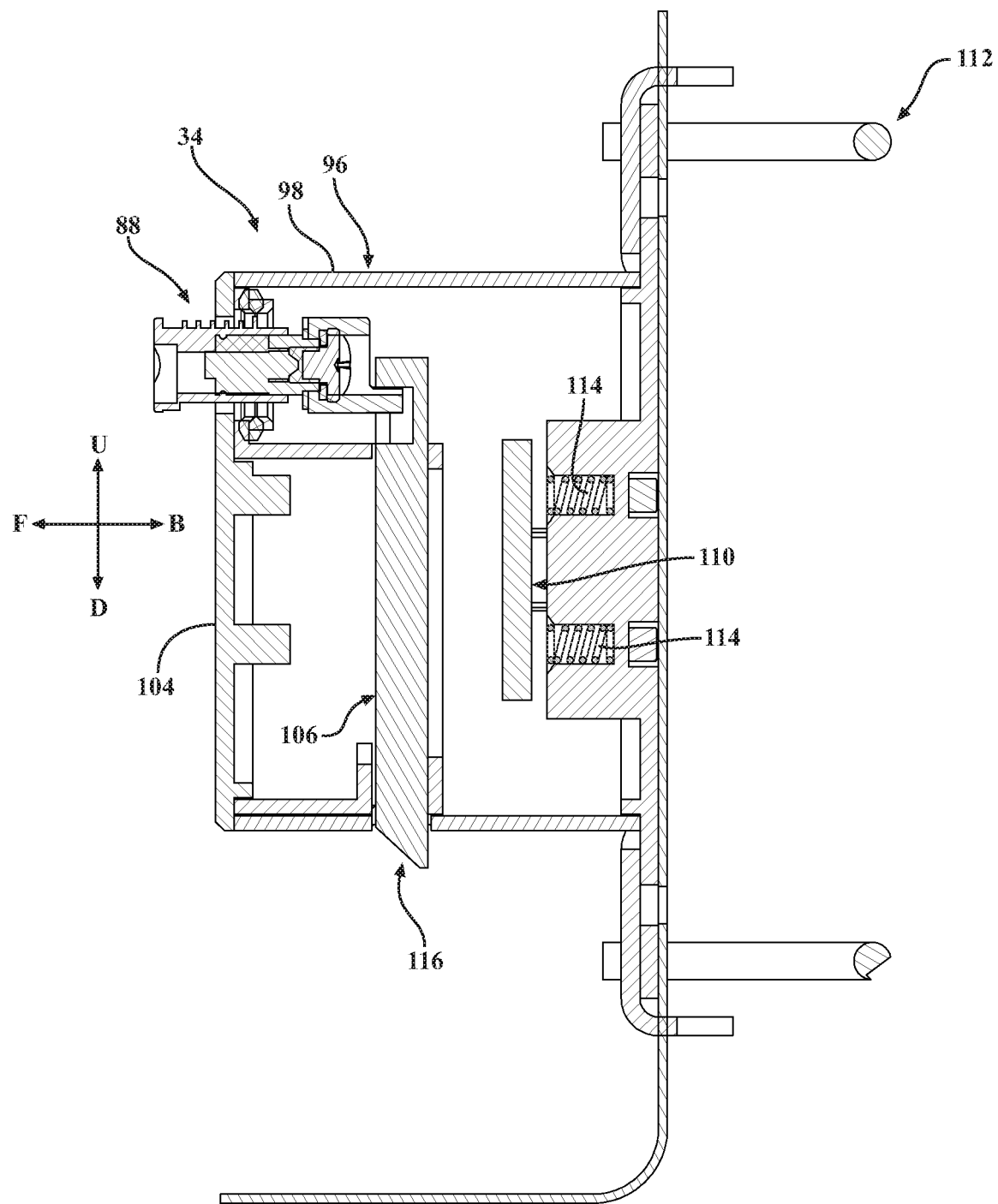
FIG. 14 is a sectional elevation view of the locking assembly.

The liquid waste receiver volume 64 will now be described with reference to FIGS. 7-12. FIGS. 8 and 12 show a front elevation view of the interior of the rear shell 56 and FIGS. 9 and 13 show a rear elevation view of the interior of the front shell 54. The first opening 58 is in communication with the liquid waste receiver volume 64. A funnel-type liquid receiver guide 146 may be provided to define the first opening 58 and includes at least one orifice 148 for the liquid phase pharmaceutical waste material to pass through to the liquid waste receiver volume 64. The orifices 148 are sized to not only to inhibit or prevent retrieval of the liquid phase pharmaceutical waste material from within the liquid waste receiver volume 64 by impeding tools from entering the liquid waste receiver volume 64, but also impede ingress of the solid phase pharmaceutical waste material to the liquid waste receiver volume 64.

The waste disposal system 30 may include a reaction agent 150 or chemical composition disposed within the waste receiver 32 for limiting the recoverability of the pharmaceutical waste material. The chemical composition may include at least one of a fluid absorber suitable for absorbing and retaining large amounts of fluid, and a reaction agent. The fluid absorber may be the superabsorbent polymer (SAP) that absorbs the liquid phase pharmaceutical waste material deposited to the waste receiver 32 such that the liquid phase pharmaceutical waste material is not readily recoverable and/or retrievable from the liquid waste receiver volume 64. By way of non-limiting example, the SAP may be a polyacrylic acid salt-based polymer, a vinyl alcohol-acrylic acid salt-based polymer, a PVA based polymer, an isobutylene-maleic anhydride polymer, a polysaccharide based polymer such as carboxymethyl starch, carboxymethyl cellulose, and hydroxypropyl cellulose, nonionic based polymers such as polyvinyl alcohol and polyvinyl ethers, a cationic based polymer such as polyvinyl pyridine, polyvinyl morpholinione, and N,N-dimethylaminoethyl or N,N-diethylaminopropyl acrylates and methacrylates, a carboxy group based polymer such as hydrolyzed starch-acrylonitrile graft copolymers, partially neutralized hydrolyzed starch-acrylonitrile graft copolymers, hydrolyzed acrylonitrile or acrylamide copolymers and polyacrylic acids, and combinations thereof.

The reaction agent 150 may be any agent suitable for limiting the recoverability of pharmaceutical waste material. The reaction agent 150 may include a bittering agent, an emetic, a denaturant, an ionization agent, an oxidizing agent, a catalyzing agent, an anti-fungal agent, a viscosity modifier, activated charcoal, and combinations thereof. The reaction agent 150 may chemically and/or physically alter, break down, deactivate, denature, or otherwise change the pharmaceutical waste material deposited within the waste receiver 32 such that the pharmaceutical waste material is not readily recoverable and/or retrievable from the liquid waste receiver volume 64. In the context of this disclosure, the term denature means to prevent use or reclamation of waste drugs, or to deter use through agents, and/or to provide interference, expense, time, and complex procedures thereby making recovery for human consumption or use prohibitive, impractical, highly inefficient, and/or to render the waste drug biologically inactive. The term unrecoverable means that the pharmaceutical waste material has been chemically or physically altered and/or deactivated such that the pharmaceutical waste material is no longer usable to provide its previous function, to perform its previous purpose, and/or to make the pharmaceutical waste material not useful for human consumption.

The bittering agent may be any type of bittering agent suitable to render the pharmaceutical waste material unpalatable in taste, for example, denatonium benzoate. The emetic may be any type of emetic suitable to induce vomiting upon ingestion, for example, may be Ipecac, mustard powder, and combinations thereof. The denaturant may be, for example, quinine sulfate dehydrate, rucine (or brucine sulfate), nicotine, cinchonidine (or cinchonidine sulfate), 2-hydroxymethyl ether, 2-(hydroxymethyl) amino ethanol, ammonium hydroxide, sodium hydroxide, denatonium benzoate, quassin, naringin, sodium chloride, sodium carbonate, ferrous sulfate, edifas B, sodium carboxymethyl cellulose, carboxymethyl ether, chlorine dioxide, chlorine, bromine, sodium bicarbonate, formamide (deionized), guanidine thiocyanate, guanidine isothiocyanate, sodium dodecyl sulfate (SDS), formamide, guanidine hydrochloride, guanidine isothiocyanate solution, urea, thiourea, guanidinium chloride, dihydrofolate reductase, calcium sulfate dihydrate, Cole-Parmer quinine, Cole-Parmer 2-ketoglutaric acid, Cole-Parmer tetramethyltin, 2-ketoglutaric acid, cerium sulfate, quercetin dihydrate, oxalic acid dihydrate, lithium sulfate, (+)-(R)-trans-4-(1-Aminoethyl)-N-(4-pyridyl) cyclohexanecarboxamide dihydrochloride, (+/−)-1-(5-Isoquinolinesulfonyl)-2-methylpiperazine dihydrochloride, (+/−)-3-Aminopyrrolidine dihydrochloride, (+/−)-trans-4-(2-Pyridinyl)-pyrrolidine-3-carboxylic acid dihydrochloride, (+/−)-trans-4-(4-Pyridinyl)-pyrrolidine-3-carboxylic acid dihydrochloride, (−)-N-(1(R)-Phenylethyl)-1-azabicyclo[2.2.2]octan-3(S)-amine dihydrochloride, (1,4-Dimethylpiperazin-2-yl)acetic aciddihydrochloride, (1-(5-Isoquinolinesulfonyl)-homopiperazine dihydrochloride, (1-Aza-bicyclo[2.2.2]oct-3-yl)-(4-fluoro-benzyl)-amine dihydrochloride, (1-Aza-bicyclo[2.2.2]oct-3-yl)-(4-methoxy-benzyl)-amine dihydrochloride, (1-Methyl-1H-benzimidazol-2-yl)methylamine dihydrochloride, (1-Methyl-piperidin-4-yl)-pyridin-3-ylmethylamine-dihydrochloride, (1-[1,3]Oxazolo[4,5-b]pyridin-2-ylpyrrolidin-3-yl)methylamine dihydrochloride: (1H-Imidazol-2-yl) methanamine dihydrochloride, (1R,2R)-trans-1,2-Cyclopentanediamine dihydrochloride, (1S,2S)-1,2-bis(2,4,6-trimethylphenyl)ethylenediamine dihydrochloride hydrate, (1S,2S)-1,2-bis(2-Chlorophenyl)ethylenediamine dihydrochloride, (1S,2S)-1,2-bis(4-Fluorophenyl)ethylenediamine dihydrochloride: (1S,2S)-1,2-Bis(4-methoxyphenyl)ethylenediamine dihydrochloride, (1S,2S)-1,2-bis(4-Nitrophenyl)ethylenediamine dihydrochloride, (1S,2S)-1,2-di-1-naphthylethylenediamine dihydrochloride, (1S,2S)-trans-1,2-Cyclopentanediamine dihydrochloride, (1S,4S)-5-Methyl-2,5-diazabicyclo[2.2.1]heptane dihydrochloride, (2,4-Dimethyl-1,3-thiazol-5-yl)methylaminedihydrochloride, (2-Amino-benzothiazol-8-yl)-acetic acid dihydrochloride, (2-Chloro-6-fluorobenzyl)hydrazine dihydrochloride, (2-Dimethylaminoethyl)-reserpilinate dihydrochloride, (2-Ethyl-1,4-diazepan-1-yl)methanoldihydrochloride, (2-Imidazol-1-ylethyl)methylamine dihydrochloride, (2-Imino-thiazol-3-yl)acetic acid dihydrochloride, and combinations thereof. The oxidizing agent may be, for example, a chlorine-based oxidizing agent, a non-chlorine-based oxidizing agent, and combinations thereof. Further non-limiting examples of the chlorine-based oxidizing agent may be sodium hypochlorite, magnesium hypochlorite, calcium hypochlorite, sodium dichloroisocyanurate dihydrate, or any other stable solid chlorine compounds and salts thereof. The chlorine-based oxidizing agent may be sodium dichloroisocyanurate dehydrate. The chlorine-based oxidizing may be in solid form and may be shelf-stable. Further examples of the non-chlorine-based oxidizing agent may be bromine-based oxidizing agents, stabilized peroxide compounds such as persulfate, permonosulfate, permanganate, and other stabilized peroxide compounds and salts thereof, and metal oxides.

The reaction agent 150 may consist, comprise, or consists essentially of, the SAP and the chlorine-based oxidizing agent. When the composition comprises the SAP and the chlorine-based oxidizing agent, the SAP may be present in an amount of at least 85, at least 90, or at least 95, percentage by weight (wt. %) based on the total weight of the composition. Even more particularly, the SAP may be present in an amount of 96, 97, or 98, wt. % based on total weight of the composition, and the chlorine-based oxidizing agent may be present in an amount of less than 15, less than 10, less than 5, less than 2.5, or less than 1 wt. % based on the total weight of the composition. The reaction agent may include quinine sulfate dehydrate in an amount of from 40 to 100 wt. % based on the total weight of the reaction agent, Ipecac in an amount of from 0 to 60 wt. % based on the total weight of the reaction agent, and denatonium benzoate in an amount of from 0 to 15 wt. % based on the total weight of the reaction agent.

Referring again to FIGS. 7 and 11, the reaction agent 150 may be disposed in a packet 152. The packet 152 may include a film capable of being dissolved by water. In this manner, the addition of liquid phase pharmaceutical waste material and/or water to the liquid waste receiver volume 64 solubilizes the film thereby releasing the reaction agent 150. The film may include a water-soluble polymer, for examples, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, starch, high amylose starch, hydroxypropylated high amylose starch, dextrin, pectin, chitin, chitosan, levan, elsinan, collagen, gelatin, zein, gluten, soy protein isolate, whey protein isolate, casein and combinations thereof. The film may include polyvinyl alcohol. The packet 152 may be fluid permeable, and include a screen material, a mesh material, or the like. It is contemplated that the packet 152 may further assume configurations capable of releasing the reaction agent 150 upon an occurrence of a triggering event, such as an elapsed period of time, contact with a specific type of material, and the like.

The reaction agent 150, for example, the packet 152, may be positioned in select locations within the liquid waste receiver volume 64. Referring now to FIGS. 8 and 12, for purposes of convention, the liquid waste receiver volume 64 may be divided into Regions I-VI. A vertical plane P may bifurcate the rear shell 56 (and the receiver body 32), and the structures of the rear shell 56 may be generally symmetric about the plane P. Regions I and II may be spaced apart from the bottom wall 50 and separated on opposing sides of the solid waste receiver volume 62, and Regions III and IV may be spaced apart from the bottom wall 50 and separated on opposing sides of the lock passageway 90. More specifically and as demarcated by dashed lines in FIGS. 8 and 12, Region I may be bounded by the inner surface 38 of the upper wall 48, the inner surface 38 of one of the sidewalls 52, one of the partitions 132 at least partially defining the solid waste receiver volume 62, and a horizontal plane extending from or intersecting an upper aspect 154 of the lock passageway 90. Region II may be bounded by the inner surface 38 of the upper wall 48, the inner surface 38 of the other sidewalls 52, the other partition 132 at least partially defining the solid waste receiver volume 62, and the horizontal plane extending from or intersecting an upper aspect 154 of the lock passageway 90. Region III may be bounded by the horizontal plane extending from or intersecting an upper aspect 154 of the lock passageway 90, the inner surface 38 of one of the sidewalls 52, the inner surface 38 of one of the lateral aspects 156 of the lock passageway 90, and a horizontal plane extending from or intersecting a lower aspect 154 of the lock passageway 90. Region IV may be bounded by the horizontal plane extending from or intersecting an upper aspect 154 of the lock passageway 90, the inner surface 38 of the other one of the sidewalls 52, the inner surface 38 of the other ones of the lateral aspects 156 of the lock passageway 90, and the horizontal plane extending from or intersecting a lower aspect 154 of the lock passageway 90. Region V may be bounded by the horizontal plane extending from or intersecting a lower aspect 158 of the lock passageway 90, the inner surface 38 of one of the sidewalls 52, the plane P, and the inner surface 38 of the bottom wall 50. Region VI may be bounded by the horizontal plane extending from or intersecting the lower aspect 158 of the lock passageway 90, the inner surface 38 of the other one of the sidewalls 52, the inner surface 38 of the other ones of the lateral aspects 156 of the lock passageway 90, and the horizontal plane extending from or intersecting a lower aspect 154 of the lock passageway 90.

The reaction agent 150 may be positioned within a region of the container volume defined between the lock passageway 90 and the opposing sidewalls 52 of the receiver body 36. In the aforementioned convention, for example, the packet 152 may be disposed in Regions II or III, as generally appreciated from FIGS. 7, 8 and 11, such that the reaction agent 150 is positioned to be spaced apart from the bottom wall 50. The spacing of the reaction agent 150 from the bottom wall 50 advantageously prevents premature or incomplete reacting of the reaction agent 150 with the incoming liquid phase pharmaceutical waste material. In other words, having packets 152 spaced apart from the bottom wall 50 may provide for staged reactions or absorption with the incoming liquid phase pharmaceutical waste material as the liquid waste receiver volume 40 is filled with the liquid phase pharmaceutical waste material. Owing to the relatively greater container volume 40 of the waste receiver of FIG. 12, the packets 152 may be disposed on both sides of the lock passageway 90 and spaced apart from the bottom wall 50.

The waste receiver 32 may include supports 160 coupled to at least one of the shells 54, 56. The supports 160 are configured to maintain a position of the reaction agent 150 within the liquid waste receiver volume 64. FIGS. 7, 8, 11 and 12 show one the supports 160 positioned between the lock passageway 90 and one of the sidewalls 52, and another one of the supports 160 positioned between the lock passageway 90 and the other one of the sidewalls 52. The supports 160 may include a plurality of projections 162 extending from the inner surface 38 of one of the shells 54, 56. The projections 162 may be spaced apart from one another to collectively define a cage. The cage is sized to receive the reaction agent 150, for example, the packet 152, and suspend the packet 152 within the liquid waste receiver volume 64. In other words, the projections 162 may prevent more than minimal movement of the reaction agent 150.

The reaction agent 150 may be positioned between the solid waste receiver volume 62 and at least one of the two sidewalls 52. In other words, the reaction agent 150 may be positioned within Region I and/or Region II. Moreover, the reaction agent 150 may be positioned within Region V and/or Region VI. The reaction agent 150 in Regions V or VI may or may not be spaced apart from the bottom wall 50. FIG. 11 generally reflects one packet 152 in each of Regions I-IV and two packets 152 in each of Regions V and VI. However, other suitable arrangements are contemplated. For example, there may be two, three or four or more packets 152 each of Regions I-IV. FIG. 8 shows the reaction agent 150 positioned within Region III and spaced apart from the bottom wall 50, and another reaction agent 150 positioned within Regions V and VI and not spaced apart from the bottom wall 50.

Numerous alternatives for arranging the chemical composition within the liquid waste receiver volume 64 are contemplated, including those introduced later in the present disclosure and those described in co-owned U.S. Pat. Nos. 8,132,056; 8,534,459; 8,573,426; 8,616,397; 9,044,377; 9,456,954, and co-owned United States Patent Publication No. 2016/0325322, the contents of each being hereby incorporated by reference in its entirety. The volume of the chemical composition disposed within the packet may be any volume suitable for rendering the pharmaceutical waste material within the waste receiver 32 less recoverable and/or retrievable from the liquid waste receiver volume 64. The volume of the chemical composition disposed within the packet may be based on the volume of the waste receiver 32.

FIGS. 7 and 11 shows the projections 162 extending from the inner surface 38 of the rear shell 56. FIGS. 8 and 12 shows projections 164 extending from the inner surface 38 of the front shell 54. The projections 162 of the front shell 54 are arranged to cooperate with the projections 162 of the rear shell 56 to support the packet 152 to be spaced apart from the bottom wall 50. The projections 162, 164 may be integrally formed with a respective one of the shells 54, 56 through, for example, injection molding. The integral forming of the projections 162, 164 defining the support 160 advantageously provide for easier manufacturing and reduced cost relative to a separate support-type component to be coupled to the receiver body 36 in the appropriate position(s). Further, because part of the purpose of the waste receiver 32 is to prevent access to the container volume 40, and even if meaningful access to the container volume 40 was achievable prior to completing assembly of the waste receiver 32, the presence of the lock passageway 90 may make accessing the desired positioning of the packets 152 to be especially difficult. Thus, inserting the packets 152 in the manner described and forming the receiver body 36 through the two shells 54, 56 may be particularly well suited.

The two shells 54, 56 of the receiver body 36 advantageously provide for improved assembly of the waste receiver 32. In particular, the solid waste receiver volume 62 may be contained within a singular one 56 of the shells 54, 56, thereby simplifying construction of the receiver body 36. Further, the integral forming of the projections 162, 164 provide for simplified construction of the supports 160. With the two shells 54, 56 separated as shown, the reaction agent 150 may be positioned to be supported by the support 160. For example, the packet 152 may be placed between the projections 162 defining the cage. The two shells 54, 56 may be joined to form the receiver body 36 through a suitable joining process, for example, thermal, ultrasonic, radio-frequency or laser welding, adhesive, fasteners, or the like. The projections 164 on the front shell 54 effectively sandwich the reaction agent 150 to prevent movement of the packet 152 in two directions (i.e., front and back), and the projections 162 defining the cage prevent movement of the packet 152 in four directions (i.e., up, down, and bilaterally). The two shells 54, 56 further cooperate to define the lock passageway 90 extending through and between the front and rear walls 44, 46 of the receiver body 36. With the shells 54, 56 coupled to one another, the cap 66 coupled to the neck 76, and the cover 82 coupled to the receive body 36, the waste receiver 32 may be considered assembled and ready for deployment.

Figure 21:
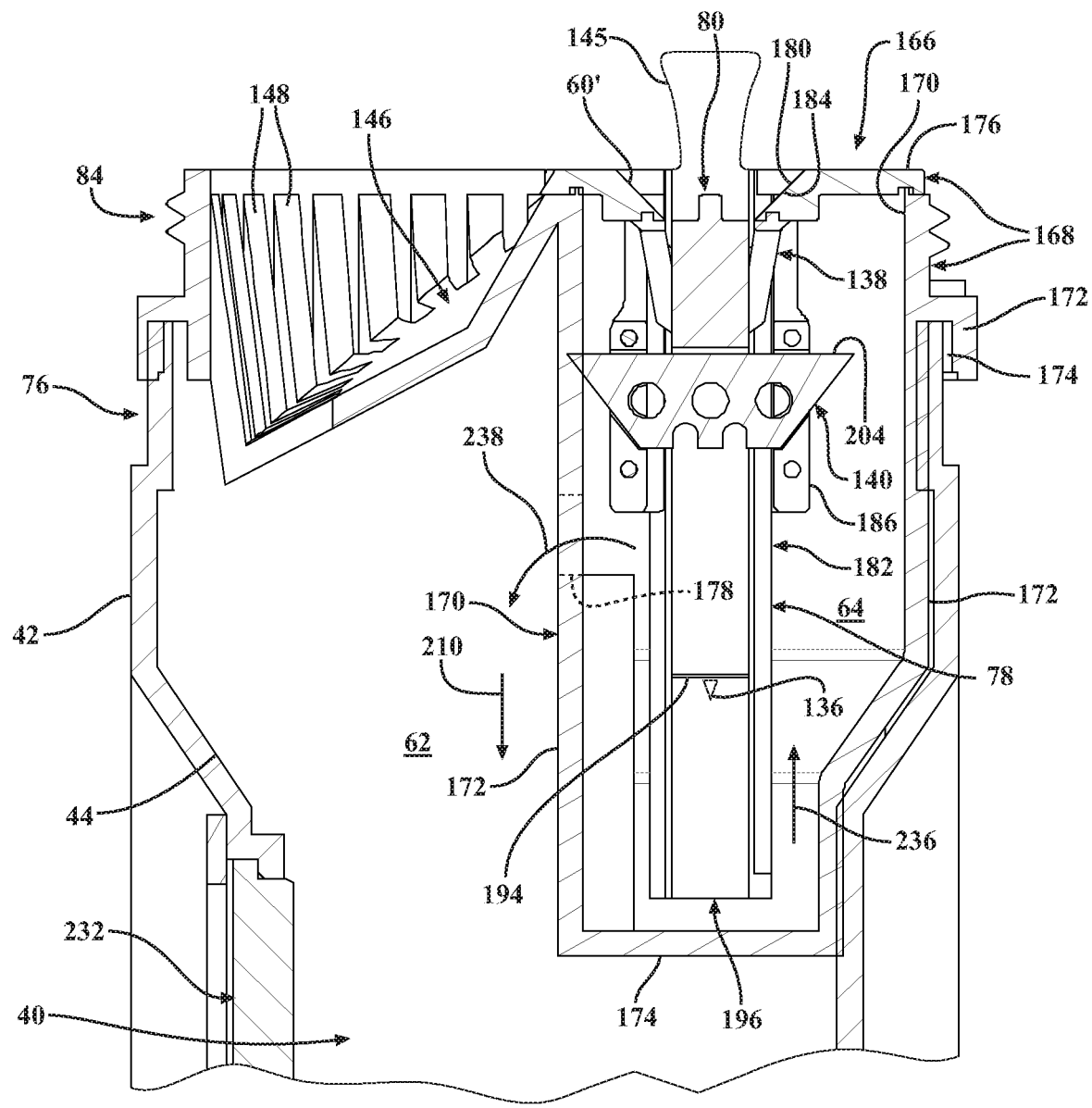
FIG. 21 is an elevation view of a portion of the sectional view of FIG. 19 including the diverter.

In certain implementations, each of the solid and liquid waste volumes 62, 64 are in communication with a single opening of the receiver body 36. As a result, the user may dispose of one or both of the solid and liquid phase pharmaceutical waste material through the single opening and into the receiver body 36 with each phase of the pharmaceutical waste material to be diverted to its respective waste volume 62, 64 for suitable treatment. The diverting or directing one or both of the solid and liquid phase pharmaceutical waste material through the opening(s) 34, 35 (or the single opening) to its respective waste volume 62, 64 may be facilitated with the diverter 166 of the waste receiver 32 previously mentioned. Referring now to FIGS. 15-24, the diverter 166 is coupled to the receiver body 36. In particular, FIG. 21 shows the diverter 166 including a body portion 168 having a rim 170 positioned adjacent the opening(s) 34, 35 of the receiver body 36. Near the rim 170, the diverter 166 has a lip 172 spaced circumferentially from the body portion 168 to define a gap 174 therebetween. The gap 174 is sized to receive a lip of the receiver body 36 to effectively couple the diverter 166 with the receiver body 36. Alternatively, the lip 172 of the diverter 166 may rest atop the lip of the receiver body 36 without the gap 174, or alternatively still, the diverter 166 may not include the lip 172. A joining means, for example, spin welding, adhesive, fasteners, and the like, may permanently fix the diverter 166 with the receiver body 36. In one variant, certain portions of the diverter 166 may be integrally formed with the receiver body 36 through a suitable manufacturing process, for example, injection molding, blow molding, and the like. It is noted that the receiver body 36 and/or the diverter 166 are formed from materials configured to prevent rupture, puncture, chemical degradation, and the like, with further manufacturing considerations such as per unit weight and per unit cost. Suitable materials to form the receiver body 36 and/or the diverter 166 may include durable polymers, composites, fiberglass, glass, ceramic, metal, composites, or a combination thereof. Further, the coupling features 84 of the waste receiver 32 previously mentioned may be disposed on the diverter 166. In particular, FIG. 21 shows the threads associated with the body portion 168 between the rim 170 and the lip 172. As a result, the cover 82 (or cap 66) may be coupled with the diverter 166 to seal the pharmaceutical waste material within the container volume 40.

With the diverter 166 fixed with the receiver body 36 as illustrated in FIG. 21, the body portion 168 of the diverter 166 is at least partially disposed within the container volume 40 of the receiver body 36. The diverter 166 may comprise a solid receiver guide 80 coupled to the body portion 168 and at least partially disposed within the receiver body 36. The solid receiver guide 80 is adapted to direct the solid phase pharmaceutical waste material to the solid waste receiver volume 62. As mentioned, the solid waste receiver volume 62 comprises a portion of the container volume 40 of the receiver body 36. The diverter 166 may further comprise a liquid receiver guide 146 also coupled to the body portion 168 and at least partially disposed within the receiver body 36. The liquid receiver guide 146 is adapted to direct the liquid phase pharmaceutical waste material to the liquid waste receiver volume 64. The liquid waste receiver volume 64 comprises another portion of the container volume 40 of the receiver body 36 with the liquid waste receiver volume 64 being substantially separate from the solid waste receiver volume 62. Each of the solid and liquid receiver guides 80, 146 of the diverter 166 are in communication with the opening(s) 34, 35 such that solid phase pharmaceutical waste material and liquid phase pharmaceutical waste material may be deposited in the solid and liquid receiver guides 80, 146, respectively. Likewise, when the cover 82 or the cap 66 is coupled with the diverter 166 in the manners previously described, the cover 82 or the cap 66 covers both of the solid and liquid receiver guides 80, 146 preventing the solid and liquid waste from escaping.

Figure 18:
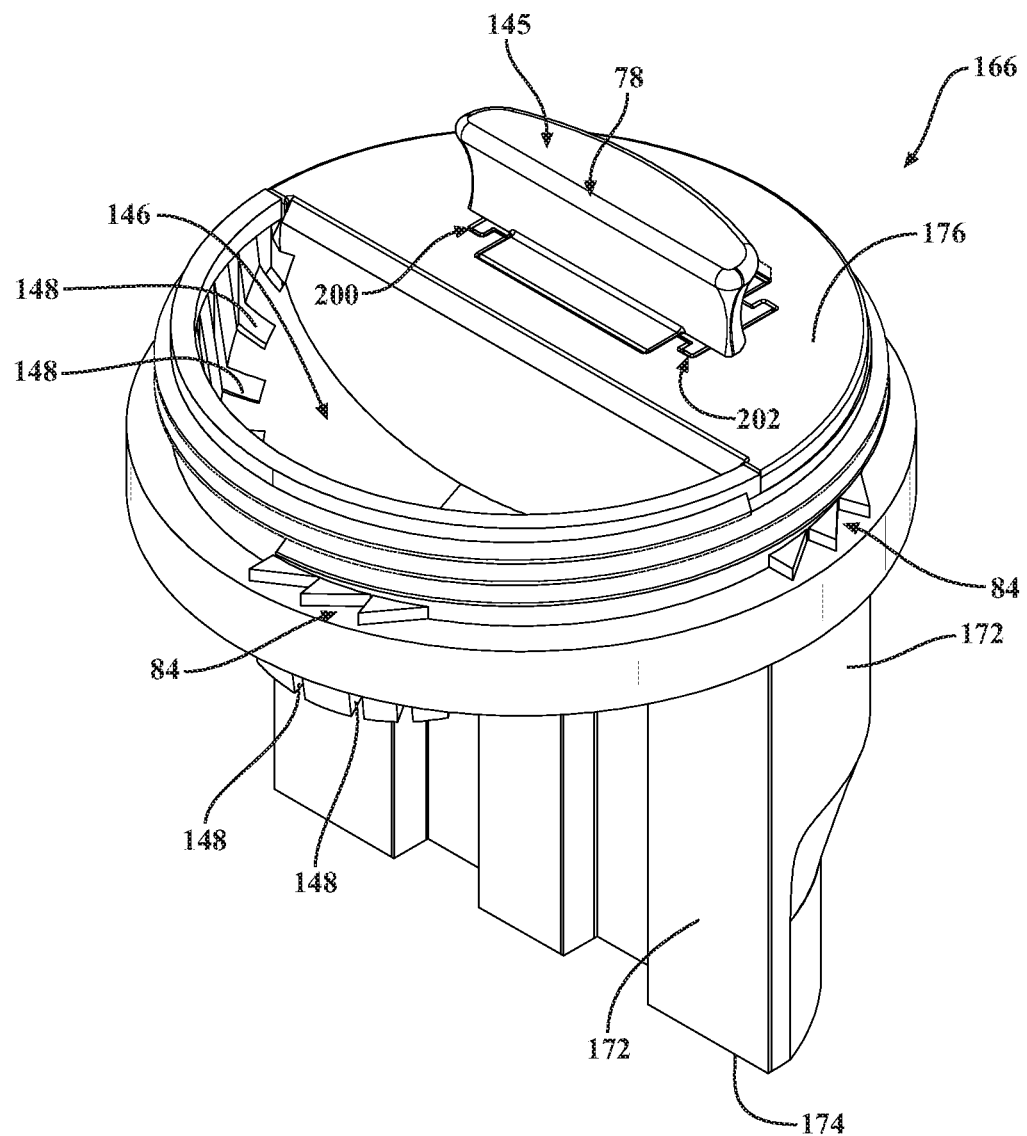
FIG. 18 is a perspective view of a diverter.
Figure 19:
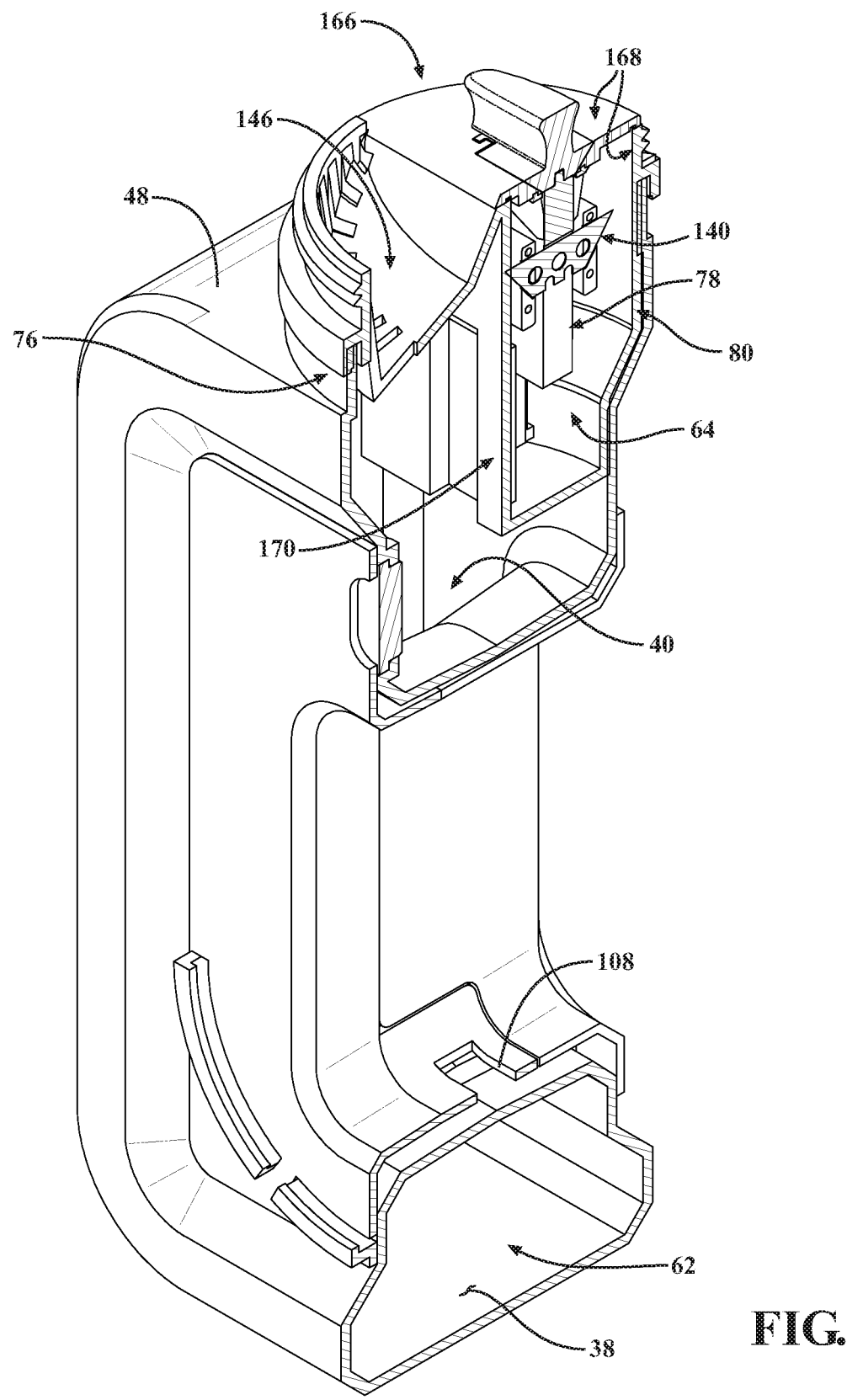
FIG. 19 is a sectional view of the waste receiver of FIG. 16 taken along section lines 19-19.
Figure 20:
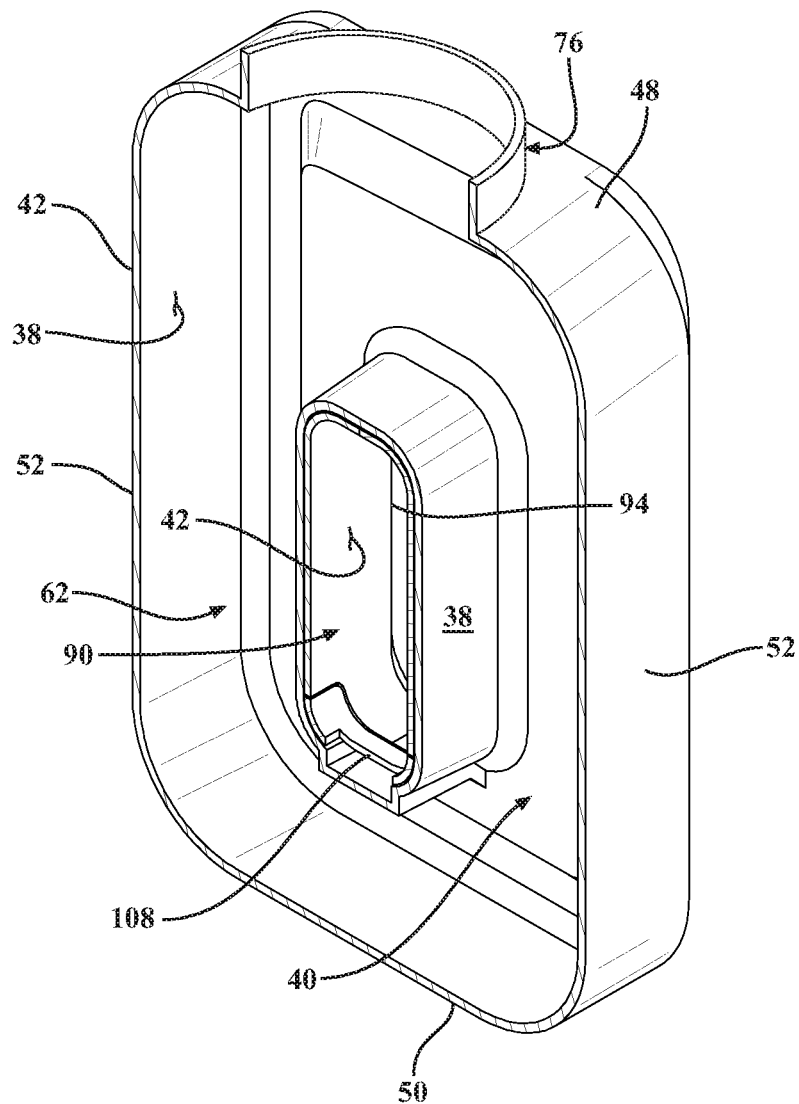
FIG. 20 is a sectional view of the waste receiver of FIG. 16 taken along section lines 20-20.

The solid waste receiver volume 62 and the liquid waste receiver volume 64 may be separated through any number of means. FIGS. 18, 19 and 21 show a partition 170 disposed within the container volume 40 with one side of the partition 170 at least partially defining the solid waste receiver volume 62, and the other side of the partition 170 at least partially defining the liquid waste receiver volume 64. The partition 170 may further include several walls, including at least one sidewall 172 and a lower wall 174 that cooperate to define of an open-ended cavity that may be considered the solid waste receiver volume 62. One of the sidewalls 172 may be contoured to the inner surface 38 of the receiver body 36, as shown in FIG. 18, resulting in an arcuate shape. The other one of the sidewalls 172 may be a chord extending between ends of the arcuately-shaped sidewall 172 resulting in the solid waste receiver volume 62 that is D-shaped when viewed in plan. It is contemplated that the partition 170 may assume any number of shapes other than that illustrated with consideration for maximizing the container volume 40 between the solid and liquid waste receiver volumes 62, 64 therein. It is further contemplated that, in the previously mentioned variant where the diverter 166 is integrally formed with the receiver body 36, the partition 170 may be one of the structures co-molded with the receiver body 36 through the suitable manufacturing process.

With continued reference to FIG. 21, the solid waste receiver volume 62 may be relatively smaller than the liquid waste receiver volume 64. It is appreciated that in certain service locations, upwards of 90% of the pharmaceutical waste material is liquid in phase. For this reason, the liquid waste receiver volume 64 may comprise 60%, 70%, 80% or 90% or greater of the container volume 40 of the receiver body 36. For example, the liquid waste receiver volume 64 may have a capacity of approximately 0.5, 1.0, or 1.5 or greater liters (L), and the solid waste receiver volume 62 may have a capacity of approximately 0.2, 0.4, 0.6 or greater liters. It is understood that the relative portions between the solid and liquid waste volumes 62, 64 are merely exemplary, and the relative volume of the solid and liquid waste receiver volumes 62, 64 may vary based on the application. Furthermore, it is recognized that the size and/or capacity of the waste receiver 32 may be commensurate with the purpose and/or service location of the waste disposal system 30.

The liquid receiver guide 146 may be any suitable structure for directing the liquid phase pharmaceutical waste material to the liquid waste receiver volume 64. The funnel-type device may be provided, and include the orifices 148 for the liquid phase pharmaceutical waste material to pass through to the liquid waste receiver volume 64. The orifices 148 may include a plurality of slots arcuately spaced about the funnel-type device. The orifices 148 of the liquid receiver guide 146 are sized to not only to inhibit or prevent retrieval of the liquid phase pharmaceutical waste material from within the liquid waste receiver volume 64 by impeding tools from entering the liquid waste receiver volume 64, but also impede ingress of the solid phase pharmaceutical waste material to the liquid waste receiver volume 64. However, other orifice designs are also contemplated.

The solid receiver guide 80 directs the solid phase pharmaceutical waste material to the solid waste receiver volume 62, as mentioned, and more particularly in a manner that facilitates the solid phase pharmaceutical waste material being irretrievable and/or unrecoverable. As previously introduced, the solid receiver guide 80 may include one or more of the pushing member 78, the gripping member 136, the funnel member 138, and a cutting element 140. Referring to FIGS. 21-24, the body portion 168 of the diverter 166 may include an upper wall 176 coupled to the rim 170. The upper wall 176 is D-shaped and complementary to the counterposing D-shaped void at least partially defining the inlet of the liquid receiver guide 146. The complementary shapes of the upper wall 176 of the solid receiver guide 80 and the inlet of the liquid receiver guide 146 permit each of the solid and liquid pharmaceutical waste material to be deposited through the opening(s) 34, 35 that is circular and conveniently shaped for receiving the cover 82 of simple geometry. A medial aspect of the upper wall 176 is arranged to be generally aligned with one of the sidewalls 172 comprising the partition 170. As a result, the sidewalls 172, the bottom wall 174, and the upper wall 176 may enclose the solid waste receiver volume 62 with the exception of the inlet 60' and an orifice 178 to be described. In other words, the liquid waste volume may be separated from the solid waste volume except for the orifice 178.

The inlet 60' of the solid receiver guide 80 may be rectangular in shape and sized to receive the solid phase pharmaceutical material including, among other objects, patches and pills. As best shown in FIG. 21, the upper wall 176 may optionally include at least one inclined surface 180 that may partially define the inlet 60'. The inclined surfaces 180 function to guide the solid phase pharmaceutical material towards the funnel member 138 to be further described. Further, the tapering from the inlet 60' to the funnel member 138 with the inclined surfaces 180 prevents retrieval of the solid phase pharmaceutical waste material from within the solid waste receiver volume 62 by impeding tools from entering the solid receiver guide 80.

The pushing member 78 is movably disposed relative to the solid receiver guide 80. The pushing member 78 is adapted to receive an input from a user to move the solid phase pharmaceutical waste material through the solid receiver guide 80. The pushing member 78 includes a main body 182 defining a grip or handle 145. The handle 145 includes control surface adapted to receive the input from the user to move the pushing member 78 relative to the solid receiver guide 80. The handle 145 may extend above the upper wall 176 of the body portion 168 of the diverter 166 when the pushing member 78 is in a second position. The control surface may be arranged to be manipulated by the user, for example pinched, to provide the input to the pushing member 78. The main body 182 may include at least one inclined surface 184 complementary to the inclined surface 180 of the upper wall 176. The complementary inclined surfaces 180, 184 are arranged to abut one another when the pushing member 78 is in the second position. In other words, the inclined surfaces 180 of the upper wall 176 directly contacts the inclined surfaces 184 of the main body 182 to prevent the pushing member 78 from being further advanced downwardly into the solid receiver guide 80. With the complementary inclined surfaces 180, 184 in direct contact and the pushing member 78 in the second position, a portion of the handle 145 is flush with the upper wall 176 for aesthetics and selectively preventing access to the solid receiver guide 80.

The main body 182 may be generally sized approximate the inlet 60' and a channel defined by the upper wall 176 and the opposing barriers 186 of the solid receiver guide 80, as best shown in FIG. 21. The main body 182 is substantially rectangular when viewed in plan. In particular, the main body 182 may include a first pair of opposing side surfaces 188, a second pair of opposing side surfaces 190, an upper surface 192 generally defining an interface between the main body 182 and the handle 145, and a lower surface 194 opposite the upper surface 192. Of course, the main body 182 may have other suitable shapes. As will be described in greater detail, the lower surface 194, or components thereon, is the structure that directly contacts the solid phase pharmaceutical waste material to move the solid phase pharmaceutical waste material through the solid receiver guide 80.

Figure 23:
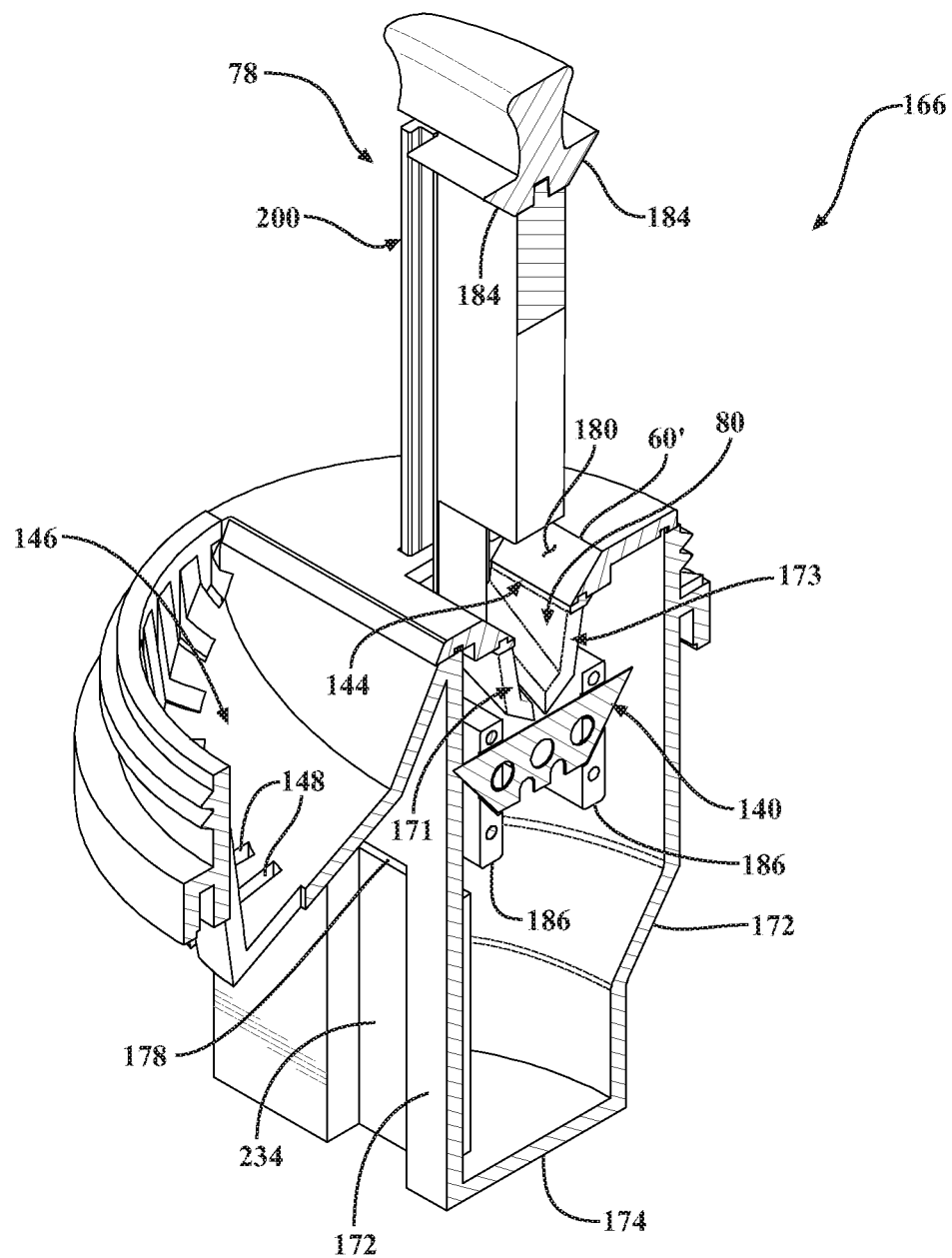
FIG. 23 is a sectional view of the diverter of FIG. 22 taken along lines 23-23.
Figure 24:
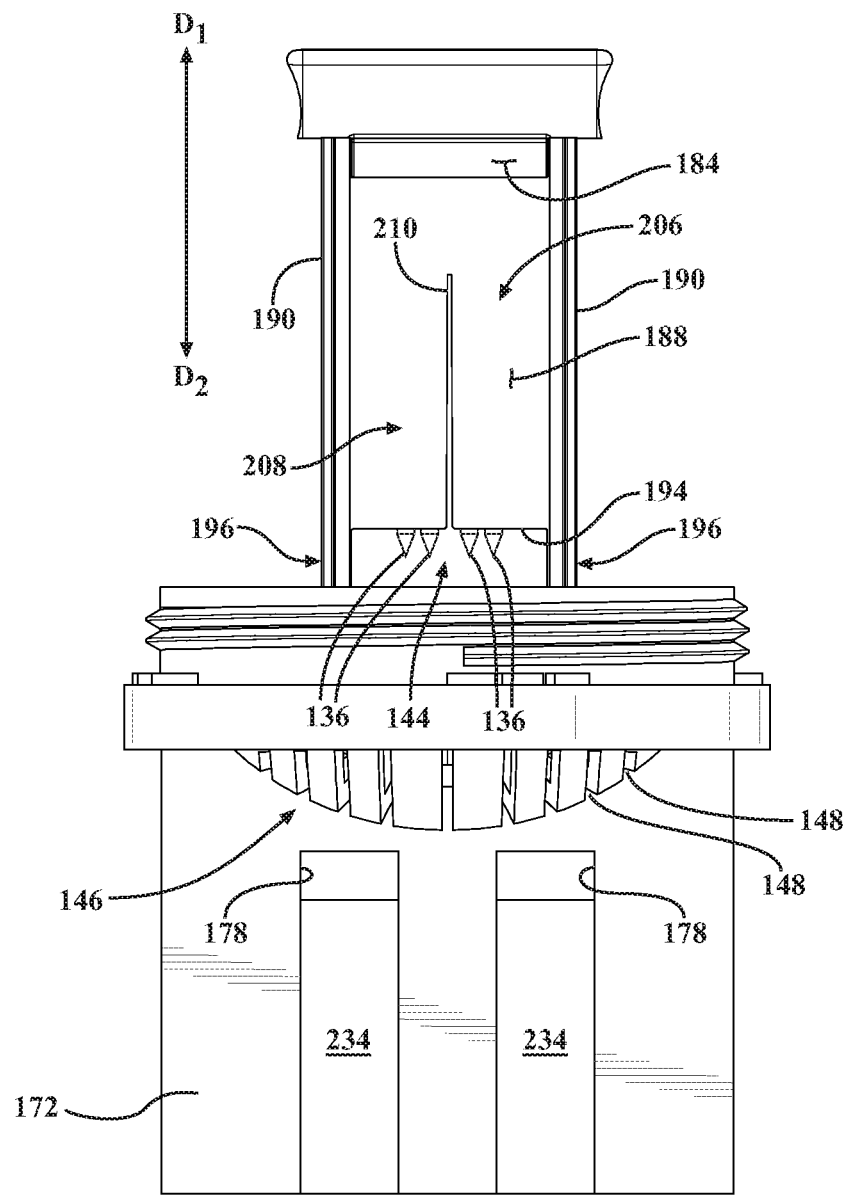
FIG. 24 is an elevation view of the diverter of FIG. 22.

As best shown in FIGS. 23-25, the pushing member 78 may include a leg 196 extending from the main body 182 with two legs shown. The legs 196 may generally extend from the lower surface 194 of the main body 182 in a direction opposite the handle 145. Each of the legs 196 may be at least partially defined by a portion of one of the side surfaces 188 of the main body 182, and an inner leg surface 198 opposite the portion of the side surface 188. The pushing member 78 may further include track features 200 extending along the main body 182 and at least partially defining the side surfaces 190. Each of the track features 200 engage a complimentary rail feature 202 within the channel of the upper wall 176 of the body portion 168. The rail features 202 are positioned opposite the inlet 60' and opening into the inlet 60'. The track features 200 extend from the main body 182 and sized in a manner to be slidably and snugly received within the rail features 202 to facilitate smooth movement of the pushing member 78. The pushing member 78 may further include a foot 204 extending from the leg 196 with two feet shown. The feet 204 prevent complete removal of the pushing member 78 from the solid receiver guide 80. When the pushing member 78 is in the second position and at a maximum, the feet 204 interfere with a complimentary structure of the solid receiver guide 80 to prevent further retraction. The aforementioned structures of the pushing member 78 may be of unitary construction and formed from a durable plastic or other suitable materials.

Figure 22:
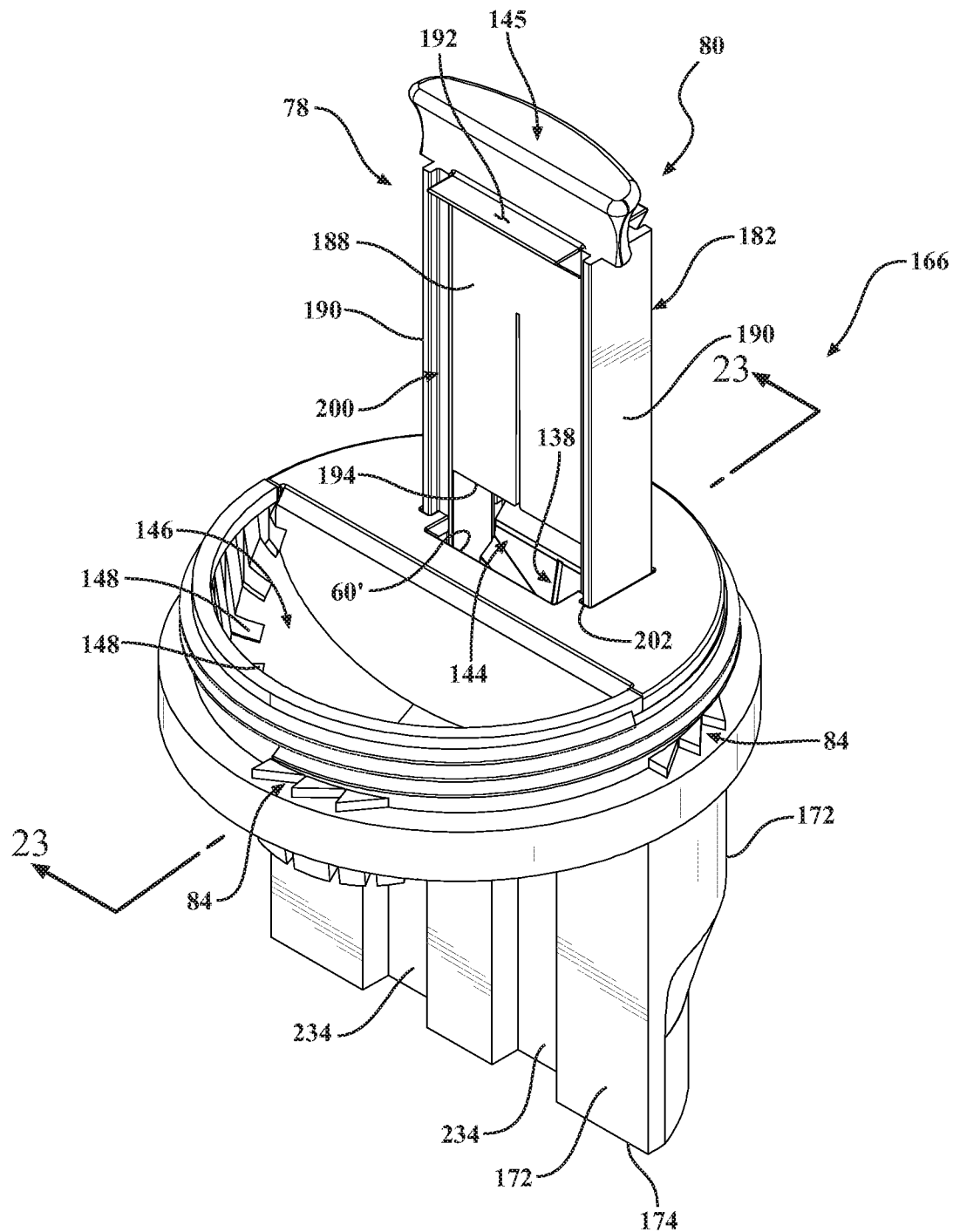
FIG. 22 is a perspective view of the diverter of FIG. 18 with a pushing member in a first position to define a window.

As mentioned, the pushing member 78 is movable to the second position illustrated in FIG. 19, and is further movable to a first position illustrated in FIGS. 22-24. In the first position, the main body 182 is spaced from the solid receiver guide 80 to provide the window 144 at least partially defined between the main body 182, the legs 196, and the solid receiver guide 80. Moving the pushing member 78 to the first position exposes the inlet 60' of the solid receiver guide 80 and provides the window 144 for receiving the solid phase pharmaceutical waste material. To move the pushing member 78 to the first position, the input is provided to the control surface of the handle 145 with the input being a linear force in a first direction (D1), which may be generally upwardly relative to the diverter 166. The main body 182 of the pushing member 78 slidably moves within the channel and through the inlet 60' of the solid receiver guide 80. The motion may continue until at least the lower surface 194 of the main body 182 exits the solid receiver guide 80 and is positioned above the upper wall 176 of the body portion 168 of the diverter 166. The void between the lower surface 194 and the inlet 60' may be considered to bound the window 144 on the upper and lower sides, respectively. The legs 196 of the pushing member 78 may bound the window 144 laterally. At least a portion of the legs 196 may remain within the solid waste receiver volume 62 when the pushing member 78 is in the first position. With the window 144 exposing the inlet 60' of the solid receiver guide 80, the user deposits the solid pharmaceutical waste material within or near the inlet 60'. In other configurations, the legs are optional and the pushing member may be removable from the container.

The pushing member 78 is moved from the first position to the second position to facilitate moving of the solid phase pharmaceutical waste material through the solid receiver guide 80. To move the pushing member 78 from the first position to the second position, another input is provided to the control surface of the handle 145 with the input being a linear force in a second direction (D2) opposite the first direction. The second direction may be generally downwardly or towards the diverter 166. The complementary track features 200 slidably and snugly move relative to the rail features 202 to facilitate smooth movement of the pushing member 78. Other track features are contemplated, such as rolling members or bearings.

The main body 182 of the pushing member 78 slidably moves towards the inlet 60' in which the solid pharmaceutical waste material has previously been deposited. The solid pharmaceutical waste material interferes with the lower surface 194 of the main body 182 passing through the inlet 60' of the solid receiver guide 80. The lower surface 194 urges the solid pharmaceutical waste material through the inlet 60' and into the channel. The inclined surfaces 180 of the upper wall 176 may cooperate to ensure the solid phase pharmaceutical waste material does not inadvertently escape the bounds of the inlet 60' upon coming into contact with the lower surface 194 of the pushing member 78 being moved in the second direction. The motion may continue until at least the inclined surfaces 184 of the pushing member 78 are in direct contact with the inclined surfaces 180 of the diverter 166, at which point the window 144 no longer is present and the pushing member 78 has returned to the first position. As the pushing member 78 moves from the second position to the first position, the lower surface 194 of the pushing member 78 moves through the channel to be situated beneath the barriers 186 within the solid waste receiver volume 62. As a result, the solid phase pharmaceutical waste material is likewise directed into the solid waste receiver volume 62 containing a fluid to be later described with the fluid at least partially dissolving active medicine associated with the solid phase pharmaceutical waste material such that a residual liquid may become disposed on the end of the pushing member 78.

As previously mentioned, solid phase pharmaceutical waste material of particular interest are patches and pills, and the waste receiver 32 advantageously includes features to facilitate treating the patches and pills in a manner that renders them irretrievable and/or unrecoverable. In particular, it is known that used patches contain unused medicine and unused pills obviously contain unused medicine, including narcotics. Those seeking to engage in drug diversion may attempt to retrieve the patches and pills, and recover the narcotics from the same. Known systems that include a fluid for dissolving the unused medicine on the patch and/or the unused pills may be deficient in several respects, at least one of which is the time required for the fluid to suitably penetrate the patch and the pill to dissolve the unused medicine.

Referring now to FIGS. 19, 21 and 23, the waste receiver 32 may include the cutting element 140, for example a blade, coupled to the solid receiver guide 80. The cutting element 140 is disposed within the solid waste receiver volume 62 and positioned to cut the solid phase pharmaceutical waste material. In particular, the cutting element 140 is adapted to at least score a patch or a pill upon insertion of the patch or the pill through the solid receiver guide 80. As used herein, "scoring" includes engaging the patch or the pill with an edge 204 of the cutting element 140. The scoring of the patch or the pill exposes a greater surface area of the patch or the pill for more thorough processing of the solid phase pharmaceutical waste material in manners to be described.

In certain cases, the scoring of the patch or pill damages a barrier that would otherwise prevent rapid deactivation of the pharmaceutical waste. With respect to the pill, the barrier may be a coating or capsule. With respect to the patch, the barrier may be a layer of the patch. The cutting element 140 may take any suitable form, such as the blade, rotating cutting device, cutting wheels, etc. The use of the blade, such as a razor blade, results in a low-cost and effective option suitable for a disposable assembly. The cutting element 140 may be statically mounted or movable linearly relative to the waste receiver 32 and/or be free of any motorized components, again, in the aim of simplicity and cost-reduction. The cutting element 140 may consist of a single cutting edge.

The inlet 60' of the solid receiver guide 80 is preferably sized to permit insertion of patches and pills without excess clearance so as to limit the extent to which the items may be retrieved. The cutting element 140 is spaced below the inlet 60' of the solid receiver guide 80 by a suitable distance such that a person is not injured should he or she attempt to urge the patch downwardly along the solid receiver guide 80 without the use of the pushing member 78. The cutting element 140 may be coupled to the solid receiver guide 80 through riveting, interference fit, adhesives, and other joining means. As best shown in FIGS. 21 and 23, the cutting element 140 is coupled to the barriers 186 disposed within the solid waste receiver volume 62 and defining the channel. In particular, the barriers 186 each comprise opposing portions coupled together with pins with the cutting element 140 sandwiched between the opposing portions. In one configuration, the cutting element 140 is oriented such that the edge 204 of the cutting element 140 is oriented towards the inlet 60' of the solid receiver guide 80 such that the solid phase pharmaceutical waste material being moved through the solid receiver guide 80 initially encounters the edge 204 before passing the cutting element 140.

As explained, the pushing member 78 moves the solid phase pharmaceutical waste material through the solid receiver guide 80, and the cutting element 140 at least scores the solid phase pharmaceutical waste material being moved through the solid receiver guide 80. The waste receiver 32 includes further features to increase the likelihood that the solid phase pharmaceutical waste material being moved through the solid receiver guide 80 properly encounters the edge 204 of the cutting element 140. With reference to FIGS. 24 and 25, the main body 182 of the pushing member 78 includes a first portion 206 and a second portion 208 spaced apart from the first portion 206 to define a slot 210 therebetween. The slot 210 may extend upwardly from the lower surface 194 of the main body 182 such that, when the pushing member 78 is in the first position, the slot 210 is in communication with the window 144. The slot 210 is sized to receive the cutting element 140 as the pushing member 78 moves from the first position to the second position. In other words, with the cutting element 140 received within the slot 210, the cutting element 140 is positioned between the first and second portions 206, 208 of the main body 182 and above the lower surface 194. Among other advantages, receiving the cutting element 140 within the slot 210 permits the pushing member 78 to be inserted into a greater distance within the solid receiver guide 80 (i.e., without obstruction from the cutting element 140).

The inlet 60' of the solid receiver guide 80 may be elongate (e.g., rectangular in accordance with dimensions of a cross section of most patches) with the cutting element 140 oriented substantially perpendicular to the inlet 60'. For example, when viewed in plan, the body of the cutting element 140 may be oriented horizontally with the inlet 60' of the solid receiver guide 80 oriented vertically. The cutting element 140 may be positioned approximately midway between opposing ends of the inlet 60', and the slot 210 is spaced equidistant from the opposing sides 190 and in alignment with the edge 204 of the cutting element 140. As the pushing member 78 is moved from the first position to the second position to move the patch through the solid receiver guide 80, the edge 204 of the cutting element 140 encounters the patch and the patch is "pinched" between the edge 204 of the cutting element 140 and the lowermost aspect of the slot 210, thereby increasing the likelihood the patch is scored in a suitable manner. Further, with the slot 210 receiving the cutting element 140, the patch is urged further within the solid receiver guide 80, thereby increasing the likelihood that the patch appropriately descends further into the solid waste receiver volume 62. It is further contemplated that the cutting element 140 may be provided in singular as shown, or two, three or four or more blades may be provided in a parallel, angled, or perpendicular fashion.

The inherent flexibility of patches is associated with the possibility that the patch positioned within the window 144 with the pushing member 78 in the first position may become contorted or at least partially "eject" from the window 144 as the pushing member 78 is moved from the first position to the second position. For example, if a square-shaped patch is rested upon the upper wall 176 of the diverter 166 to be bifurcated by the lower surface 194 of the main body 182, as the pushing member 78 is moved towards the second position, the patch may favor one side of the main body 182 and not be properly moved through the solid receiver guide 80. To avoid the aforementioned undesirable result, the pushing member 78 may include the gripping member 136 adapted to engage the patch. As best shown in FIGS. 21 and 24, the gripping member 136 is coupled to the main body 182, and more particularly to the lower surface 194 of the main body 182. The gripping member 136 may be a spike tapering to a point configured to penetratingly engage the patch typically comprised of a woven fabric or permeable layer. More than one gripping member 136 may be provided such as the four spikes shown in FIG. 24. Two of the spikes are coupled to the first portion 206 of the main body 182, and another two of the spikes are coupled to the second portion 208 of the main body 182. As a result, as the pushing member 78 is moved from the first position to the second position, the gripping member(s) 136 engage the patch prior to the patch engaging the lower surface 194. Lateral movement of the patch relative to the pushing member 78 is eliminated or limited such that the patch remains as initially positioned relative to the main body 182 as the pushing member 78 continues through the inlet 60' of the solid receiver guide 80 and receives the cutting element 140 within the slot 210. In other words, the gripping member 136, the cutting element 140, and the slot 210 cooperate to ensure the patch is at least partially scored as it is moved through the solid receiver guide 80 into the solid waste receiver volume 62.

Whereas the patches typically have a size and shape to be scored relatively easily by the cutting element 140 when properly moved through the solid receiver guide 80, it is readily appreciated that the scoring of pills is associated with additional challenges based on their size and shape. The challenges may be particularly pronounced with the cutting element 140 being a blade with a singular edge. The waste receiver 32 overcomes at least the aforementioned challenge with the funnel member 138 previously mentioned. The funnel member 138 may be disposed in the solid waste receiver volume 62 between the inlet 60' and the cutting element 140. In particular, the funnel member 138 may be coupled to an interior surface of the upper wall 176 of the diverter 166.

Figure 27:
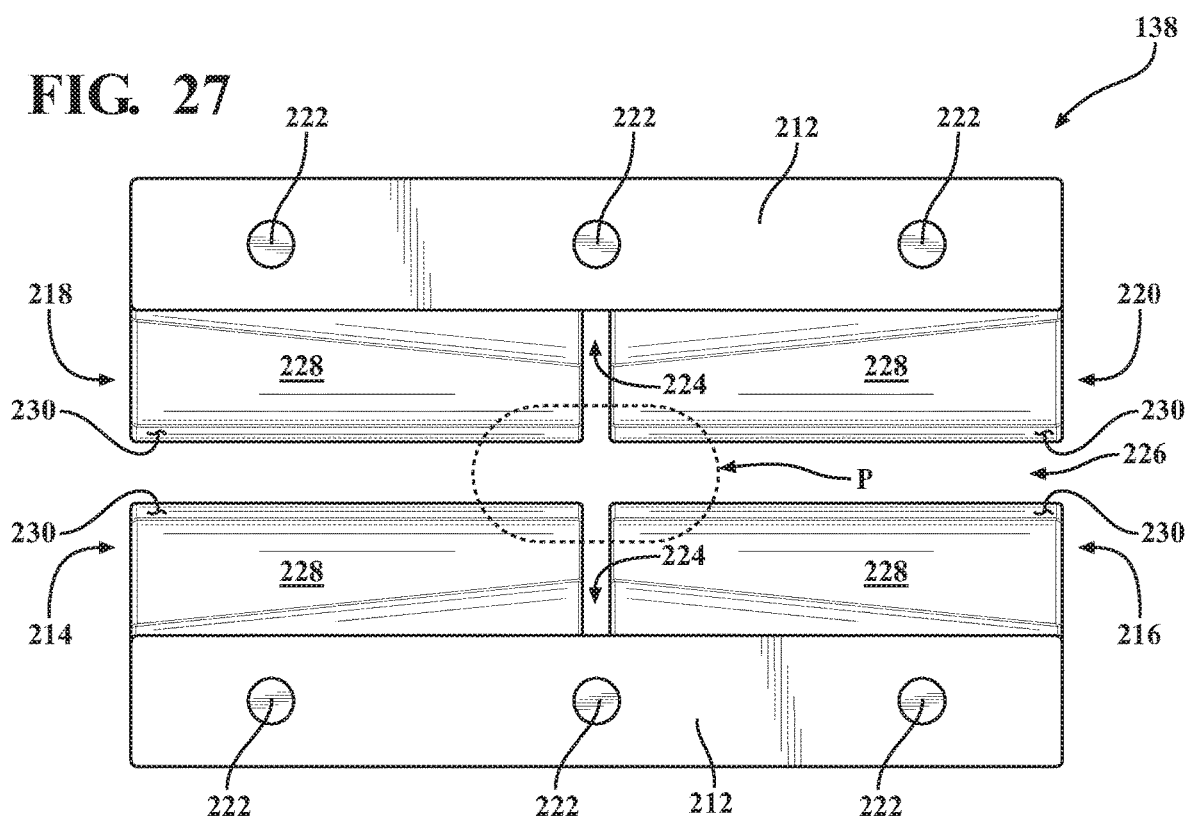
FIG. 27 is a plan view of the funnel member.

FIGS. 26 and 27 show a perspective and a plan view, respectively, of the funnel member 138. The funnel member 138 may include at least one frame element 212 and a plurality of sections 214, 216, 218, 220 coupled to the frame element 212 (also referred to herein as a first section 214, a second section 216, a third section 218, and a fourth section 220). The frame element 212 includes two elongate plates with posts 222 disposed on one surface of the frame element 212 and the sections 214-220 disposed on the opposite surface of the frame element 212. The posts 222 are received within complementary voids of the interior surface of the upper wall 176 to couple the funnel member 138 with the upper wall 176. Two of the sections 214-220 may be coupled to each of the frame elements 212. Other configurations of the frame elements 212 are also contemplated. Alternatively, the plurality of sections may be directly coupled to the solid waste guide.

The sections 214-220 are positioned to define a first gap 224 and a second gap 226. In particular, the first and second sections 214, 216 are spaced apart from one another to define the first gap 224, or at least a portion thereof; the third and fourth sections 218, 220 are spaced apart from one another to further define the first gap 224, or at least a portion thereof; the first and third sections 214, 218 are spaced apart from one another to define the second gap 226, or at least a portion thereof; and, the second and fourth sections 216, 220 are spaced apart from one another to further define the second gap 226, or at least a portion thereof. FIG. 27 shows the funnel member 138 being symmetric about each of the first and second gaps 224, 226 and the first and second gaps 224, 226 being perpendicular to one another. The first and second gaps 224, 226 may be sized to be at least slightly smaller than at least some pills such that the pill(s) deposited through the inlet 60' of the solid receiver guide 80 are supported on at least two of the sections 214-220. The pill(s) remain situated on the funnel member 138 until urged through the first and second gaps 224, 226 with the pushing member 78 in a manner to be described.

As best shown in FIG. 23, the first gap 224 is positioned above the cutting element 140, and more particularly, the edge 204 of the cutting element 140. In other words, if the cutting element 140 is the blade, the first gap 224 and the cutting element 140 may be considered aligned with each other with the cutting element 140 positioned beneath the funnel member 138 relative the upper wall 176. In other words, the edge 204 of the cutting element 140 may be centered within the first gap 224. Further, the first gap 224 is vertically aligned with the slot 210 of the pushing member 78. Each of the sections 214-220 may include an inclined surface 228 oriented towards one another to define a cavity or funnel-type shape of the funnel member 138. The inclined surfaces 228 are oriented towards the first gap 224, and preferably oriented towards the second gap 226, as best shown in the perspective view of FIG. 26. As a result, when a pill is deposited through the inlet 60' of the solid receiver guide 80 with the pushing member 78 in the first position, the pill descends into contact with the funnel member 138 under the influence of gravity. The inclined surfaces 228 guide the pill (P) to be supported above the first gap 224, and preferably above the second gap 226, as best shown in FIG. 27. In other words, when the pill is supported above the first and second gaps 224, 226, each of the sections 214-220 may support a portion of the pill. As the pushing member 78 is moved from the first position to the second position, the lower surface 194 of the main body 182 urges the pill through the funnel member 138 and into engagement with the edge 204 of the cutting element 140. With the cutting element 140 below and sufficiently near the first gap 224, the likelihood that the pill does not engage the edge 204 of the cutting element 140 is minimized. The edge 204 of the cutting element 140 at least partially scores the pill, which then further descends within the solid waste receiver volume 62 under the influence of gravity (or further moved with the pushing member 78). With the pill suitably scored and perhaps sliced, the fluid within the solid waste receiver volume 62 more likely comes into contact with the active medicine of the pill (i.e., beneath the coating, within the capsule, etc.).

As mentioned, the first and second gaps 224, 226 may be sized to be at least slightly smaller than at least some pills, yet the pushing member 78 moves the pill through the funnel member 138 and into engagement with the cutting element 140. To facilitate this unique functionality, each of the sections 214-220 may be formed from flexible and resilient material suitable for deflecting when subjected to more than minimal forces. As a result, as the pushing member 78 moves the pill through the first and second gaps 224, 226, the sections 214-220 deflect to provide suitable clearance for the pill to pass through the first and second gaps 224, 226. The second gap 226 is also sized to be at least slightly smaller than the main body 182 of the pushing member 78. As a result, as the pushing member 78 moves through the second gap 226 of the funnel member 138, the sections 214-220 deflect away from the main body 182 to provide suitable clearance for the main body 182 to pass through the first and second gaps 224, 226. In one example, the first and third sections 214, 218 deflect away from one another, and the second and fourth sections 216, 220 deflect away from one another. In such an example, a size of the first gap 224 (e.g., spacing between the first and second sections 214, 216 and the third and fourth sections 218, 220) may remain unchanged. The precise motion of the deflection may be based, at least in part, on the manner in which the sections 214-220 are coupled to the frame elements 212. It is understood that the funnel member 138 including four sections is merely exemplary, and in variants the funnel member 138 may include two, three, five, six or seven or more sections. For example, in one variant the funnel member 138 may include six sections arranged circumferentially and each triangular in shape with each of the sections configured to deflect to provide a circular-shaped aperture.

In further variants, the funnel member 138 may include two, three or four or more sections with the sections not being formed from flexible and resilient material. Rather, the sections are rigid and are movably coupled to a suitable structure of the receiver body 36 and/or the funnel member 138, for example the frame elements 212, in a manner to responsively move when subjected to forces moving the solid phase pharmaceutical waste material and/or the pushing member 78 through the first and second gaps 224, 226. In one example, the first and second sections 214, 216 formed from rigid material may be pivotally coupled to one of the frame elements 212, and the third and fourth sections 218, 220 formed from rigid material may be pivotally coupled to the other one of the frame elements 212. Each of the sections 214-220 pivot in a suitable manner to permit the solid phase pharmaceutical waste material and/or the pushing member 78 to move through the second gap 226. A biasing element (e.g., a torsion spring) may bias the sections 214-220 with suitable force to support certain solid phase pharmaceutical waste material, for example, a pill.

It is readily appreciated that when the pushing member 78 is in the second position, the sections 214-220 are in a deflected condition. As the lower surface 194 of the main body 182 moves through the second gap 226 and as the pushing member 78 is moved towards the first position, the sections 214-220 resiliently return to a natural condition. Yet, in the second position, a portion of the main body 182 may be disposed relatively "deep" within the solid waste receiver volume 62, and perhaps in contact with the medicine-infused fluid contained within the solid waste receiver volume 62 (i.e., the fluid subsequent to dissolving the active medication during the operational lifecycle of the waste receiver 32). As a result, moving the pushing member 78 from the second position to the first position may expose to the outside environment the portion of the main body 182 that may have been in contact with the medicine-infused fluid. The aforementioned concern is ameliorated by the funnel member 138 including wiper surfaces 230 associated with each of the sections 214-220. With continued reference to FIGS. 26 and 27, the wiper surfaces 230 are the surfaces in direct contact with the opposing sides 188 of the pushing member 78 as the main body 182 causes the sections 214-220 to deflect. With the sections 214-220 resiliently being urged against the opposing sides 188 of the pushing member 78, the wiper surfaces 230 provide a "wiper function" to remove any medicine-infused fluid present on the opposing sides 188 of the pushing member 78, further rendering the solid phase pharmaceutical waste material disposed within the solid waste receiver volume 62 irretrievable.

As mentioned, a liquid, such as water, may be added to the solid receiver guide 80 to prime the solid waste receiver volume 62 prior to use. In addition or an alternative to water being within the solid waste receiver volume 62 to dissolve the active medication in the solid phase pharmaceutical waste material, another reaction agent (not shown) may be provided to react with water or other fluids in order to chemically and/or physically break down the solid phase pharmaceutical waste material within the solid waste receiver volume 62, and/or make the solid waste undesirable and/or indigestible. The reaction agent may be positioned and/or contained within one or more dissolvable or fluid permeable packets (not shown) within the solid waste receiver volume 62. For example, multiple packets may be used with each packet containing a same or different reaction agent. The fluid may catalyze the reaction between the solid phase pharmaceutical waste material and the reaction agent to destroy or otherwise chemically and/or physically change the solid waste to an unusable and/or unrecoverable form. Alternatively, the liquid may solidify the reaction agent to encapsulate or otherwise surround the solid phase pharmaceutical waste material in the solid waste receiver volume 62.

At least a substantial portion of the receiver body 36 may be formed from opaque materials so as to conceal the presence of any of the pharmaceutical waste material deposited therein. Yet it is desirable to provide an indication to the user of the level or volume of the pharmaceutical waste material within the container volume 40, and more particularly the liquid phase pharmaceutical waste material within the liquid waste receiver volume 64. The indication, for example a visual indication, alerts the user that the capacity of the replaceable waste receiver 32 is being neared, and the time to replace the waste disposal system 30 with a new waste receiver 32 may be approaching. The waste disposal system 30 may include an indicator or a viewing port 232 associated with the receiver body 36. The indicator 232 may be suitably positioned on the receiver body 36 to come into contact with the liquid phase pharmaceutical waste material when a level of the liquid phase pharmaceutical waste material is above a predetermined level, for example, nearing the capacity of the container volume 40. The indicator 232 is disposed on or within the front wall 44 and generally positioned near the top of the waste receiver 32. More specifically, the indicator 232 is positioned approximately spaced from the bottom wall 50 by three-quarters of a height of the receiver body 36 defined between the top and bottom walls 48, 50. Once the level of the liquid phase pharmaceutical waste material is at the position of the indicator 232, the indicator 232 provides visual indication to the user. In one example, the indicator 232 is the viewing port including a window formed from transparent material with the window aligned with an aperture defined by the front wall 44 of the receiver body 36. The user may view the fluid line with the container volume 40 when the fluid line is in contact with an inner surface of the window behind the aperture. A plurality of indicators may also be provided along the height, denoting the various proportions of filling for the container.

In another example, the indicator 232 is a liquid contact indicator (also known as a moisture-detecting indicator or liquid submersion indicator) formed from material configured to undergo a chemical reaction and change colors upon coming into direct contact with the liquid phase pharmaceutical waste material within the liquid waste receiver volume 64. The liquid contact indicator may be a first color (e.g., white) upon assembly and installation at the service location, and change to a second color (e.g., red) once the level of the liquid phase pharmaceutical waste material is above the predetermined level based on the position of the indicator 232. The figures show a single indicator 232 in the aforementioned position, but it is contemplated the waste receiver 32 may include two, three, or four or more indicators suitably positioned to provide visual indication(s) of the level of the pharmaceutical waste material within the container volume 40.

In one variant, a coloring agent, for example a dye, may be dispersed into the liquid waste receiver volume 64 to color the liquid phase pharmaceutical waste material and/or the fluid absorber. The colored liquid phase pharmaceutical waste material and/or the fluid absorber is more readily visible through the viewing port comprising the indicator 232. In one example, the coloring agent is provided within the packet together with the fluid absorber. The liquid phase pharmaceutical waste material may solubilizes the film of the packet thereby releasing the coloring agent and the chemical composition into the liquid waste receiver volume 64. As additional amounts of the liquid phase pharmaceutical waste material is added to the liquid waste receiver volume 64, the material and the fluid absorber assume the color of the coloring agent. Once the fluid line is in contact with an inner surface of the window behind the aperture, the colored material is readily visible to the user viewing the indicator 232.

Once it is desired to replace the waste receiver 32, for example based on the visual indication provided to the user with the indicator 232 showing the waste receiver 32 to be sufficiently full, the waste disposal system 30 may include further advantageous features to facilitate safe disposal of the waste receiver 32. In particular, it is undesirable to transport the waste receiver 32 containing any contents in the liquid phase, which may include residual water added to the solid waste receiver volume 62 to dissolve the solid phase pharmaceutical waste material prior to use. Known systems may require adding a substance to substantially solidify the liquid contents. Yet those systems requiring separately storing a solidifying agent during the operational lifecycle of the waste receiver 32, then further require handling and/or adding the substance are associated with risk of exposure to potentially harmful chemicals. The waste disposal system 30 of the present disclosure may advantageously provide for near-complete or complete solidification of the pharmaceutical waste material in a self-contained manner.

The waste receiver 32 may include at least one orifice 178 providing fluid communication between the solid waste receiver volume 62 and the liquid waste receiver volume 64. Referring to FIGS. 21, 23 and 24, the partition 170 of the diverter 166 defines the orifice 178, and more particularly, two orifices 178 extend through the sidewall 172 at least partially defining the partition 170. The orifices 178 are generally positioned near the top of the receiver body 36 such that fluid from the solid waste receiver volume 62 (e.g., the medicine-infused fluid) does not prematurely pass through the orifices 178 to the liquid waste receiver volume 64 until the self-contained solidification method is performed. It is contemplated that in alternative variants, the orifice(s) 178 may be positioned within any suitable portion of the diverter 166. The diverter 166 may further include at least one channel 234 in communication with the orifices 178. FIGS. 22 and 24 show two channels 234 recessed within the sidewall 172 and extending between the orifices 178 and the lower wall 174 of the partition 170. The channels 234 ensure that fluid communication is maintained between the solid and liquid waste volumes 62, 64 via the orifices 178 should the liquid waste receiver volume 64 become substantially consumed with the fluid absorber. In other words, as the fluid absorber absorbs the liquid phase pharmaceutical waste material in the liquid waste receiver volume 64, the fluid absorber expands significantly and may directly contact the sidewall 172 of the partition 170 near the orifices 178. The fluid from the solid waste receiver volume 62 may be effectively transferred to the liquid waste receiver volume 64 through the orifices 178 and the clearance afforded by the channels 234.

The self-contained solidification method will now be described. The liquid waste receiver volume 64 may include the liquid phase pharmaceutical waste material that is substantially solid after being absorbed by the fluid absorber (e.g., the SAP). The solid waste receiver volume 62 may include the solid phase pharmaceutical material that is substantially liquid after being dissolved by the reaction agent (e.g., the medicine-infused fluid). The fluid absorber may not be fully saturated such that the fluid absorber has capacity to absorb additional liquid. The user positions the retainer cover 82 on the receiver body 36 to cover the opening(s) 34, 35 to seal the solid phase pharmaceutical waste material and the liquid phase pharmaceutical waste material within the receiver body 36 in manners previously described. With particular reference to FIG. 21, the waste receiver 32 is manually repositioned or manipulated, such as inverted, such that the liquid contents within the solid waste receiver volume 62 descend under the influence of gravity (in the direction of arrow 236 when the waste receiver 32 is substantially inverted). The waste receiver 32 may be manipulated in a manner that agitates the liquid contents. The liquid contents may be prevented from exiting the solid receiver guide 80 by the pushing member 78 sealing the inlet 60' of the solid receiver guide 80. Further, the cover 82 seals the solid and liquid receiver guides 80, 146 to prevent egress of the contents of the receiver volume 40 thereby rendering the method self-contained. The liquid contents pass from the solid waste receiver volume 62, through the orifices 178 (in the direction of arrow 236), and into the liquid waste receiver volume 64 towards the fluid absorber (in the direction of arrow 238). The fluid absorber with remaining capacity to absorb additional liquid absorbs the liquid contents originally comprising the solid phase pharmaceutical waste material. Consequently, the amount of liquid contents within the waste receiver 32 is minimized, and preferably eliminated, prior to transport, processing, and/or disposal. At no point during the above self-contained solidification process was the user exposed to external substances required to solidify the liquid contents within the solid receiver volume 86, as the cover 82 was coupled to the receiver body 36 prior to the user manipulating the waste receiver 32. Alternatively, the solid waste volume may be free of an absorber.

Additionally or alternatively, it is contemplated that at least a portion of the liquid contents may be directed from the solid waste receiver volume 62 to the liquid waste receiver volume 64 through the inlet 60' of the solid receiver guide 80 and the inlet of the liquid receiver guide 146 (with the pushing member 78 not sealing the inlet 60'). The underside of the cover 82 may be spaced apart from the upper wall 176 of the diverter 166. As a result, as the waste receiver 32 is manually repositioned or manipulated, such as inverted, such that the liquid contents within the solid waste receiver volume 62 descend under the influence of gravity (arrow 238). The liquid contents pass through the inlet 60', and into contact with the underside of the cover 82. The liquid contents move along the underside of the cover 82 and through the inlet of the liquid receiver guide 146. With further manipulation (e.g., returning the waste receiver 32 to upright), the liquid contents descend under the influence of gravity within the liquid waste receiver volume 64 (arrow 240).

Figure 15:
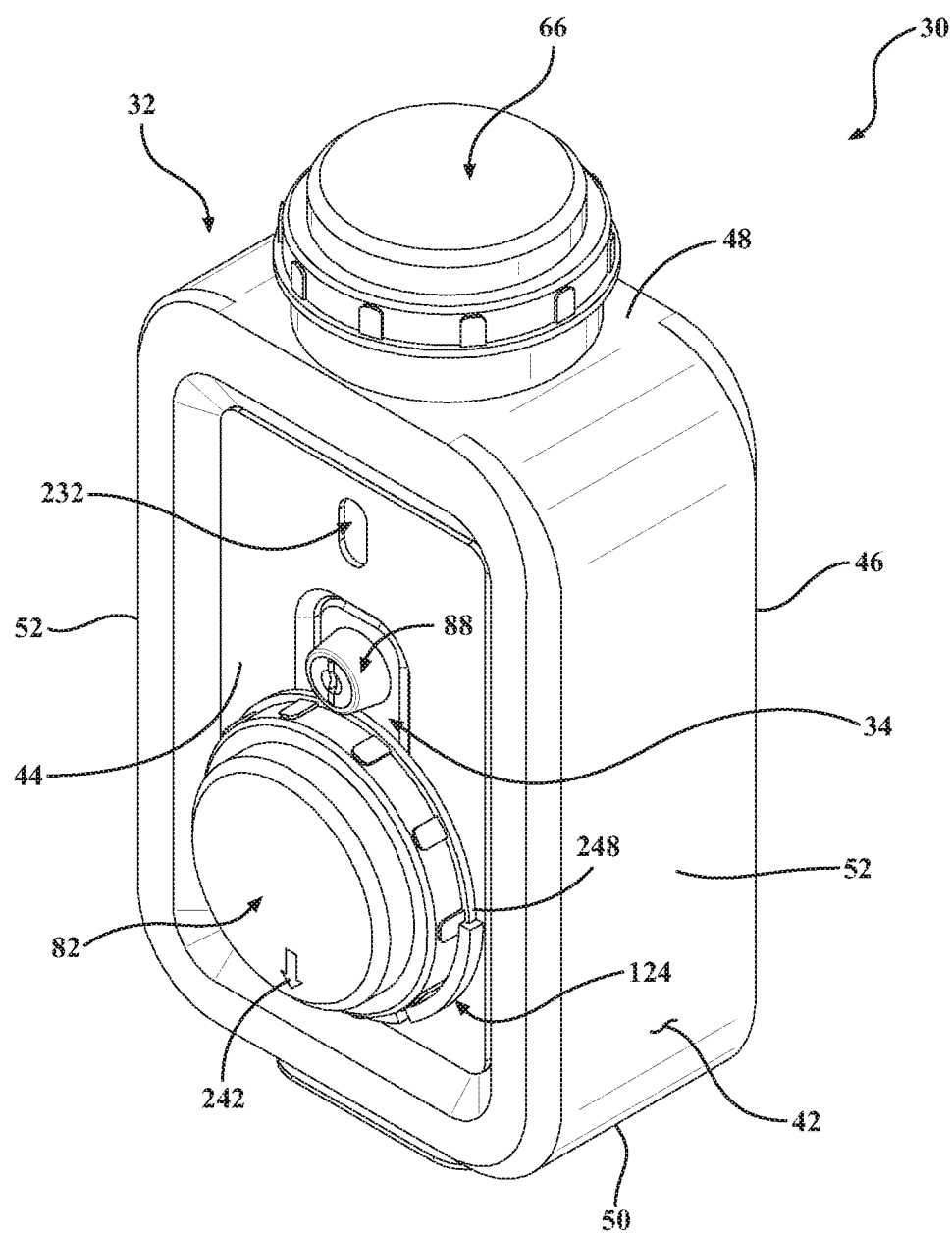
FIG. 15 is a perspective view of the waste disposal system including another waste receiver and the locking assembly.

One or more indicia 242 may be provided on a suitable location of the waste receiver 32 or the cover 82 to provide information to the user as to which direction to generally tip or agitate the waste receiver 32 to direct the liquid contents through the orifices 178 or the inlet 60'. FIG. 15 shows the indicia 242 including an arrow disposed on cover 82 with pointing towards a direction that, once the cover 82 is secured to the receiver body 36, corresponds to a direction of the orifices 178 relative to the solid waste receiver volume 62, and thus the direction to generally tip or agitate the waste receiver 32 during the self-contained solidification method. Additionally or alternatively, the indicia 242 (or additional indicia) may be provided on the body portion 168 of the diverter 166 so as to be visible to the user prior to sealing the solid phase pharmaceutical waste material and the liquid phase pharmaceutical waste material with the cover 82. Other shapes and positions of the indicia 242 are considered within the scope of the present disclosure.

Still another advantageous feature of the waste disposal system 30 may include a cover retention feature 124. As previously mentioned, the waste receiver system 30 may be assembled or packaged with a kit including the waste receiver 32, the cover 82, and the cap 66, the latter of which is removed and discarded upon installation of the waste receiver 32 at its service location. Yet the cover 82 remains decoupled from over the opening(s) 34, 35 of the receiver body 36 until the end of the operational lifecycle of the waste receiver 32. It is desirable to have the cover 82 at the ready should it be necessary to replace and dispose of the waste receiver 32. A known solution of coupling the cover with a tether with the cover dangling from the receiver body 36 is unsightly and may interfere with the depositing of the pharmaceutical waste material within the waste receiver.

With reference to FIGS. 15 and 16, the cover retention feature 124 of the present embodiment is different in construction than that previously introduced. The cover retention feature 124 is sized to removably receive the cover 82. The cover retention feature 124 may include a lip 244 extending from the front wall 44 of the receiver body 36. The lip may be arcuate with a radius approximate to that of the cover 82. The arcuate lip 244 may subtend an arc of 180°, as shown, or less but generally sufficient to prevent removal of the cover 82 with the waste receiver 32 coupled to the locking assembly 34. The lip 244 may also include a flange 246 defining a gap between the lip 244 and the front wall 52 with the gap sized to receive an outer rim 248 of the cover 82 (see FIG. 15). As is readily appreciated from the exploded view of FIG. 16, with the waste receiver 32 decoupled from the locking assembly 34, the cover 82 may be decoupled from the cover retention feature 124; i.e., slidably moved upwardly to disengage the lip 244 and the outer rim 248. Yet as is further appreciated from the perspective view of FIG. 15 with the waste receiver 32 coupled with the locking assembly 34, the cover 82 is prevented from being decoupled by the lock cylinder 88 of the locking assembly 34. In other words, the cover retention feature 124 and the locking assembly 34 cooperate to prevent removal of the cover 82 with the locking assembly 34 securing the waste receiver 32 to the fixed surface. The lock cylinder 88 extends from the front wall 104 of the lock housing 96 and is spaced from the lip 244 of the cover retention feature 124 by a distance sufficient to retain the cover 82 between the lip 244 and the lock cylinder 88 when the lock housing 96 is positioned within the lock passageway 90 and the waste receiver 32 is secured to the fixed surface. The distance may be slightly larger than a diameter of the cover 82.

The cover retention feature 124 may be at least functionally related to the decoupling member 110 and the complementary engagement features 106, 110 previously described. As mentioned, the decoupling member 110 moves the waste receiver 32 away from the fixed surface once the locking assembly 34 is moved to the unlocked configuration and the complementary engagement features 106, 110 disengage. The magnitude of the movement may be at least greater than an amount that the lock cylinder 88 extends from the front wall 104 of the lock housing 96. As a result, once moving the locking assembly 34 from the locked configuration to the unlocked configuration and the decoupling member 110 moves the waste receiver 32, the cover 82 becomes removably coupled with the cover retention feature 124.

In some respects, the waste receiver may be considered a "liquid only" variant of the waste disposal system 30 in which there is an absence of the solid receiver guide 80. Details of the "liquid only" variant are disclosed in the aforementioned International Publication No. WO2019/006346, the entire contents of which are hereby incorporated by reference.

Exemplary Clauses

Clause 1: A waste receiver for receiving a pharmaceutical waste material including at least a solid phase pharmaceutical waste material and a liquid phase pharmaceutical waste material with the waste receiver adapted to be releasably secured to a fixed surface, the waste receiver including: a receiver body defining an opening and including an inner surface defining a container volume in fluid communication with the opening; a solid receiver guide coupled to the receiver body and adapted to direct the solid phase pharmaceutical waste material to a solid waste volume within the container volume; a cutting element positioned within the solid receiver volume to cut the solid phase pharmaceutical waste material; and a pushing member movably disposed within the solid receiver guide and including a main body defining a handle, and a leg extending from the main body opposite the handle with the handle adapted to receive an input from a user to move the pushing member between a first position in which the main body is spaced from solid receiver guide to provide a window partially defined between the main body, the leg, and the solid receiver guide for receiving the solid phase pharmaceutical waste material, and a second position in which the main body is adjacent to the solid receiver guide to facilitate engagement of the solid phase pharmaceutical waste material with the cutting element.

Clause 2: The waste receiver of clause 1, wherein at least a portion of the leg of the pushing member is disposed within the solid waste volume when the pushing member is in the first and second positions.

Clause 3: The waste receiver of clauses 1 or 2, wherein the pushing member further includes a foot extending from the leg with the foot adapted to interfere with the solid receiver guide as the pushing member is in the first position to prevent the pushing member from decoupling from the waste receiver.

Clause 4: The waste receiver of any of clauses 1-3, wherein the pushing member further includes a gripping member coupled to the main body and adapted to engage a patch including the solid phase pharmaceutical waste material positioned within the window and the pushing member is moved from the first position to the second position.

Clause 5: The waste receiver of any of clauses 1-4, wherein the main body of the pushing member further defines a first portion and a second portion spaced apart from one another to define a slot therebetween with the slot sized to receive the cutting element.

Clause 6: The waste receiver of any of clauses 1-5, wherein the solid receiver guide defines an elongate opening with the cutting element oriented substantially perpendicular to the elongate opening.

Clause 7: The waste receiver of any of clauses 1-6, wherein the solid waste guide further includes a funnel member including a plurality of sections each including an inclined surface and spaced apart from one another to define a first gap positioned above the cutting element such that the funnel member is adapted to guide the solid waste material along the inclined surfaces towards the first gap to position the solid phase waste material directly above an edge of the cutting element.

Clause 8: The waste receiver of clause 7, wherein the plurality of sections are spaced apart from one another to define a second gap with the pushing member adapted to be slidably moved through the second gap as the pushing member moves from the first position to the second position, thereby facilitating the solid waste material moving through the first and second gaps and into engagement with the cutting element.

Clause 9: The waste receiver of any of clauses 1-8, further including a liquid receiver guide coupled to the receiver body and adapted to direct the liquid phase pharmaceutical waste material to a liquid waste volume within the container volume separate from the solid waste volume.

Clause 10: The waste receiver of clause 9, further including a cover adapted to be removably coupled with the receiver body to seal the solid phase pharmaceutical waste material and the liquid phase pharmaceutical waste material within the receiver body for disposal of the waste receiver.

Clause 11: A waste receiver for receiving a pharmaceutical waste material including at least a solid phase pharmaceutical waste material and a liquid phase pharmaceutical waste material with the waste receiver adapted to be releasably secured to a fixed surface, the waste receiver including: a receiver body defining an opening and including an inner surface defining a container volume in fluid communication with the opening; a solid receiver guide coupled to the receiver body and adapted to direct the solid phase pharmaceutical waste material to a solid waste volume within the container volume; a cutting element coupled to the solid receiver guide and disposed within the solid waste volume, wherein the solid receiver guide includes a funnel member defining a first gap above the cutting element; and a pushing member movably disposed within the solid receiver guide and adapted to receive and input and move the solid phase pharmaceutical waste material through the solid receiver guide with the pushing member including a main body defining a handle to receive the input, and a gripping member coupled to the main body, wherein the gripping member is adapted to impale a patch including the solid phase pharmaceutical waste material and retain the patch as the main body moves the patch through the first gap and into engagement with the cutting element.

Clause 12: The waste receiver of clause 11, wherein the gripping member is a spike.

Clause 13: A waste receiver for receiving a pharmaceutical waste material including at least a solid phase pharmaceutical waste material and a liquid phase pharmaceutical waste material with the waste receiver adapted to be releasably secured to a fixed surface, the waste receiver including: a receiver body defining an opening and including an inner surface defining a container volume in fluid communication with the opening; a solid receiver guide coupled to the receiver body and adapted to direct the solid phase pharmaceutical waste material to a solid waste volume within the container volume; a cutting element coupled to the solid receiver guide and disposed within the solid waste volume; and a pushing member movably disposed within the solid receiver guide and adapted to facilitate moving the solid phase pharmaceutical waste material through the solid receiver guide, wherein the solid receiver guide includes a funnel member including a plurality of flexible sections spaced apart from one another to define a first gap above the cutting element, and a second gap smaller than a thickness of the main body of the pushing member adapted slidably move through the second gap with the flexible sections adapted to resiliently deflect away from the pushing member as the main body moves the solid phase pharmaceutical waste material through the first and second gaps and into engagement with the cutting element.

Clause 14: The waste receiver of clause 13, wherein each of the flexible sections includes an inclined surface with the inclined surfaces oriented towards one another to guide the solid waste material towards the first gap to position the solid phase waste material directly above an edge of the cutting element.

Clause 15: The waste receiver of clauses 13 or 14, wherein the second gap is perpendicular to the first gap.

Clause 16: The waste receiver of any of clauses 13-15, wherein the funnel member is symmetric about the first gap.

Clause 17: The waste receiver of any of clauses 13-16, wherein the funnel member is symmetric about the second gap.

Clause 18: The waste receiver of any of clauses 13-17, wherein the cutting element is oriented parallel with the first gap.

Clause 19: The waste receiver of any of clauses 13-18, wherein the first and second gaps are sized to be smaller than pills including the solid waste pharmaceutical material such that the pills descend under influence of gravity to be supported on the sections above first gap.

Clause 20: A waste receiver for receiving a pharmaceutical waste material including at least a solid phase pharmaceutical waste material and a liquid phase pharmaceutical waste material with the waste receiver adapted to be releasably secured to a fixed surface, the waste receiver including: a receiver body defining an opening and including an inner surface defining a container volume a diverter coupled to the receiver body and including: (i) a body portion having a rim positioned adjacent the opening of the receiver body; (ii) a solid receiver guide coupled to the body portion and disposed within the receiver body with the solid receiver guide adapted to direct the solid phase pharmaceutical waste material to a solid waste volume within the container volume; (iii) a liquid receiver guide coupled to the body portion and disposed within the receiver body and adapted to direct the liquid phase pharmaceutical waste material to a liquid waste volume within the container volume with each of the solid receiver guide and the liquid receiver guide being in communication with the opening of the waste receiver; (iv) a partition within the container volume that at least partially separates the liquid waste volume from the solid waste volume; and (iv) at least one orifice within the partition for providing fluid communication between the liquid waste volume and the solid waste volume.

Clause 22: The waste receiver of clause 21, wherein the diverter includes a plurality of walls with one of the walls including the partition within the walls disposed within container volume and defining the solid waste volume that is substantially enclosed and separate from the liquid waste volume other than the at least one inlet.

Clause 23: A waste receiver for receiving a pharmaceutical waste material including at least a solid phase pharmaceutical waste material and a liquid phase pharmaceutical waste material with the waste receiver adapted to be releasably secured to a fixed surface, the waste receiver including: a receiver body defining an opening and including an inner surface defining a container volume: a diverter coupled to the receiver body and including: (i) a body portion having a rim positioned adjacent the opening of the receiver body; (ii) a solid receiver guide coupled to the body portion and disposed within the receiver body with the solid receiver guide defining an inlet and adapted to direct the solid phase pharmaceutical waste material received through the inlet to a solid waste volume within the container volume; (iii) a liquid receiver guide coupled to the body portion and disposed within the receiver body and adapted to direct the liquid phase pharmaceutical waste material to a liquid waste volume within the container volume with each of the solid receiver guide and the liquid receiver guide being in communication with the opening of the waste receiver; and a cover adapted to be coupled with the receiver body over the opening to seal the pharmaceutical waste material within the container with the cover including an inner surface spaced apart from the inlet of the solid receiver guide when the cover is coupled with the receiver body such that at least partially inverting the receiver body directs liquid in the solid waste volume to move through the inlet and the liquid receiver guide and into the liquid waste volume.

Clause 24: A method for preparing for disposal of solid phase pharmaceutical waste material and liquid phase pharmaceutical waste material contained within a waste receiver including a liquid waste volume substantially separate from a solid waste volume containing a liquid and the solid phase pharmaceutical waste material, and an inlet or opening providing fluid communication between the liquid waste volume and the solid waste volume, the method including the step of: manipulating the receiver body such that the liquid within the solid waste volume moves through the inlet or the opening into the liquid waste volume.

Clause 25: The method of clause 24, further including coupling a cover to the receiver body to seal the liquid and the solid phase pharmaceutical waste material within the receiver body with prior to the step of manipulating the receiver body.

Clause 26: The method of clauses 24 or 25, wherein the step of manipulating the receiver body further including at least partially inverting the receiver body to direct the liquid away from a bottom surface of the receiver body and towards the opening.

Clause 27: The method of any of clauses 24-26, further including receiving information from indicia disposed on the waste receiver as to a direction to manipulate the receiver body.

Clause 28: The method of clause 27, wherein the indicia is disposed on one of the diverter and a cover adapted to be coupled to the receiver body prior to the step of manipulating the receiver body.

Clause 29: A waste receiver for receiving solid phase pharmaceutical waste material and liquid phase pharmaceutical waste material, the waste receiver including: a receiver body defining an opening and including an inner surface defining a container volume; a diverter coupled to the receiver body and including: (i) a body portion having a rim positioned adjacent the opening of the receiver body; (ii) a solid receiver guide coupled to the body portion and disposed within the receiver body with the solid receiver guide adapted to direct the solid phase pharmaceutical waste material to a solid waste volume within the container volume; (iii) a liquid receiver guide coupled to the body portion and disposed within the receiver body and adapted to direct the liquid phase pharmaceutical waste material to a liquid waste volume within the container volume and separate from the solid waste volume, wherein the solid receiver guide and the liquid receiver guide are in communication with the opening of the waste receiver; and a cover adapted to cover the opening to seal the solid phase pharmaceutical waste material and the liquid phase pharmaceutical waste material within the receiver body for disposal of the waste receiver.

Clause 30: The waste receiver of clause 29, further including a cutting element coupled to the solid receiver guide with the cutting element and disposed within the solid waste volume with the cutting element positioned to cut the solid phase pharmaceutical waste material being directed through the solid receiver guide.

Clause 31: The waste receiver of clause 30, a pushing member movably disposed within the solid receiver guide and adapted to facilitate moving of the solid phase pharmaceutical waste material through the solid receiver guide and engagement of the solid phase pharmaceutical waste material with the cutting element.

Clause 32: The waste receiver of clauses 30 or 31, wherein the solid waste guide further includes a funnel member including a plurality of inclined surfaces oriented towards one another and spaced apart from one another to define a first gap positioned above the cutting element such that the funnel member is adapted to guide the solid waste material along the inclined surfaces towards the first gap.

Clause 33: The waste receiver of any of clauses 29-32, further including a barrier coupled to the body portion with the barrier movable from an open configuration to permit insertion of the solid phase pharmaceutical waste material within the solid receiver guide and a closed configuration to prevent the insertion of the solid phase pharmaceutical waste material within the solid receiver guide.

Clause 34: The waste receiver of clause 33, further including a biasing element coupled to the body portion and the barrier and adapted to bias the barrier to the closed configuration.

Clause 35: A method of converting a waste receiver for receiving a single phase of pharmaceutical waste material into a waste receiver for receiving two phases of pharmaceutical waste material with the waste receiver including a receiver body defining an opening and including an inner surface defining a container volume in fluid communication with the opening, opposing upper and lower walls, and at least one sidewall extend between the upper and lower walls, the method including the step of: positioning a body portion of a diverter at least partially within the receiver body such that a rim of the body portion is positioned adjacent the opening of the receiver body, a solid receiver guide coupled to the body portion is disposed within the receiver body with the solid receiver guide adapted to direct one of the two phases of the pharmaceutical waste material to a solid waste volume within the container volume, and a liquid receiver guide coupled to the body portion is disposed within the receiver body with the liquid receiver guide adapted to direct the other one of the two phases of the pharmaceutical waste material to a liquid waste volume within the container volume and separate from the solid waste volume.

Clause 36: The method of clause 35, further including the step of securing the rim of the body portion to the receiver body.

Clause 37: A waste disposal system for receiving pharmaceutical waste material including at least one of a solid phase pharmaceutical waste material and a liquid phase pharmaceutical waste material, the waste receiver system including: a waste receiver including a receiver body defining an opening and including an inner surface defining a container volume in fluid communication with the opening, and an outer surface opposite the inner surface, the outer surface defining a lock passageway separate from the opening; the waste receiver further includes a cover adapted to be coupled with the receiver body over the opening to seal the pharmaceutical waste material within the container volume for disposal of the waste receiver; the waste receiver further includes a cover retention feature sized to removably receive the cover with the cover retention feature configured to cooperate with a locking assembly to prevent removal of the cover when the locking assembly secures the waste receiver to a fixed surface, the cover coupled to the cover retention feature.

Clause 38: A method of operating a waste disposal system for receiving a pharmaceutical waste and securing a waste receiver to a fixed surface and locking assembly, the method including: providing a waste receiver including a receiver body defining an opening and including an inner surface defining a container volume in fluid communication with the opening, and an outer surface opposite the inner surface, the outer surface defining a lock passageway separate from the opening; the waste receiver further includes a cover retention feature, and a cover; positioning the waste receiver such that the lock passageway at least partially surrounds the locking assembly; locking the locking assembly to secure the waste receiver to the fixed surface such that the cover retention feature and the and the locking assembly cooperate to prevent removal of the cover when the locking assembly is actuated.

Clause 39: The method of clause 38, further including inserting pharmaceutical waste into the container volume.

Clause 40: The method of clause 39, further including unlocking the locking assembly to allow removal of the cover from the cover retention feature.

Clause 41: The method of clause 40, further including removing the cover from the cover retention feature, and securing the cover to close the opening.

It is to be appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A waste receiver for receiving pharmaceutical waste material and adapted to be releasably coupled to a locking assembly secured to a fixed surface, said waste receiver comprising:
   a receiver body defining a container volume and an opening in fluid communication with said container volume for receiving the pharmaceutical waste material, said receiver body comprising a front wall, a rear wall opposite said front wall, and opposing sidewalls extending between said front and rear walls, wherein said receiver body defines a lock passageway adapted to receive the locking assembly, said lock passageway being separate from said opening and extending through said receiver body between said front and rear walls, with apertures within said front and rear walls defining a portion of a lock passageway; and
   a reaction agent positioned within a region of said container volume defined between said lock passageway and one of said opposing sidewalls of said receiver body.

2. The waste receiver of claim 1, wherein said reaction agent is further positioned to be spaced apart from a bottom wall of said receiver body.

3. The waste receiver of claim 2, wherein said receiver body further comprises a support disposed within said container volume and configured to maintain the position of said reaction agent with said container volume.

4. The waste receiver of claim 2, further comprising two shells joined to one another to form said receiver body with each of said shells defining a portion of said container volume and a portion of said lock passageway.

5. The waste receiver of claim 4, further comprising a support coupled to at least one of said two shells, said support configured to maintain the position of said reaction agent with said container volume.

6. The waste receiver of claim 5, wherein said support is a plurality of projections extending between said two shells and spaced apart from one another to collectively define a cage sized to prevent more than minimal movement of said reaction agent.

7. A waste receiver for receiving pharmaceutical waste material and adapted to be releasably coupled to a locking assembly secured to a fixed surface, said waste receiver comprising:
a receiver body defining a container volume and an opening in fluid communication with said container volume for receiving the pharmaceutical waste material, said receiver body comprising a front wall, a rear wall opposite said front wall, and opposing sidewalls extending between said front and rear walls, wherein said receiver body defines a lock passageway adapted to receive the locking assembly, said lock passageway being separate from said opening and extending through said receiver body between said front and rear walls; and
a reaction agent positioned within a region of said container volume defined between said lock passageway and one of said opposing sidewalls of said receiver body;
wherein said container volume is a liquid waste receiver volume configured to receive liquid phase pharmaceutical waste material, said receiver body further defining a solid waste receiver volume substantially separate from said liquid waste receiver volume and configured to receive solid phase pharmaceutical waste material, wherein each of said liquid and solid waste receiver volumes are in communication with said opening.

8. The waste receiver of claim 7, wherein said receiver body further comprises a top wall extending between said opposing sidewalls, wherein said solid waste receiver volume is positioned between said lock passageway and said top wall.

9. The waste receiver of claim 1, wherein said lock passageway is oblong in shape.

10. The waste receiver of claim 9, wherein said lock passageway extends entirely through said receiver body.

11. The waste receiver of claim 1, wherein said reaction agent is a first reaction agent and said region is a first region, said waste receiver further comprising a second reaction agent positioned within a second region of said container volume defined between said lock passageway and the other one of said opposing sidewalls.

12. The waste receiver of claim 1, further comprising a packet including said reaction agent.

13. A waste receiver for receiving liquid and solid phase pharmaceutical waste material and adapted to be releasably coupled to a locking assembly secured to a fixed surface, said waste receiver comprising:
two shells joined to one another to form a receiver body defining an opening for receiving the liquid and solid phase pharmaceutical waste material, wherein said two shells cooperate to define a liquid waste receiver volume in fluid communication with said opening; and
a reaction agent positioned within said liquid waste receiver volume,
wherein said two shells each defining an aperture that cooperate to define a lock passageway separate from said opening and extending through said receiver body,
wherein a singular one of said two shells defines a solid waste receiver volume substantially separate from said liquid waste receiver volume and in fluid communication with said opening.

14. The waste receiver of claim 13, further comprising a reaction agent, said reaction agent being positioned with a region between said solid waste receiver volume and one of opposing sidewalls of said receiver body.

15. The waste receiver of claim 13, wherein said reaction agent is spaced apart from a bottom wall of said receiver body.

16. A waste receiver for receiving pharmaceutical waste material and adapted to be releasably coupled to a locking assembly secured to a fixed surface, said waste receiver comprising:
a receiver body defining a container volume and an opening in fluid communication with said container volume for receiving the pharmaceutical waste material, said receiver body comprising a front wall, a rear wall opposite said front wall, and opposing sidewalls extending between said front and rear walls, wherein said receiver body defines a lock passageway adapted to receive the locking assembly, said lock passageway being separate from said opening and extending through said receiver body between said front and rear walls; and
a reaction agent positioned within a region of said container volume defined between said lock passageway and one of said opposing sidewalls of said receiver body;
wherein said reaction agent is a first reaction agent and said region is a first region, said waste receiver further comprising a second reaction agent positioned within a second region of said container volume defined between said lock passageway and the other one of said opposing sidewalls.

17. The waste receiver of claim 16, wherein said reaction agent is further positioned to be spaced apart from a bottom wall of said receiver body.

18. The waste receiver of claim 17, wherein said receiver body further comprises a support disposed within said container volume and configured to maintain the position of said reaction agent with said container volume.

19. The waste receiver of claim 17, further comprising two shells joined to one another to form said receiver body with each of said shells defining a portion of said container volume and a portion of said lock passageway.

20. The waste receiver of claim 19, further comprising a support coupled to at least one of said two shells, said support configured to maintain the position of said reaction agent with said container volume.

* * * * *